(12) United States Patent
Unoki et al.

(10) Patent No.: US 7,417,053 B2
(45) Date of Patent: Aug. 26, 2008

(54) PYRAZOLO[1,5-A]PYRIDINE DERIVATIVES OR PHARMACEUTICALLY ACCEPTABLE SALTS THEREOF

(75) Inventors: Gen Unoki, Tokyo (JP); Yoshiyuki Matsumoto, Tokyo (JP); Yohei Matsueda, Tokyo (JP); Tomomi Kosugi, Tokyo (JP); Mika Takakuwa, Tokyo (JP); Hiroaki Makino, Yamaguchi (JP); Kenichiro Kataoka, Tokyo (JP); Yuko Yamakoshi, Tokyo (JP); Motoko Hamada, Tokyo (JP)

(73) Assignee: Teijin Pharma Limited, Tokoyo (JP)

( * ) Notice: Subject to any disclaimer, the term of this patent is extended or adjusted under 35 U.S.C. 154(b) by 189 days.

(21) Appl. No.: 11/399,484

(22) Filed: Apr. 7, 2006

(65) Prior Publication Data

US 2007/0072898 A1 Mar. 29, 2007

Related U.S. Application Data

(60) Provisional application No. 60/714,864, filed on Sep. 8, 2005, provisional application No. 60/669,894, filed on Apr. 11, 2005.

(30) Foreign Application Priority Data

Apr. 7, 2005 (JP) .............................. 2005-111419
Sep. 2, 2005 (JP) .............................. 2005-254677

(51) Int. Cl.
| | |
|---|---|
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(52) U.S. Cl. ...................................... 514/300; 546/121
(58) Field of Classification Search .................. 546/121; 514/300
See application file for complete search history.

(56) References Cited

FOREIGN PATENT DOCUMENTS

| JP | 2001/139575 | | 5/2001 |
|---|---|---|---|
| JP | 2001139575 | * | 5/2001 |
| WO | WO 2004/026872 | | 4/2004 |
| WO | WO 2004/026872 A1 | | 4/2004 |
| WO | WO 2004/054504 A2 | | 7/2004 |
| WO | WO 2004/054505 A2 | | 7/2004 |
| WO | WO 2004/055015 A1 | | 7/2004 |
| WO | WO 2004/055019 A1 | | 7/2004 |
| WO | WO 2004/058176 A2 | | 7/2004 |
| WO | WO 2004/058762 A1 | | 7/2004 |
| WO | WO 2004/076458 A1 | | 9/2004 |
| WO | WO 2004/081013 A1 | | 9/2004 |
| WO | WO 2004/099127 A1 | | 11/2004 |
| WO | WO 2005/007092 A2 | | 1/2005 |
| WO | WO 2005/009370 A2 | | 2/2005 |
| WO | WO 2005/028445 A2 | | 3/2005 |
| WO | WO 2005/077948 A1 | | 8/2005 |

OTHER PUBLICATIONS

Enrique Martin-Blanco, "p38 MAPK signalling cascades: ancient roles and new functions", BioEssays 22.7, pp. 637-645, 2000 John Wiley & Sons, Inc.
H. Y. Shin et al., "Regulatory Effect of Cytokine Production in Patients With Cerebral Infarction by Yulda-Hanso-Tang", Immunopharmacology and Immunotoxicology, 22(2), pp. 183-193, (2000).
David Stokoe et al., "Identification of MAPKAP kinase 2 as a major enzyme responsible for the phosphorylation of the small mammalian heat shock proteins", Federation of European Biochemical Societies, vol. 313, No. 3, pp. 307-313, published by Elsevier Science Publications, Nov. 1992.
Oliver Werz et al, "5-Lipoxygenase is phosphorylated by p38 kinase-dependent MAPKAP kinases", PNAS, May 9, 2000, vol. 97, No. 10, pp. 5261-5266.
Olaf Heidenreich et al., "MAPKAP Kinase 2 Phosphorylates Serum Response Factor in Vitro and in Vivo", The Journal of Biological Chemistry, vol. 274, No. 20, Issue of May 14, pp. 14434-14443, published by The American Society for Biochemistry and Molecular Biology, Inc., 1999.
Yi Tan et al., "FGF and stress regulate CREB and ATF-1 via a pathway involving p38 MAP kinase and MAPKAP kinase-2", The EMBO Journal, vol. 15, No. 17, pp. 4629-4642, published by Oxford University Press, 1996.
Bernd Neufeld et al, "Serine/Threonine Kinases 3pK and MAPK-activated Protein Kinase 2 Interact with the Basic Helix-Loop-Helix Transcription Factor E47 and Repress Its Transcriptional Activity", The Journal of Biological Chemistry, vol. 275, No. 27, Jul. 7, 2000 pp. 20239-20242, published by The American Society for Biochemistry and Molecular Biology, Inc., 2000.

(Continued)

*Primary Examiner*—D. Margaret Seaman
*Assistant Examiner*—Niloofar Rahmani
(74) *Attorney, Agent, or Firm*—Sughrue Mion, PLLC

(57) ABSTRACT

A pyrazolo[1,5-a]pyridine derivative represented by formula (I) and salt thereof exhibit excellent MAPKAP-K2 inhibitory activity. Accordingly, medicines comprising this compound as an active ingredient are expected to be valuable for treating or preventing diseases mediated by MAPKAP-K2 such as inflammatory injury, autoimmune diseases, asteropathia destruens, cancer and/or growth of tumor.

(I)

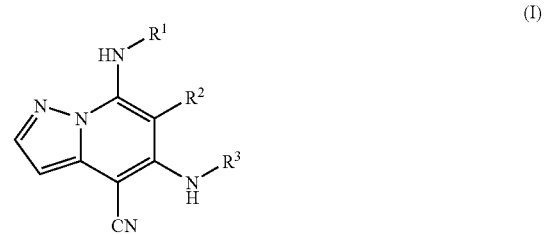

53 Claims, 1 Drawing Sheet

OTHER PUBLICATIONS

Davis Stokoe, et al., "The substrate specificity and structure of mitrogen-activated protein (MAP) kinase-activated protein kinase-2", Biochem J. (1993) 296, pp. 843-849.

Alexey Kotlyarov et al., MAPKAP kinase 2 is essential for LPS-induced TNF-α biosynthesis, Macmillian Magazines LtdNature Cell Biology, vol. 1, Jun. 1999.

Xinkang Wang et al., "Mitogen-activated Protein Kinase-activated Protei (MAPKAP) Kinase 2 Deficiency Protects Brain from Ischemic Injury in Mice", The Journal of Biological Chemistry, vol. 277, No. 46, Issues of Nov. 15, pp. 43968-43972, 2002 published by the American Society for Biochemistry and Molecular Biology, Inc.

Isaac A. Manke et al., "MAPKAP Kinase-2 Is a Cell Cycle Checkpoint Kinase that Regulates the $G_2$/M Transition and S Phase Progression in Response to UV Irradiation", Molecular Cell, vol. 17, pp. 37-48, Jan. 7, 2005 published by Elsevier Inc. 2005.

* cited by examiner

US 7,417,053 B2

PYRAZOLO[1,5-A]PYRIDINE DERIVATIVES OR PHARMACEUTICALLY ACCEPTABLE SALTS THEREOF

This application claims priority from U.S. Provisional Application No. 60/669,894, filed Apr. 11, 2005 and from U.S. Provisional Application No. 60/714,864, filed Sep. 8, 2005.

FIELD OF THE INVENTION

The present invention relates to a novel class of pyrazolo [1,5-a]pyridine derivatives or pharmaceutically acceptable salts thereof, pharmaceutical compositions comprising them as an active ingredient, MAPKAP-K2 (mitogen-activated protein kinase activated protein kinase 2) inhibitors comprising them as an active ingredient and novel intermediates thereof. The present invention also relates to therapeutic agents or preventing agents comprising these compounds as active ingredients for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

BACKGROUND OF THE INVENTION

MAPKAP-K2 (mitogen-activated protein kinase activated protein kinase 2) is a serine/threonine kinase and operates in immediate downstream of p38 kinase in stress-induced MAPK pathway (FIG. 1).

This p38 kinase pathway is activated by various stress-related extracellular stimuli such as heat, ultraviolet ray, bacterial lipopolysaccharide or inflammatory cytokines. The activation of this pathway causes phosphorylation of transcription and initiation factors and affects cell division, apoptosis, cell differentiation, inflammatory response and infiltration of cancer cells (Martin-Blanco, Bioessays 22, 637-645).

p38 Kinase itself activates many protein kinases other than MAPKAP kinase, for example, Mnkl/2, PRAK and MSK1 (FIG. 1). This pathway is particularly important for discovery of novel anti-inflammatory drugs. A selective p38 kinase inhibitor is effective for suppressing inflammatory cytokines in both cell based model and animal model of chronic inflammation (Lee et al., Immunopharmacology 47,185-201 (2000)). However, a p38 kinase-knockout mouse is embryonic lethal. Moreover, it has been proved that cells derived from such an embryo exhibit a lot of anomaly in fundamental cellular responses. As another strategy for developing anti-inflammatory drugs, there can be mentioned a drug inhibiting this pathway in the level of MAPKAP-K2. In an unstimulated cell, MAPKAP-K2 exists in the nucleus, and it is transferred to cytosol when the cell is stimulated. It is known that this kinase phosphorylates many nuclear transcription factors and cytosolic proteins such as heat-shock protein involved in cell protection and 5-lipoxygenase involved in bioprotection and inflammation (Stokoe et al., FEBS Lett. 313, 307-313 (1992); Werz et al., Proc. Natl. Acad. Sci. USA 97, 5261-5266 (2000)); Heindenreich et al., J. Biol. Chem. 274, 14434-14443 (1999)); Tan et al., EMBO J. 15, 4629-4642 (1996)); Neufeld, J. Biol. Chem. 275, 20239-20242 (2000)). All of these substrates contain a unique amino acid motif (XX-Hyd-XRXXSXX where Hyd represents a bulky hydrophobic residue) which is required for effective phosphorylation by MAPKAP-K2 (Stokoe et al., Biochem. J. 296, 843-849 (1993)).

MAPKAP-K2 is the only substrate of p38 kinase whose special function is currently identified. The special rolls of MAPKAP-K2 in mediation of inflammatory response are remarkably demonstrated in a phenotype of MAPKAP-K2 knockout mouse (MAPKAP-K2$^{-/-}$) (Kotlyarov et al., Nature Cell Biol. 1, 94-97 (1999)). This mouse is not lethal and normal except for particularly reduced inflammatory response. Recently, it has been proved that lack of MAPKAP-K2 causes particular protection of neurons from ischemic brain injury (Wang et al., J. Biol. Chem. 277, 43968-43972 (2002)). It is considered that MAPKAP-K2 regulates translation and/or stabilization of mRNA of important inflammatory cytokines. This is likely because MAPKAP-K2 phosphorylates proteins which bind to AU-rich elements found in untranslated regions of these cytokines. Identification of these proteins is now under investigation.

Furthermore, it is reported that MAPKAP-K2 has activity of repairing anomaly in DNA induced by ultraviolet ray (Isaac A. Manke et al., Molecular Cell 17, 37-48 (2005)). Inhibition of MAPKAP-K2 activity may disable repairing damaged DNA and cause death in some types of cancer cell.

From the above, MAPKAP-K2 inhibitors are effective for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

As MAPKAP-K2 inhibitors there have been disclosed in WO2004/054504, WO2004/054505, WO2004/055015, WO2004/055019, WO2004/058176, WO2004/058762, WO2004/099127, WO2005/009370, WO2005/007092, WO2004/076458 and WO2004/081013, but these compounds are different in structure from the compounds in the present invention.

Further, pyrazolo[1,5-a]pyridine derivatives are disclosed in WO2004/026872, WO2005/028445 and WO2005/077948. These compounds are, however, different in structure from the compound of the present invention or the compound of the present invention is not specifically disclosed in these literatures, as exemplified by the fact that WO2005/077948 describes only compounds wherein $R^3$ is a methyl group but no compounds wherein $R^3$ is a hydroxyl group or an amino group. Furthermore, the target enzymes of these compounds are also different from those of the compound of the present invention.

THE DISCLOSURE OF THE INVENTION

An object of the present invention is to provide a novel pyrazolo[1,5-a]pyridine derivative or pharmaceutically acceptable salt thereof valuable for a MAPKAP-K2 inhibitor.

Another object of the present invention is to provide a novel MAPKAP-K2 inhibitor or a novel therapeutic agent or preventing agents for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD). A still other object of the present invention is to provide a novel intermediate of novel MAPKAP-K2 inhibitor.

The present inventors pursued zealous study, found that novel pyrazolo[1,5-a]pyridine derivatives represented by the following formula (I) and pharmaceutically acceptable salts thereof exhibit excellent MAPKAP-K2 inhibitory activity, and accomplished the present invention.

Namely, the present invention is

<1> A pyrazolo[1,5-a]pyridine derivative represented by formula (I) or pharmaceutically acceptable salt thereof:

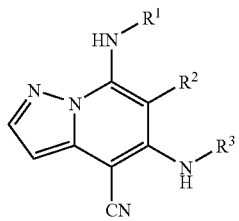

(I)

[In formula (I),

R$^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of R$^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, —OR$^{1a}$, —SR$^{1b}$, —NR$^{1c}$R$^{1d}$, —C(=O)R$^{1e}$, —S(=O)$_2$NR$^{1f}$R$^{1g}$, —C(=O)OR$^{1h}$, —C(=O)NR$^{1i}$R$^{1j}$, —NR$^{1k}$C(=O)R$^{1l}$ and —NR$^{1m}$S(=O)$_2$R$^{1n}$;

R$^{1x}$ (x represents a, b, c, d, e, f g, h, i, j, k, l, m or n) may be identical or different, and represents a hydrogen atom, an optionally substituted C1-C8 alkyl group (when two C1-C8 alkyl groups as R$^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when R$^1$ is an optionally substituted C6-C14 aryl group or an optionally substituted heteroaryl group and two or more substituents of R$^1$ bond to R$^1$, these substituents may bond to each other via an oxygen atom, a nitrogen atom, a sulfur atom or a single bond to form a ring;

R$^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of R$^2$ are one or more substituent(s) selected from the group consisting of a halogen atom, a cyano group, a nitro group, an optionally substituted C1-C8 alkyl group, —OR$^{2a}$, SR$^{2b}$, —NR$^{2c}$R$^{2d}$, —C(=O)R$^{2e}$, —S(=O)$_2$NR$^{2f}$R$^{2g}$, —C(=O)OR$^{2h}$, —C(=O)NR$^{2i}$R$^{2j}$, —NR$^{2k}$C(=O)R$^{2l}$ and —NR$^{2m}$S(=O)$_2$R$^{2n}$;

R$^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as R$^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when R$^2$ is an optionally substituted C6-C14 aryl group or an optionally substituted heteroaryl group and two or more substituents of R$^2$ bond to R$^2$, these substituents may bond to each other via an oxygen atom, a nitrogen atom, a sulfur atom or a single bond to form a ring;

R$^3$ represents an optionally substituted C1-C8 alkyl group, an optionally substituted C3-C8 cycloalkyl group or an optionally substituted aliphatic heterocyclic group;

the substituent(s) of R$^3$ are one or more substituent(s) selected from the group consisting of a halogen atom, a cyano group, a nitro group, —OR$^{3a}$, —SR$^{3b}$, —NR$^{3c}$R$^{3d}$, an optionally substituted C1-C8 alkyl group, an optionally substituted C3-C8 cycloalkyl group and an optionally substituted aliphatic heterocyclic group;

R$^{3z}$ (z represents a, b, c or d) may be identical or different and represents a hydrogen atom, an optionally substituted C1-C8 alkyl group (when two C1-C8 alkyl groups as R$^{3z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group; and the substituent(s) of substituent of R$^1$, R$^2$ and R$^3$ are, unless specifically defined, one or more substituent(s) selected from the group consisting of a halogen atom; a hydroxyl group; a cyano group; a nitro group; an amino group; an oxo group; a carboxyl group; a trifluoromethyl group; a pentafluoroethyl group; a trifluoromethoxy group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group cycloalkyl-oxy group optionally substituted with methyl group(s), halogen atom(s), hydroxyl group(s) or cyano group(s); an aliphatic heterocyclic group optionally substituted with methyl group(s), halogen atom(s), hydroxyl group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s).].

<2> The pyrazolo[1,5-a]pyridine derivative or pharmaceutically acceptable salt thereof according to <1>, wherein:

R$^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of $R^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-SR^{1b}$, $-NR^{1c}R^{1d}$, $-C(=O)R^{1e}$, $-S(=O)_2NR^{1f}R^{1g}$, $-C(=O)OR^{1h}$, $-C(=O)NR^{1i}R^{1j}$, $-NR^{1k}C(=O)R^{1l}$ and $-NR^{1m}S(=O)_2R^{1n}$;

$R^{1x}$ (x represents a, b, c, d, e, f, g, h, i, j, k, l, m or n) may be identical or different and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$, these substituents may bond to each other via an oxygen atom, a nitrogen atom, a sulfur atom or a single bond to form a ring;

$R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group or an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, $-OR^{2a}$, $SR^{2b}$, $-NR^{2c}R^{2d}$, $-C(=O)R^{2e}$, $-S(=O)_2NR^{2f}R^{2g}$, $-C(=O)OR^{2h}$, $-C(=O)NR^{2i}R^{2j}$, $-NR^{2k}C(=O)R^{2l}$ and $-NR^{2m}S(=O)_2R^{2n}$;

$R^{2y}$ (y represents a, b, c, d, e, f, g, h, i, j, k, l, m or n) may be identical or different and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring;

$R^3$ represents an optionally substituted C1-C8 alkyl group, an optionally substituted C3-C8 cycloalkyl group or an optionally substituted aliphatic heterocyclic group;

the substituent(s) of $R^3$ are one or more substituent(s) selected from the group consisting of a halogen atom, a cyano group, a nitro group, $-OR^{3a}$, $-SR^{3b}$, $-NR^{3c}R^{3d}$, an optionally substituted C1-C8 alkyl group, an optionally substituted C3-C8 cycloalkyl group and an optionally substituted aliphatic heterocyclic group;

$R^{3z}$ (z represents a, b, c or d) may be identical or different and represents a hydrogen atom, an optionally substituted C1-C8 alkyl group (when two C1-C8 alkyl groups as $R^{3z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group; and the substituent(s) of substituent of $R^1$, $R^2$ and $R^3$ are, unless specifically defined, one or more substituent(s) selected from the group consisting of a halogen atom; a hydroxyl group; a cyano group; a nitro group; an amino group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group cycloalkyl-oxy group optionally substituted with methyl group(s), halogen atom(s), hydroxyl group(s) or cyano group(s); an aliphatic heterocyclic group optionally substituted with methyl group(s), halogen atom(s), hydroxyl group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s).

<3> The pyrazolo[1,5-a]pyridine derivative or pharmaceutically acceptable salt thereof according to <1> or <2>, except for:

compounds wherein $R^1$ is an unsubstituted or fluorinated C1-C6 alkyl group or an unsubstituted C3-C7 cycloalkyl group; $R^2$ is an unsubstituted C1-C6 alkyl group or a C1-C6 alkyl group substituted with a halogen atom, a hydroxyl group or $-NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6 alkyl group or an unsubstituted C3-C7 cycloalkyl group); and $R^3$ is an unsubstituted C1-C6 alkyl group:

compounds wherein $R^1$ is an unsubstituted C1-C6 alkyl group or an unsubstituted or halogenated phenyl group; $R^2$ is an unsubstituted C1-C6 alkyl group or a C1-6 alkyl group substituted with a halogen atom, a —OH or $-NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6 alkyl group or an unsubstituted C3-C7 cycloalkyl group); and $R^3$ is an unsubstituted or fluorinated C1-C6 alkyl group or an unsubstituted C3-C7 cycloalkyl group: and compounds wherein $R^1$ is a C1-C8 alkyl group substituted with $-NR^{1c}R^{1d}$, $-NR^{1k}-CO-R^{1l}$ or $-NR^{1m}S(=O)_2R^{1n}$ or a C3-C8 cycloalkyl group substituted with $-NR^{1c}R^{1d}$, $-NR^{1k}-CO-R^{1l}$ or $-NR^{1m}S(=O)_2R^{1n}$; and $R^3$ is an unsubstituted alkyl group or an alkyl group substituted with $OR^{3a}$.

<4> The pyrazolo[1,5-a]pyridine derivative or pharmaceutically acceptable salt thereof according to <1> or <2>, wherein:

R$^1$ is a C1-C8 alkyl group substituted with substituent(s) other than a fluorine atom, —NR$^{1c}$R$^{1d}$, —NR$^{1k}$—CO—R$^{1l}$ or —NR$^{1m}$S(=O)$_2$R$^{1n}$, an optionally substituted C2-C8 alkenyl group, an optionally substituted C2-C8 alkynyl group, a C6 aryl group substituted with substituent(s) other than halogen atoms, an optionally substituted C7-C14 aryl group, an optionally substituted heteroaryl group, an optionally substituted C7-C16 aralkyl group, an optionally substituted heteroarylalkyl group, a C3-C8 cycloalkyl group substituted with substituent(s) other than, —NR$^{1c}$R$^{1d}$, —NR$^{1k}$—CO—R$^{1l}$ or —NR$^{1m}$S(=O)$_2$R$^{1n}$, or an optionally substituted aliphatic heterocyclic group; and R$^3$ is a C1-C8 alkyl group substituted with substituent(s) other than a fluorine atom or —OR$^{3a}$, a substituted C3-C8 cycloalkyl group or an optionally substituted aliphatic heterocyclic group.

<5> The pyrazolo[1,5-a]pyridine derivative or pharmaceutically acceptable salt thereof according to any of <1> to <4>, wherein R$^1$ is an optionally substituted C1-C8 alkyl group, an optionally substituted C6-C14 aryl group, an optionally substituted heteroaryl group, an optionally substituted C7-C16 aralkyl group, an optionally substituted heteroarylalkyl group or an optionally substituted C3-C8 cycloalkyl group.

<6> The pyrazolo[1,5-a]pyridine derivative or pharmaceutically acceptable salt thereof according to any of <1> to <4>, wherein R$^1$ is an optionally substituted C1-C8 alkyl group, an optionally substituted C6-C14 aryl group or an optionally substituted heteroaryl group.

<7> The pyrazolo[1,5-a]pyridine derivative or pharmaceutically acceptable salt thereof according to any of <1> to <4>, wherein R$^1$ is an optionally substituted C6-C14 aryl group or an optionally substituted heteroaryl group.

<8> The pyrazolo[1,5-a]pyridine derivative or pharmaceutically acceptable salt thereof according to any of <1> to <4>, wherein R$^1$ is an optionally substituted phenyl group.

<9> The pyrazolo[1,5-a]pyridine derivative or pharmaceutically acceptable salt thereof according to any of <1> to <4>, wherein R$^1$ is an optionally substituted heteroaryl group.

<10> The pyrazolo[1,5-a]pyridine derivative or pharmaceutically acceptable salt thereof according to <9>, wherein R$^1$ is a heteroaryl group wherein a phenyl group and an optionally substituted monocyclic heteroaryl ring are fused and the phenyl group bonds to the NH group at the 7 position of the pyrazolo[1,5-a]pyridine derivative of formula (I).

<11> The pyrazolo[1,5-a]pyridine derivative or pharmaceutically acceptable salt thereof according to any of <1> to <4>, wherein R$^1$ is an optionally substituted C7-C16 aralkyl group or an optionally substituted heteroarylalkyl group.

<12> The pyrazolo[1,5-a]pyridine derivative or pharmaceutically acceptable salt thereof according to any of <1> to <11>, wherein the substituent(s) of R$^1$ are one or more substituent(s) selected from the group consisting of a fluorine atom, a chlorine atom, a cyano group, a nitro group, an optionally substituted C1-C6 alkyl group, an optionally substituted C3-C8 cycloalkyl group, an optionally substituted C1-C6 alkoxy group, an optionally substituted C1-C6 alkylthio group, an optionally substituted phenyl group, an optionally substituted heteroaryl group, an optionally substituted C1-C6 acyl group, an optionally substituted C1-C6 acylamino group, an optionally substituted aminosulfonyl group (when two alkyl groups bond to the aminosulfonyl group, they may be identical or different and they may bond to each other via an oxygen atom, a nitrogen atom, a sulfur atom or a single bond to form a ring), an optionally substituted C2-C7 alkoxycarbonyl group, an optionally substituted sulfonylamino group and an optionally substituted carbamoyl group (when two alkyl groups bond to the carbamoyl group, they may be identical or different and they may bond to each other via an oxygen atom, a nitrogen atom, a sulfur atom or a single bond to form a ring).

<13> The pyrazolo[1,5-a]pyridine derivative or pharmaceutically acceptable salt thereof according to any of <1> to <11>, wherein the substituent(s) of R$^1$ are one or more substituent(s) selected from the group consisting of a fluorine, atom a chlorine atom, a cyano group, a nitro group, an optionally substituted C1-C6 alkylthio group, an optionally substituted C1-C6 acyl group, an optionally substituted C1-C6 acylamino group, an optionally substituted aminosulfonyl group (when two alkyl groups bond to the aminosulfonyl group, they may be identical or different and they may bond to each other via an oxygen atom, a nitrogen atom, a sulfur atom or a single bond to form a ring), an optionally substituted C2-C7 alkoxycarbonyl group, an optionally substituted sulfonylamino group and an optionally substituted carbamoyl group (when two alkyl groups bond to the carbamoyl group, they may be identical or different and they may bond to each other via an oxygen atom, a nitrogen atom, a sulfur atom or a single bond to form a ring).

<14> The pyrazolo[1,5-a]pyridine derivative or pharmaceutically acceptable salt thereof according to any of <1> to <11>, wherein the substituent(s) of R$^1$ are one or more substituent(s) selected from the group consisting of a fluorine atom, a chlorine atom, a cyano group, a nitro group, an optionally substituted phenyl group and an optionally substituted heteroaryl group.

<15> The pyrazolo[1,5-a]pyridine derivative or pharmaceutically acceptable salt thereof according to any of <1> to <11>, wherein the substituent(s) of R$^1$ are a substituent selected from the group consisting of an optionally substituted phenyl group and an optionally substituted heteroaryl group; and the substituent(s) of R$^1$ may contain one or more substituent(s) selected from the group consisting of a fluorine atom, a chlorine atom, a cyano group and a nitro group.

<16> The pyrazolo[1,5-a]pyridine derivative or pharmaceutically acceptable salt thereof according to any of <1> to <11>, wherein the substituent(s) of R$^1$ are one or more substituent(s) selected from the group consisting of a fluorine atom; a chlorine atom; a cyano group; a C1-C6 alkyl group(s) optionally substituted with one or more substituent(s) selected from the group consisting of a halogen atom, a hydroxyl group and a cyano group; a C3-C8 cycloalkyl group(s) optionally substituted with one or more substituent(s) selected from the group consisting of a halogen atom, a hydroxyl group and a cyano group; a C1-C6 alkyl group(s) substituted with a C1-6 alkoxy group optionally substituted with one or more substituent(s) selected from the group consisting of a halogen atom, a hydroxyl group and a cyano group; and a C1-C6 alkyl group(s) substituted with a C3-C6 cycloalkyl-oxy group optionally substituted with one or more substituent(s) selected from the group consisting of a methyl group, a halogen atom, a hydroxyl group, a cyano group and an oxo group.

<17> The pyrazolo[1,5-a]pyridine derivative or pharmaceutically acceptable salt thereof according to any one of <1> to <11>, wherein:

the substituent(s) of $R^1$ are one or more substituent(s) selected from the group consisting of:

a C1-C6 alkyl group(s) optionally substituted with one or more substituent(s) selected from the group consisting of a halogen atom, a hydroxyl group and a cyano group;

a C3-C8 cycloalkyl group(s) optionally substituted with one or more substituent(s) selected from the group consisting of a halogen atom, a hydroxyl group and a cyano group;

a C1-C6 alkyl group(s) substituted with a C1-C6 alkoxy group optionally substituted with one or more substituent(s) selected from the group consisting of a halogen atom, a hydroxyl group and a cyano group; a C1-C6 alkyl group substituted with a C3-C6 cycloalkyl-oxy group cycloalkyl-oxy group optionally substituted with one or more substituent(s) selected from the group consisting of a methyl group, a halogen atom, a hydroxyl group, a cyano group and an oxo group; and the substituent(s) of $R^1$ may contain one or more substituent(s) selected from the group consisting of a fluorine atom, a chlorine atom and a cyano group.

<18> The pyrazolo[1,5-a]pyridine derivative or pharmaceutically acceptable salt thereof according to any of <1> to <11>, wherein:

the substituent(s) of $R^1$ are one or more substituent(s) selected from the group consisting of:

a C1-C6 alkyl group(s) optionally substituted with one or more substituent(s) selected from the group consisting of a carboxyl group, an oxo group and a C1-C6 alkoxy group optionally substituted with one or more substituent(s) selected from the group consisting of a halogen atom, a hydroxyl group and a cyano group;

a C1-6 alkyl group(s) optionally substituted with a heteroaryl group optionally substituted with one or more substituent(s) selected from the group consisting of a methyl group, a halogen atom, a hydroxyl group and a cyano group; and a C1-C6 alkyl group(s) optionally substituted with an aliphatic heterocyclic group optionally substituted with one or more substituent(s) selected from the group consisting of a methyl group, a halogen atom, a hydroxyl group and a cyano group; and the substituent(s) of $R^1$ may contain one or more substituent(s) selected from the group consisting of a fluorine atom, a chlorine atom, a cyano group and a methyl group.

<19> The pyrazolo[1,5-a]pyridine derivative or pharmaceutically acceptable salt thereof according to any of <1> to <11>, wherein the substituent(s) of $R^1$ are C1-C6 alkyl group(s) optionally substituted with one or more substituent(s) selected from the group consisting of a halogen atom, a hydroxyl group and a cyano group.

<20> The pyrazolo[1,5-a]pyridine derivative or pharmaceutically acceptable salt thereof according to any of <1> to <11>, wherein the substituent(s) of $R^1$ are one or more substituent(s) selected from the group consisting of:

a fluorine atom;

a chlorine atom;

a cyano group;

a C1-C6 alkoxy group(s) optionally substituted with one or more substituent(s) selected from the group consisting of a halogen atom, a hydroxyl group and a cyano group;

a C1-C6 alkoxy group(s) substituted with an aliphatic heterocyclic group optionally substituted with one or more substituent(s) selected from the group consisting of a methyl group, a halogen atom, a hydroxyl group and a cyano group;

a C1-C6 alkoxy group(s) substituted with a C1-C6 alkoxy group(s) optionally substituted with one or more substituent(s) selected from the group consisting of a halogen atom, a hydroxyl group, and a cyano group; and a C1-C6 alkoxy group(s) substituted with a C3-C6 cycloalkyl-oxy group cycloalkyl-oxy group optionally substituted with one or more substituent(s) selected from the group consisting of a methyl group, a halogen atom, a hydroxyl group, a cyano group and an oxo group.

<21> The pyrazolo[1,5-a]pyridine derivative or pharmaceutically acceptable salt thereof according to any of <1> to <11>, wherein the substituent(s) of $R^1$ are one or more substituent(s) selected from the group consisting of:

a C1-6 alkoxy group(s) optionally substituted with one or more substituent(s) selected from the group consisting of a halogen atom, a hydroxyl group and a cyano group;

a C1-C6 alkoxy group(s) substituted with an aliphatic heterocyclic group optionally substituted with one or more substituent(s) selected from the group consisting of a methyl group, a halogen atom, a hydroxyl group and a cyano group;

a C1-C6 alkoxy group(s) substituted with a C1-C6 alkoxy group optionally substituted with one or more substituent(s) selected from the group consisting of a halogen atom, a hydroxyl group and a cyano group; and a C1-6 alkoxy group(s) substituted with a C3-C6 cycloalkyl-oxy group cycloalkyl-oxy group optionally substituted with one or more substituent(s) selected from the group consisting of a methyl group, a halogen atom, a hydroxyl group, a cyano group and an oxo group; and the substituent(s) of $R^1$ may contain one or more substituent(s) selected from the group consisting of a fluorine atom, a chlorine atom and a cyano group.

<22> The pyrazolo[1,5-a]pyridine derivative or pharmaceutically acceptable salt thereof according to any of <1> to <11>, wherein the substituent(s) of $R^1$ are one or more substituent(s) selected from the group consisting of:

a C1-C6 alkoxy group(s) optionally substituted with one or more substituent(s) selected from the group consisting of a carboxyl group, an oxo group and a C1-C6 alkoxy group(s) optionally substituted with one or more substituent(s) selected from the group consisting of a halogen atom, a hydroxyl group and a cyano group; and a C1-C6 alkoxy group(s) optionally substituted with a heteroaryl group optionally substituted with one or more substituent(s) selected from the group consisting of a methyl group, a halogen atom, a hydroxyl group and a cyano group; and the substituent(s) of $R^1$ may contain one or more substituent(s) selected from the group consisting of a fluorine atom, a chlorine atom, a cyano group and a methyl group.

<23> The pyrazolo[1,5-a]pyridine derivative or pharmaceutically acceptable salt thereof according to any of <1> to <11>, wherein the substituent(s) of $R^1$ are C1-C6 alkoxy group(s) optionally substituted with one or more substituent(s) selected from the group consisting of a halogen atom, a hydroxyl group and a cyano group.

<24> The pyrazolo[1,5-a]pyridine derivative or pharmaceutically acceptable salt thereof according to any of <1> to <23>, wherein $R^2$ is a hydrogen atom, an optionally substituted C1-C8 alkyl group, an optionally substituted C2-C8 alkenyl group, an optionally substituted C6-C14 aryl group, an optionally substituted heteroaryl group, an optionally substituted C7-C16 aralkyl group, an optionally substituted heteroarylalkyl group, or an optionally substituted C3-C8 cycloalkyl group.

<25> The pyrazolo[1,5-a]pyridine derivative or pharmaceutically acceptable salt thereof according to any of <1> to <23>, wherein $R^2$ is a hydrogen atom, an optionally substituted C1-C6 alkyl group, an optionally substituted C2-C6 alkenyl group, an optionally substituted C6-C14 aryl group, an optionally substituted heteroaryl group, an optionally substituted C7-C12 phenylalkyl group or an optionally substituted C3-C6 cycloalkyl group.

<26> The pyrazolo[1,5-a]pyridine derivative or pharmaceutically acceptable salt thereof according to any of <1> to <23>, wherein $R^2$ is a hydrogen atom, an optionally substituted C1-C6 alkyl group, an optionally substituted C2-C6 alkenyl group, or an optionally substituted C3-C6 cycloalkyl group.

<27> The pyrazolo[1,5-a]pyridine derivative or pharmaceutically acceptable salt thereof according to any of <1> to <23>, wherein R is an optionally substituted C1-C6 alkyl group or an optionally substituted C2-C6 alkenyl group.

<28> The pyrazolo[1,5-a]pyridine derivative or pharmaceutically acceptable salt thereof according to any of <1> to <23>, wherein $R^2$ is an optionally substituted C1-C4 alkyl group.

<29> The pyrazolo[1,5-a]pyridine derivative or pharmaceutically acceptable salt thereof according to any of <1> to <23, wherein $R^2$ is a hydrogen atom.

<30> The pyrazolo[1,5-a]pyridine derivative or pharmaceutically acceptable salt thereof according to any of <1> to <23>, wherein $R^2$ is an optionally substituted phenyl group or an optionally substituted heteroaryl group.

<31> The pyrazolo[ 1,5-a]pyridine derivative or pharmaceutically acceptable salt thereof according to any of <1> to <4) and <24> to <30>, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 alkyl group, an optionally substituted C1-C6 alkoxy group, an optionally substituted C1-C6 acyl group, an optionally substituted aminosulfonyl group (when two alkyl groups bond to the aminosulfonyl group, they may be identical or different and may bond to each other via an oxygen atom, a nitrogen atom, a sulfur atom or a single bond to form a ring), an optionally substituted sulfonylamino group and an optionally substituted carbamoyl group (when two alkyl groups bond to the carbamoyl group, they may be identical or different and may bond to each other via an oxygen atom, a nitrogen atom, a sulfur atom or a single bond to form a ring).

<32> The pyrazolo[1,5-a]pyridine derivative or pharmaceutically acceptable salt thereof according to any of <1> to <4>and <24> to <30>, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 acyl group and an optionally substituted carbamoyl group (when two alkyl groups bond to the carbamoyl group, they may be identical or different and may bond to each other via an oxygen atom, a nitrogen atom, a sulfur atom or a single bond to form a ring).

<33> The pyrazolo[1,5-a]pyridine derivative or pharmaceutically acceptable salt thereof according to any of <1> to <4> and claims <24> to <30>, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 alkyl group and an optionally substituted C1-C6 alkoxy group.

<34> The pyrazolo[1,5-a]pyridine derivative or pharmaceutically acceptable salt thereof according to any of <1> to <33>, wherein $R^3$ is an optionally substituted C1-C8 alkyl group, an optionally substituted C3-C8 cycloalkyl group or an optionally substituted aliphatic heterocyclic group.

<35> The pyrazolo[1,5-a]pyridine derivative or pharmaceutically acceptable salt thereof according to any of <1> to <33>, wherein $R^3$ is an optionally substituted C3-C8 cycloalkyl group or an optionally substituted aliphatic heterocyclic group having 1 to 4 nitrogen atom(s) as heteroatoms.

<36> The pyrazolo[1,5-a]pyridine derivative or pharmaceutically acceptable salt thereof according to any of <1> to <33>, wherein $R^3$ is an optionally substituted C5-C6 cycloalkyl group, an optionally substituted piperidyl group, an optionally substituted pyrrolidinyl group or an optionally substituted hexahydroazepinyl group.

<37> The pyrazolo[1,5-a]pyridine derivative or pharmaceutically acceptable salt thereof according to any of <> to <33>, wherein $R^3$ is an optionally substituted cyclohexyl group, an optionally substituted piperidyl group or an optionally substituted pyrrolidinyl group.

<38> The pyrazolo[1,5-a]pyridine derivative or pharmaceutically acceptable salt thereof according to any of <1> to <33>, wherein $R^3$ is an optionally substituted piperidyl group.

<39> The pyrazolo[1,5-a]pyridine derivative or pharmaceutically acceptable salt thereof according to any of <1> to <33>, wherein $R^3$ is an optionally substituted C1-C4 alkyl group.

<40> The pyrazolo[1,5-a]pyridine derivative or pharmaceutically acceptable salt thereof according to any of <1> to <4> and <34> to <39>, wherein the substituent(s) of $R^3$ are one or more substituent(s) selected from the group consisting of a fluorine atom, a hydroxyl group, a cyano group, an optionally substituted C1-C6 alkyl group and an optionally substituted amino group (when two alkyl groups bond to the amino group, they may be identical or different and may bond to each other via an oxygen atom, a nitrogen atom, a sulfur atom or a single bond to form a ring).

<41> The pyrazolo[1,5-a]pyridine derivative or pharmaceutically acceptable salt thereof according to any of <1> to <4> and <34> to <39>, wherein the substituent(s) of $R^3$ are one or more substituent(s) selected from the group consisting of a fluorine atom; a hydroxyl group; a cyano group; an optionally substituted amino group (when two alkyl groups bond to the amino group, they may be identical or different and may bond to each other via an oxygen atom, a nitrogen atom, a sulfur atom or a single bond to form a ring); a C5-C6 cycloalkyl group optionally substituted with an optionally substituted amino group (when two alkyl groups bond to the amino group, they may be identical or different and may bond to each other via an oxygen atom, a nitrogen atom, a sulfur atom or a single bond to form a ring); a piperazino group optionally substituted with C1-C6 alkyl group(s) optionally substituted with fluorine atom(s) or hydroxyl group(s), a piperidyl group optionally substituted with C1-C6 alkyl group(s) optionally substituted with fluorine atom(s) or hydroxyl group(s) or a pyrrolidinyl group optionally substituted with C1-C6 alkyl group(s) optionally substituted with fluorine atom(s) or hydroxyl group(s).

<42> A pyrazolo[1,5-a]pyridine derivative represented by formula (6) or salt thereof:

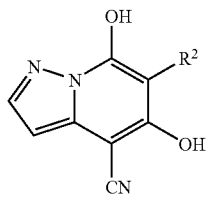
(6)

wherein $R^2$ is as defined in formula (I).

<43> A pyrazolo[1,5-a]pyridine derivative represented by formula (7) or salt thereof:

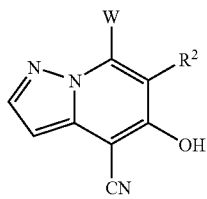
(7)

wherein $R^2$ as defined in formula (I) and W represents a halogen atom.

<44> A pyrazolo[1,5-a]pyridine derivative represented by formula (8) or salt thereof:

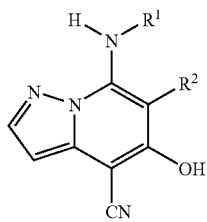
(8)

wherein $R^1$ and $R^2$ are as defined in formula (I).

<45> A pyrazolo[1,5-a]pyridine derivative represented by formula (9) or salt thereof:

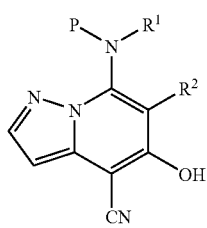
(9)

wherein $R^1$ and $R^2$ are as defined in formula (I) and P represents a protective group of an amino group.

<46> A pyrazolo[1,5-a]pyridine derivative represented by formula (10) or salt thereof:

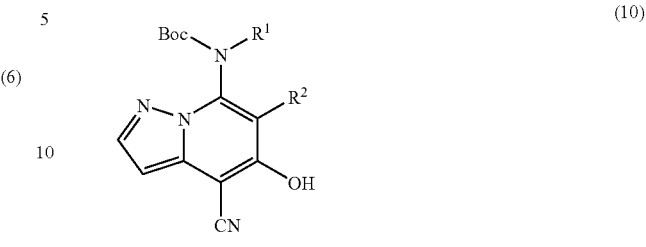
(10)

wherein $R^1$ and $R^2$ are as defined in formula (I) and Boc represents tert-butoxycarbonyl.

<47> A pyrazolo[1,5-a]pyridine derivative represented by formula (11) or salt thereof:

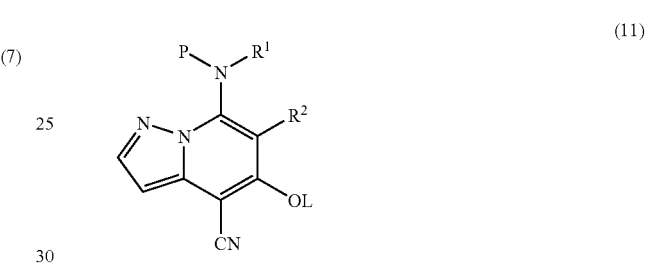
(11)

wherein $R^1$ and $R^2$ are as defined in formula (I), P represents a protective group of an amino group and L represents perfluoroalkylsulfonyl.

<48> A pyrazolo[1,5-a]pyridine derivative represented by formula (12) or salt thereof:

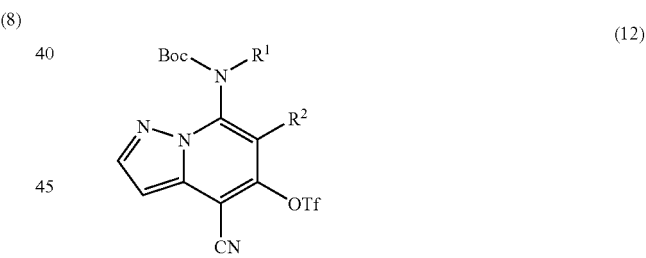
(12)

wherein $R^1$ and $R^2$ are as defined in formula (I), Boc represents tert-butoxycarbonyl and Tf represents trifluoromethanesulfonyl.

<49> A pyrazolo[1,5-a]pyridine derivative represented by formula (13) or salt thereof:

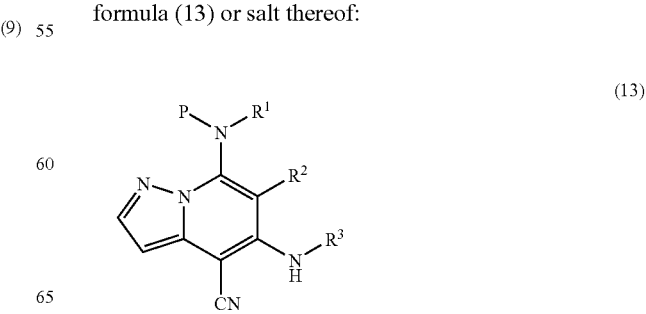
(13)

wherein R¹, R² and R³ are as defined in formula (I) and P represents a protective group of an amino group.

<50> A pyrazolo[1,5-a]pyridine derivative represented by formula (14) or salt thereof:

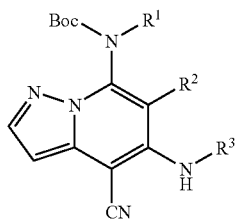

(14)

wherein R¹, R² and R³ are as defined in formula (I) and Boc represents tert-butoxycarbonyl.

<51> The pyrazolo[1,5-a]pyridine derivative represented by any of formulae (8) to (14) or salt thereof according to any of <44> to <50> except a compound wherein R¹ is a C1-C8 alkyl group optionally substituted with —NR$^{1c}$R$^{1d}$, —NR$^{1e}$—CO—R$^{1l}$ or —NR$^{1m}$S(=O)$_2$R$^{1n}$; or a C3-C8 cycloalkyl group optionally substituted with —NR$^{1c}$R$^{1d}$, —NR$^{1e}$—CO—R$^{1l}$ or —NR$^{1m}$S(=O)$_2$R$^{1n}$.

<52> A pharmaceutical composition comprising the pyrazolo [1,5-a]pyridine derivative or pharmaceutically acceptable salt thereof according to any of <1> to <41> and a pharmaceutically acceptable carrier.

<53> A MAPKAP-K2 inhibitor comprising the pyrazolo[1, 5-a]pyridine derivative or pharmaceutically acceptable salt thereof according to any of <1> to <41> as an active ingredient.

<54> A treating or preventing agent comprising the pyrazolo [1,5-a]pyridine derivative or pharmaceutically acceptable salt thereof according to any of <1> to <41> as an active ingredient for neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

<55> The treating or preventing agent according to <54>, wherein the autoimmune disease is rheumatoid arthritis, ankylosing spondylitis, juvenile rheumatoid arthritis, psoriatic arthritis, graft-versus-host disease, diabetes mellitus or Crohn's disease.

BEST MODE FOR CARRYING OUT THE INVENTION

Figure 1:
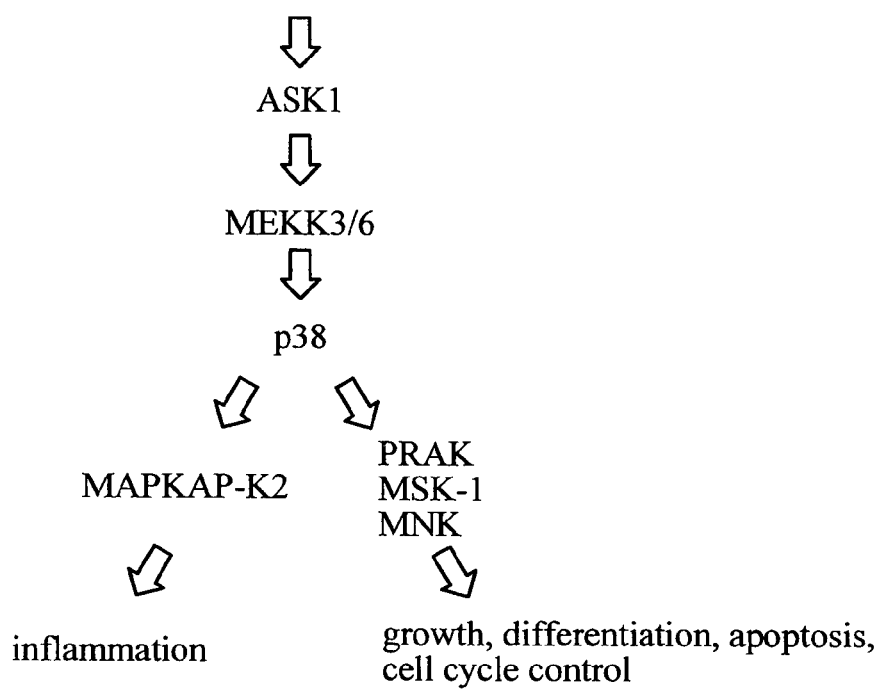
FIG. 1 is a Figure illustrating p38MAPK cascade.

Each compound of the present invention represented by formula (I) is defined as follows:

"C1-C8 Alkyl" in the present description represents either a straight or branched chain alkyl group having 1 to 8 carbon atoms. It includes, not limited thereto, for example, methyl, ethyl, n-propyl, isopropyl, n-butyl, sec-butyl, isobutyl, tert-butyl, n-pentyl, isopentyl, neopentyl, tert-pentyl, 2-methylpentyl, 4-methylpentyl, 3-hexyl, n-hexyl, n-heptyl, 2-methylhexyl, 5-methylhexyl, 2-methyl-2-hexyl, $^6$-methylheptyl, n-octyl and the like. Preferably it is an alkyl group having 1 to 6 carbon atoms. More preferably it is an alkyl group having 1 to 4 carbon atoms, including, not limited thereto, for example, methyl, ethyl, n-propyl, isopropyl, n-butyl, sec-butyl, isobutyl, tert-butyl and the like.

"C2-C8 Alkenyl" in the present description means a straight or branched chain alkenyl group having 2 to 8 carbon atoms. It includes, not limited thereto, for example, vinyl, allyl, 1-propenyl, 2-butenyl, 3-butenyl, 2-methyl-1-propenyl, 4-pentenyl, 5-hexenyl, 4-methyl-3-pentenyl and the like. Preferably it is an alkenyl group having 2 to 6 carbon atoms. More preferably it is an alkenyl group having 2 to 4 carbon atoms, including, for example, vinyl, allyl, isopropenyl, 1-propenyl, 2-butenyl, 1-butenyl, 2-methyl-1-propenyl and the like.

"C2-C8 Alkynyl" in the present description means a straight or branched chain alkynyl group having 2 to 8 carbon atoms. It includes, not limited thereto, for example, ethynyl, propargyl, 3-methylpropargyl, 1-butynyl, 2-butynyl-1-yl, pentynyl, hexynyl and the like. Preferably it is an alkynyl group having 2 to 6 carbon atoms. More preferably it is an alkynyl group having 2 to 4 carbon atom, including, not limited thereto, for example, ethynyl, propargyl, 1-propynyl, 1-butynyl and the like.

"C3-C8 Cycloalkyl group" in the present description means a partially unsaturated or saturated cycloalkyl group having 3 to 8 carbon atoms. It includes, not limited thereto, for example, cyclopropyl, cyclobutyl, cyclopentyl, cyclopentenyl, cyclohexyl, cyclohexenyl, cycloheptyl, cyclooctyl and the like. Preferably, it is an cycloalkyl group having 3 to 6 carbon atoms, including, not limited thereto, for example, cyclopropyl, cyclobutyl, cyclopentyl, cyclohexyl and the like.

"C6-C14 Aryl" in the present description means an aryl group having 6 to 14 carbon atoms which contains one ring or in which an aromatic ring is fused with one or two or more of saturated or unsaturated ring. It includes, not limited thereto, for example, phenyl, naphthyl, anthracenyl, 5-indanyl, 5,6,7, 8-tetrahydro-2-naphthyl and the like. Preferably it is an aryl group having 6 to 10 carbon atoms, including, not limited thereto, for example, phenyl, naphthyl, 5-indanyl and the like. More preferably it is a phenyl group or the like.

"Heteroaryl" in the present description means a heterocyclic group with aromaticity containing 1 to 4 atoms selected from the group consisting of an oxygen atom, a sulfur atom and a nitrogen atom as heteroatoms. It includes, not limited thereto, for example, monovalent groups comprising furan, thiophene, pyrrole, oxazole, thiazole, isothiazole, imidazole, pyrazole, triazole, thiadiazole, oxadiazole, tetrazole, pyridine, pyrazine, pyrimidine, pyridazine, benzofuran, dibenzofuran, benzothiophene, indole, benzimidazole, benzothiazole, benzoxazole, quinoline, isoquinoline, quinazoline, quinoxaline, purine, pteridine, phenoxazine, phenothiazine, acridine, carbazole, cinnoline, dithiazole, indazole, isoindole, isoxazole, naphthyridine, oxathiazole, phthalazine, tetrazine, thiatriazole, triazine and the like. Preferably it is, not limited thereto, for example, a monovalent group comprising furan, thiophene, pyrrole, oxazole, thiazole, isothiazole, imidazole, pyrazole, triazole, pyridine, pyrimidine, pyrazine, pyridazine, benzothiazole, benzoxazole, benzothiophene, benzofuran, indole, indazole, quinoline, phthalazine, quinoxaline, quinazoline, cinnoline, isoindole or the like. More preferably it is, not limited thereto, for example, a monovalent group comprising furan, thiophene, pyrrole, oxazole, thiazole, imidazole, pyrazole, pyridine, pyrimidine, pyrazine, pyridazine, benzothiazole, benzoxazole, benzothiophene, benzofuran, indole, indazole, quinoline, phthalazine, quinoxaline, quinazoline, cinnoline or the like.

"Aliphatic heterocyclic group" in the present description means a partially unsaturated or saturated aliphatic heterocyclic group containing 1 to 4 atoms selected from the group consisting of an oxygen atom, a sulfur atom and a nitrogen atom as heteroatoms. Also, the aliphatic heterocyclic group may contain 1 or 2 of —C(=O)— or —C(=S)— in the ring. An aliphatic heterocyclic group which is fused with an aromatic hydrocarbon or an aromatic heterocycle is also included in the aliphatic heterocyclic group. It includes, not limited thereto, for example, monovalent groups and the like comprising piperidine, pyrrolidine, pyrroline, tetrahydrofuran, dihydropyran, hexahydroazepine, piperazine, quinuclidine, morpholine, thiomorpholine, oxazoline, dioxane, pyran, 2-pyrrolidone, tetrahydro-3H-pyrazol-3-one, 1,2,3,4-tetrahydroisoquinoline, 1,2,3,4-tetrahydroquinoline, 4,5,6,7-tetrahydro-1H-pyrazolo[5,4-c]pyridine, 4,5,6,7-tetrahydro-1H-pyrolo[2,3-c]pyridine, 4,5,6,7-tetrahydrothieno[2,3-c]pyridine, 4,5,6,7-tetrahydro-2H-pyrolo[3,4-c]pyridine, 4,5,6,7-tetrahydrofuro[3,2-c]pyridine, 1,2,3,4-tetrahydro[2,7]naphthyridine, 4,5,6,7-tetrahydrothiazolo[5,4-c]pyridine, 5,6,7,8-tetrahydropyrido[4,3-d]pyrimidine and the like. Preferably, it is, not limited thereto, for example, a monovalent group comprising piperidine, pyrrolidine, pyrroline, tetrahydrofuran, hexahydroazepine, piperazine, morpholine, oxazoline, dioxane, pyran, 1,2,3,4-tetrahydroisoquinoline or the like. More preferably it means a partially unsaturated or saturated aliphatic heterocyclic group containing 1 to 3 heteroatoms at least one of which is a nitrogen atom. Such a group includes, not limited thereto, for example, monovalent groups comprising piperidine, pyrrolidine, pyrroline, hexahydroazepine, piperazine, morpholine, oxazoline and the like. More preferably, it is a monovalent group comprising piperidine, pyrrolidine, hexahydroazepine, piperazine, morpholine or the like.

"Aralkyl" in the present description is a group comprising an aryl group and an alkyl group in combination. It includes, not limited thereto, for example, benzyl, phenethyl, (2-naphthyl)methyl, 3-phenylpropyl, 4-phenylbutyl, 5-(1-naphthyl)pentyl and the like. Preferably it is a group comprising a phenyl or naphthyl group as its aryl moiety and an alkyl group having 1 to 6 carbon atoms in combination. More preferably it is a group comprising a phenyl group as its aryl moiety and an alkyl group having 1 to 4 carbon atoms in combination, including, not limited thereto, for example, benzyl, phenethyl, 3-phenylpropyl, 4-phenylbutyl and the like.

"Heteroarylalkyl" in the present description is a group comprising a heteroaryl group and an alkyl group in combination. Preferably it is a group comprising a 5- to 10-membered monocyclic or bicyclic heteroaryl group having 1 to 3 heteroatoms selected from the group consisting of an oxygen atom, a sulfur atom and a nitrogen atom, and an alkyl group having 1 to 4 carbon atoms in combination. More preferably it is, not limited thereto, for example, 2-furylmethyl, 3-furylmethyl, 2-(2-thienyl)ethyl, 2-(3-thienyl)propyl, 2-methyl-1-(1-pyrrolyl)propyl, 1-(2-pyrrolyl)ethyl or the like.

"Aliphatic heterocyclylalkyl" in the present description is a group comprising an aliphatic heterocycle and an alkyl group in combination. Preferably it is a group comprising a partially unsaturated or saturated aliphatic heterocycle having 1 to 3 atoms selected from the group consisting of an oxygen atom, a sulfur atom and a nitrogen atom as heteroatoms, and an alkyl group having 1 to 4 carbon atoms in combination. More preferably it is, not limited thereto, for example, 3-piperidylmethyl, 3-pyrrolidylmethyl, 2-(4-piperidyl)ethyl, 2-(2-tetrahydrofuryl)propyl, 1-(2-morpholinyl)ethyl, morpholinomethyl, 1-(1-pyrrolidonyl)ethyl or the like.

"C1-C8 Alkoxy" in the present description represents either a straight or branched chain alkoxy group having 1 to 8 carbon atoms. It includes, not limited thereto, for example, methoxy, ethoxy, n-propoxy, isopropoxy, n-butoxy, tert-butoxy, n-pentyloxy, n-hexyloxy n-heptyloxy and the like. Preferably it is an alkoxy group having 1 to 6 carbon atoms. More preferably it is an alkoxy group having 1 to 4 carbon atoms, including, not limited thereto, for example, methoxy, ethoxy, n-propoxy, isopropoxy, n-butoxy, tert-butoxy and the like.

"Alicyclic hydrocarbyloxy" in the present description is a group comprising an cycloalkyl group and an oxy group in combination. It includes, not limited thereto, for example, cyclopropyloxy, cyclobutyloxy, cyclopentyloxy, cyclopentenyloxy, cyclohexyloxy, cyclohexenyloxy, cycloheptyloxy, cyclooctyloxy and the like. Preferably it is an cycloalkyl-oxy group cycloalkyl-oxy group having 3 to 8 carbon atoms. More preferably it is an alkoxy group having 3 to 6 carbon atoms, including, not limited thereto, for example, cyclopropyloxy, cyclobutyloxy, cyclopentyloxy, cyclohexyloxy and the like.

"C1-C6 Alkylthio" in the present description is a group comprising a C1-C6 alkyl and a thio group in combination. It includes, not limited thereto, for example, methylthio, ethylthio, n-propylthio, isopropylthio, n-butylthio, sec-butylthio, isobutylthio, tert-butylthio, n-pentylthio, isopentylthio, neopentylthio, tert-pentylthio, 2-methylpentylthio, 4-methylpentylthio, 3-hexylthio, n-hexylthio, n-heptylthio and the like. Preferably it is an alkylthio group having 1 to 4 carbon atoms. More preferably, it is an alkylthio group having 1 to 3 carbon atoms, including, not limited thereto, for example, methylthio, ethylthio, n-propylthio, isopropylthio and the like.

"C1-C6 Acyl" in the present description is an acyl group comprising an alkyl having 1 to 6 carbon atoms or an alicyclic group having 1 to 6 carbon atoms. Preferably it is, not limited thereto, for example, acetyl, propionyl, butyryl, isobutyryl, valeryl, isovaleryl, pivaloyl or the like.

"C1-C6 Acylamino" in the present description is a group comprising a C1-C6 acyl and an amino group in combination. Preferably it is, not limited thereto, for example, acetylamino, propionylamino, butyrylamino, isobutyrylamino, valerylamino, isovalerylamino, pivaloylamino or the like.

"C2-C7 Alkoxycarbonyl" in the present description is a group comprising a C1-C6 alkoxy and a carbonyl group in combination. Preferably it is, not limited thereto, for example, methoxycarbonyl, ethoxycarbonyl, isopropoxycarbonyl, tert-butoxycarbonyl or the like.

"C7-C12 Phenylalkyl group" in the present description is a group comprising phenyl and a C1-C6 alkyl group in combination. Preferably it is, not limited thereto, for example, benzyl, phenethyl, 2-phenylpropyl, 3-phenylpropyl, 4-phenylbutyl or the like.

"Protective group for an amino group" in the present description is a protective group for an amino group generally used in this field (Reference: Protective Groups in Organic Synthesis, 3rd edition, John Wiley & Sons Inc.). Preferably it is, not limited thereto, for example, tert-butoxycarbonyl, benzyloxycarbonyl, methoxycarbonyl, ethoxycarbonyl, 2,2,2-trichloroethoxycarbonyl, acetyl, trifluoroacetyl, pivaloyl, benzoyl, 2,4,6-trimethylbenzoyl, p-methoxybenzyl, 3,4-dimethoxybenzyl, tert-butyl, methoxymethyl, 2-trimethylsilylethoxymethyl, benzyloxymethyl or the like. More preferably it is, not limited thereto, for example, alkoxycarbonyl such as tert-butoxycarbonyl, benzyloxycarbonyl, methoxycarbonyl, ethoxycarbonyl, 2,2,2-trichloroethoxycarbonyl or the like. Further preferably it is tert-butoxycarbonyl.

"Perfluoroalkylsulfonyl" in the present description is a polyfluorinated alkylsulfonyl group which is generally used for transforming a hydroxyl group to a leaving group in this field. Preferably it is, not limited thereto, for example, trifluoromethanesulfonyl, nonafluorobutanesulfonyl or the like. More preferably, it is trifluoromethanesulfonyl.

"Halogen atom" in the present description means a fluorine atom, a chlorine atom, a bromine atom or an iodine atom. Preferably it is a fluorine atom, a chlorine atom or a bromine atom, and more preferably it is a fluorine atom or a chlorine atom.

"C1-C8 Alkyl group (when two C1-C8 alkyl groups as $R^{1x}$, $R^{2y}$ or $R^{3z}$ bond to one nitrogen atom, they may bond to each other via an oxygen atom, a nitrogen atom, a sulfur atom or a single bond to form a ring)" as $R^{1x}$, $R^{2y}$ or $R^{3z}$ in the present description includes, not limited thereto, for example, 1-pyrrolidinyl, 2-methyl-1-pyrrolidinyl, 1-piperidyl, morpholino, thiomorpholino, piperazino and the like. Preferably it is, not limited thereto, for example, 1-pyrrolidinyl, 1-piperidyl, morpholino, piperazino or the like.

"C1-C8 Alkyl group optionally substituted with oxo group(s)" included in "C1-C8 alkyl group optionally substituted with halogen atom(s), hydroxyl group(s) or oxo group(s)" as the substituent of substituent(s) of $R^1$, $R^2$ or $R^3$ in the present description includes, not limited thereto, for example, an acetyl group, a propionyl group, a butyryl group, an isobutyryl group, a valeryl group, an isovaleryl group, a 2-oxopropyl group, a 3-oxobutyl group, a pivaloyl group and the like. Preferably it is, not limited thereto, for example, an acetyl group, a propionyl group, an isobutyryl group, a valeryl group, an isovaleryl group, a pivaloyl group or the like.

With respect to $R^1$ and $R^2$ in the present description, the case wherein "when $R^1$ or $R^2$ is an optionally substituted C6-C14 aryl group or an optionally substituted heteroaryl group, and two or more substituents of $R^1$ or $R^2$ bond to $R^1$ or $R^2$, these substituents may bond to each other via an oxygen atom, a nitrogen atom, a sulfur atom or a single bond to form a ring" includes, not limited thereto, for example, chromane, indoline, isochromane, isoindoline, 2H,3H-benzo[e]1,4-dioxine, 2H-benzo[d]1,3-dioxolene, 2H,3H,4H-benzo[e]thiine, 2H,3H,4H-benzo[e]1,4-oxazine and the like. Preferably it is, not limited thereto, for example, chromane, indoline, isochromane, isoindoline, 2H,3H-benzo[e]1,4-dioxine, 2H-benzo[d]1,3-dioxolene or the like.

In the above definition, "C" in for example "C1" represents a carbon atom and the subsequent numeral represents the number of carbon atoms. For example, "C1-C6" represents the range of number of carbon atoms from 1 to 6. Needless to say, in the present invention, each group different in number of carbon atoms means the same type of group having each specified number of carbon atoms. For example, "C1-C6 alkyl group" means an alkyl group, which is defined for "C1-C8 alkyl group", having 1 to 6 carbon atoms. The number of carbon atoms in other groups is interpreted in the same way.

$R^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group. Preferably it is an optionally substituted C1-C8 alkyl group, an optionally substituted C2-C8 alkenyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group, an optionally substituted aliphatic heterocyclic group or the like. More preferably it is an optionally substituted C6-C14 aryl group, an optionally substituted heteroaryl group, an optionally substituted C7-C16 aralkyl group, an optionally substituted heteroarylalkyl group or the like. Further preferably it is an optionally substituted C6-C14 aryl group, an optionally substituted heteroaryl group or the like, and even more preferably it is an optionally substituted phenyl group, an optionally substituted heteroaryl group or the like. The optionally substituted heteroaryl group as $R^1$ is preferably a heteroaryl group wherein a monocyclic aryl group and an optionally substituted monocyclic heteroaryl group are fused with each other and the aryl group is bonded to the NH group at the 7-position of the pyrazolo[1,5-a]pyridine derivative represented by formula (I). The monocyclic aryl group is a phenyl group or the like. Preferably the heteroaryl group is, not limited thereto, for example, benzothiazol-4-yl, benzothiazol-5-yl, benzothiazol-6-yl, benzothiazol-7-yl, benzoxazol-4-yl, benzoxazol-5-yl, benzoxazol-6-yl, benzoxazol-7-yl, benzimidazol-4-yl, benzimidazol-5-yl, benzimidazol-6-yl, benzimidazol-7-yl, indazol-4-yl, indazol-5-yl, indazol-6-yl, indazol-7-yl, benzothiophen-4-yl, benzothiophen-5-yl, benzothiophen-6-yl, benzothiophen-7-yl, indol-4-yl, indol-5-yl, indol-6-yl, indol-7-yl or the like. More preferably, it is benzothiazol-5-yl, benzothiazol-6-yl, benzoxazol-5-yl, benzoxazol-6-yl, benzimidazol-5-yl, benzimidazol-6-yl, indazol-5-yl, indazol-6-yl, benzothiophen-5-yl, benzothiophen-6-yl, indol-5-yl, indol-6-yl or the like.

The substituent(s) of $R^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-SR^{1b}$, $-NR^{1c}R^{1d}$, $-C(=O)R^{1e}$, $-S(=O)_2NR^{1f}R^{1g}$, $-C(=O)OR^{1h}$, $-C(=O)NR^{1i}R^{1j}$, $-NR^{1k}C(=O)R^{1l}$, $-NR^{1m}S(=O)_2R^{1n}$ and the like. Preferably it is 1 to 5 substituents selected from the group consisting of a halogen atom, a cyano group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-NR^{1c}R^{1d}$, $-C(=O)R^{1e}$, $-S(=O)_2NR^{1f}R^{1g}$, $-C(=O)OR^{1h}$, $-C(=O)NR^{1i}R^{1j}$, $-NR^{1k}C(=O)R^{1l}$, $-NR^{1m}S(=O)_2R^{1n}$ and the like. More preferably it is 1 to 4 substituents selected from the group consisting of a halogen atom, an optionally substituted C1-C6 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-NR^{1c}R^{1d}$, $-(=O)_2NR^{1f}, R^{1g}$, $-C(=O)OR^{1h}$, $-C(=O)NR^{1i}R^{1j}$, $-NR^{1k}C(=O)R^{1l}$, $-NR^{1m}S(=O)_2R^{1n}$ and the like. Further preferably it is 1 to 3 substituents selected from the group consisting of a halogen atom, an optionally substituted C1-C4 alkyl group, an optionally substituted C3-C6 cycloalkyl group, an optionally substituted aliphatic heterocyclic group, an optionally substituted phenyl group, an optionally substituted heteroaryl group, $-OR^{1a}$, $-NR^{1c}R^{1d}$, $-S(=O)_2NR^{1f}R^{1g}$, $-C(=O)OR^{1h}$, $-C(=O)NR^{1i}R^{1j}$, $-NR^{1k}C(=O)R^{1l}$, $-NR^{1m}S(=O)_2R^{1n}$ and the like.

$R^{1x}$ (x represents a, b, c, d, e, f. g, h, i, j, k, l, m or n) may be identical or different, and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group. Preferably $R^{1x}$ is a hydrogen atom, an optionally substituted C1-C4 alkyl group (when two C1-C4 alkyl groups as $R^{1x}$ bond to one nitrogen atom, they may bond to each other via an oxygen atom, a nitrogen atom, a sulfur atom or a single bond to form a ring), an optionally substituted phenyl group, an optionally substituted heteroaryl group, an optionally substituted C3-C6 cycloalkyl group, an optionally substituted aliphatic heterocyclic group, an optionally substituted phenylalkyl group, an optionally substituted heteroarylalkyl group or an optionally substituted aliphatic heterocyclylalkyl group. More preferably $R^{1x}$ is a hydrogen atom, an optionally substituted C1-C4 alkyl group (when two C1-C4 alkyl groups as $R^{1x}$ bond to one nitrogen atom, they may bond to each other via an oxygen atom, a nitrogen atom, a sulfur atom or a single bond to form a ring), an optionally substituted heteroaryl group, an optionally substituted aliphatic heterocyclic group, an optionally substituted heteroarylalkyl group or an optionally substituted aliphatic heterocyclylalkyl group.

When $R^1$ is an optionally substituted C6-C14 aryl group or an optionally substituted heteroaryl group and two or more substituents of $R^1$ bond to $R^1$, these substituents may bond to each other via an oxygen atom, a nitrogen atom, a sulfur atom or a single bond to form a ring.

$R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group. Preferably it is a hydrogen atom, an optionally substituted C1-C6 alkyl group, an optionally substituted C2-C6 alkenyl group, an optionally substituted C6-C14 aryl group, an optionally substituted heteroaryl group, an optionally substituted C3-C8 cycloalkyl group or the like. More preferably it is a hydrogen atom, an optionally substituted C1-C4 alkyl group, an optionally substituted phenyl group, an optionally substituted heteroaryl group, an optionally substituted C3-C6 cycloalkyl group or the like. Further preferably it is a hydrogen atom, an optionally substituted C1-C4 alkyl group or the like.

The substituent(s) of $R^2$ are one or more substituent(s) selected from the group consisting of a halogen atom, a cyano group, a nitro group, an optionally substituted C1-C8 alkyl group, $-OR^{2a}$, $-SR^{2b}$, $-NR^{2c}R^{2d}$, $-C(=O)R^{2e}$, $-S(=O)_2NR^{2f}R^{2g}$, $-C(=O)OR^{2h}$, $-C(=O)NR^{2i}R^{2j}$, $-NR^{2k}C(=O)R^{2l}$ and $-NR^{1m}S(=O)_2R^{1n}$. Preferably the substituent(s) of $R^2$ are 1 to 5 substituent(s) selected from the group consisting of a halogen atom, a cyano group, an optionally substituted C1-C6 alkyl group, $-OR^{2a}$, $-NR^{2c}R^{2d}$, $-S(=O)_2NR^{2f}R^{2g}$, $-C(=O)OR^{2h}$, $-C(=O)NR^{2i}R^{2j}$, $-NR^{2k}C(=O)R^{2l}$, $-NR^{1m}S(=O)_2R^{1n}$ and the like, more preferably 1 to 3 substituent(s) selected from the group consisting of a halogen atom, an optionally substituted C1-C4 alkyl group, $-OR^{2a}$, $NR^{2c}R^{2d}$, $-C(=O)OR^{2h}$, $-C(=O)NR^{2i}R^{2j}$, $-NR^{2k}C(=O)R^{2l}$ and the like.

$R^2y$ (y represents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group. Preferably $R^{2y}$ is a hydrogen atom, an optionally substituted C1-C4 alkyl group (when two C1-C4 alkyl groups as $R^{2y}$ bond to one nitrogen atom, they may bond to each other via an oxygen atom, a nitrogen atom, a sulfur atom or a single bond to form a ring), an optionally substituted phenyl group, an optionally substituted heteroaryl group, an optionally substituted C3-C6 cycloalkyl group, an optionally substituted aliphatic heterocyclic group, an optionally substituted phenylalkyl group, an optionally substituted heteroarylalkyl group or the like. More preferably $R^{2y}$ is a hydrogen atom, an optionally substituted C1-C4 alkyl group (when two C1-C4 alkyl groups as $R^{2y}$ bond to one nitrogen atom, they may bond to each other via an oxygen atom, a nitrogen atom, a sulfur atom or a single bond to form a ring), an optionally substituted heteroaryl group, an optionally substituted aliphatic heterocyclic group, an optionally substituted heteroarylalkyl group or the like.

When $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring.

$R^3$ represents an optionally substituted C1-C8 alkyl group, an optionally substituted C3-C8 cycloalkyl group or an optionally substituted aliphatic heterocyclic group. Preferably it is an optionally substituted C3-C6 cycloalkyl group, an optionally substituted aliphatic heterocyclic group or the like. More preferably it is a C3-C8 cycloalkyl group substituted with an optionally substituted amino group, an optionally substituted aliphatic heterocyclic group having 1 to 4 nitrogen atoms as heteroatoms or the like.

The substituent(s) of $R^3$ are one or more substituent(s) selected from the group consisting of a halogen atom, a cyano group, a nitro group, $-OR^{3a}$, $-SR^{3b}$, $-NR^{3c}R^{3d}$, an optionally substituted C1-C8 alkyl group, an optionally substituted C3-C8 cycloalkyl group and an optionally substituted aliphatic heterocyclic group.

When $R^3$ is an optionally substituted C1-C8 alkyl group, preferred substituents of $R^3$ are 1 to 3 substituent(s) selected from the group consisting of $-OR^{3a}$, $-NR^{3c}R^{3d}$, a C3-C8 cycloalkyl group optionally substituted with an optionally substituted amino group and an optionally substituted aliphatic heterocyclic group. Further, in addition to these substituents, $R^3$ may be substituted with 1 to 5 substituent(s) selected from the group consisting of a halogen atom, a cyano group, an optionally substituted C1-C6 alkyl group and the like. More preferred substituents of $R^3$ in the case wherein $R^3$ is an optionally substituted C1-C8 alkyl group are 1 to 2 substituent(s) selected from the group consisting of $-OR^{3a}$, $-NR^{3c}R^{3d}$, a C5-C6 cycloalkyl group optionally substituted with an amino group and an optionally substituted aliphatic heterocyclic group containing 1 to 2 nitrogen atom(s). Here, in addition to these substituents, $R^3$ may be further substituted with 1 to 4 substituent(s) selected from the group consisting of a fluorine atom, a cyano group, an optionally substituted C1-C4 alkyl group and the like.

When $R^3$ is an optionally substituted C3-C8 cycloalkyl group, preferred substituents of $R^3$ are 1 to 3 substituent(s) selected from the group consisting of $-OR^{3a}$, $-NR^{3c}R^{3d}$, a C1-C6 alkyl group substituted with an optionally substituted amino group and an optionally substituted aliphatic heterocyclic group. Further, in addition to these substituents, $R^3$ may be substituted with 1 to 5 substituent(s) selected from the group consisting of a halogen atom, a cyano group, an optionally substituted C1-C6 alkyl group and the like. More preferred substituents of $R^3$ are, in the case wherein $R^3$ is an optionally substituted C3-C8 aliphatic hydrocarbon group, 1 to 2 substituent(s) selected from the group consisting of —$OR^{3a}$, —$NR^{3c}R^{3d}$, a C1-C6 alkyl group optionally substituted with an amino group and an optionally substituted aliphatic heterocyclic group containing 1 to 2 nitrogen atom(s). Here, in addition to these substituents, $R^3$ may be further substituted with 1 to 4 substituent(s) selected from the group consisting of a fluorine atom, a cyano group, an optionally substituted C1-C4 alkyl group and the like.

When $R^3$ is an optionally substituted aliphatic heterocyclic group, preferred substituents of $R^3$ are 1 to 5 substituent(s) selected from the group consisting of —$OR^{3a}$, —$NR^{3c}R^{3d}$, a halogen atom, a cyano group, an optionally substituted C1-C6 alkyl group, an optionally substituted C3-C8 cycloalkyl group, an optionally substituted aliphatic heterocyclic group and the like. More preferred substituents of $R^3$ in the case wherein $R^3$ is an optionally substituted aliphatic heterocyclic group are 1 to 4 substituent(s) selected from the group consisting of —$OR^{3a}$, —$NR^{3c}R^{3d}$, a fluorine atom, a cyano group, an optionally substituted C1-C4 alkyl group, an optionally substituted C3-C6 cycloalkyl group, an optionally substituted aliphatic heterocyclic group and the like.

$R^{3z}$ (z represents a, b, c or d) may be identical or different and represents a hydrogen atom, an optionally substituted C1-C8 alkyl group (when two C1-C8 alkyl groups as $R^{3z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group. Preferably $R^{3z}$ is a hydrogen atom, an optionally substituted C1-C4 alkyl group (when two C1-C4 alkyl groups as $R^{3z}$ bond to one nitrogen atom, they may bond to each other via an oxygen atom, a nitrogen atom, a sulfur atom or a single bond to form a ring), an optionally substituted phenyl group, an optionally substituted heteroaryl group, an optionally substituted C3-C6 cycloalkyl group, an optionally substituted aliphatic heterocyclic group, an optionally substituted phenylalkyl group, an optionally substituted heteroarylalkyl group or the like. More preferably $R^{3z}$ is a hydrogen atom, an optionally substituted C1-C4 alkyl group (when two C1-C4 alkyl groups as $R^{3z}$ bond to one nitrogen atom, they may bond to each other via an oxygen atom, a nitrogen atom, a sulfur atom or a single bond to form a ring), an optionally substituted heteroaryl group, an optionally substituted aliphatic heterocyclic group, an optionally substituted heteroarylalkyl group or the like.

The substituent(s) of substituent(s) of $R^1$, $R^2$ or $R^3$ are, unless specifically defined, one or more substituent(s) selected from the group consisting of a halogen atom; a hydroxyl group; a cyano group; a nitro group; an amino group; a C1-C8 alkyl group optionally substituted with one or more substituent(s) selected from the group consisting of 1 to 9 halogen atom(s), 1 to 2 hydroxyl group(s), 1 to 2 cyano group(s) and 1 to 2 oxo group(s); a C3-C8 cycloalkyl group optionally substituted with one or more substituent(s) selected from the group consisting of 1 to 4 methyl group(s), 1 to 9 halogen atom(s), 1 to 2 hydroxyl group(s),1 to 2 cyano group(s) and 1 to 2 oxo group(s); a C1-C8 alkoxy group optionally substituted with one or more substituent(s) selected from the group consisting of 1 to 9 halogen atom(s), 1 to 2 hydroxyl group(s) and 1 to 2 cyano group(s); a C3-C8 cycloalkyl-oxy group cycloalkyl-oxy group optionally substituted with one or more substituent(s) selected from the group consisting of 1 to 2 methyl group(s), 1 to 9 halogen atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 8 halogen atom(s), 1 to 2 hydroxyl group(s) and 1 to 2 cyano group(s); a C6-C14 aryl group optionally substituted with one or more substituent(s) selected from the group consisting of 1 to 4 methyl group(s), 1 to 5 halogen atom(s), 1 to 2 hydroxyl group(s) and 1 to 2 cyano group(s); and a heteroaryl group optionally substituted with one or more substituent(s) selected from the group consisting of 1 to 4 methyl group(s), 1 to 5 halogen atom(s), 1 to 2 hydroxyl group(s) and 1 to 2 cyano group(s).

Preferably the substituent(s) of substituent(s) of $R^1$ are one or more substituent(s) selected from the group consisting of a halogen atom; a hydroxyl group; an amino group; a C1-C6 alkyl group optionally substituted with one or more substituent(s) selected from the group consisting of 1 to 7 fluorine atom(s), 1 to 2 hydroxyl group(s), 1 to 2 cyano group(s) and 1 to 2 oxo group(s); a C3-C8 cycloalkyl group optionally substituted with one or more substituent(s) selected from the group consisting of 1 to 4 methyl group(s), 1 to 7 fluorine atom(s), 1 to 2 hydroxyl group(s), 1 to 2 cyano group(s) and 1 to 2 oxo group(s); a C1-C6 alkoxy group optionally substituted with one or more substituent(s) selected from the group consisting of 1 to 7 fluorine atom(s), 1 to 2 hydroxyl group(s) and 1 to 2 cyano group(s); a C3-C8 cycloalkyl-oxy group cycloalkyl-oxy group optionally substituted with one or more substituent(s) selected from the group consisting of 1 to 4 methyl group(s), 1 to 7 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 fluorine atom(s), 1 to 2 hydroxyl group(s) and 1 to 2 cyano group(s); a C6-C14 aryl group optionally substituted with one or more substituent(s) selected from the group consisting of 1 to 4 methyl group(s), 1 to 5 halogen atom(s), 1 to 2 hydroxyl group(s) and 1 to 2 cyano group(s); a heteroaryl group optionally substituted with one or more substituent(s) selected from the group consisting of 1 to 4 methyl group(s), 1 to 5 halogen atom(s), 1 to 2 hydroxyl group(s) and 1 to 2 cyano group(s); and the like. When halogen atom(s) are included as the substituent(s) of substituent(s) of $R^1$, the number of the substituents is preferably 1 to 8. When the substituent(s) of substituent(s) of $R^1$ are selected only from the substituents other than halogen atoms, the number of the substituents is preferably 1 to 3. More preferred substituent(s) of substituent(s) of $R^1$ are one or more substituent(s) selected from the group consisting of halogen atom; a hydroxyl group; an amino group; a C1-C4 alkyl group optionally substituted with one or more substituent(s) selected from the group consisting of 1 to 5 fluorine atom(s), 1 to 2 hydroxyl group(s), 1 to 2 cyano group(s) and 1 to 2 oxo group(s); a C3-C6 cycloalkyl group optionally substituted with one or more substituent(s) selected from the group consisting of 1 to 4 methyl group(s), 1 to 7 fluorine atom(s), 1 to 2 hydroxyl group(s), 1 to 2 cyano group(s) and 1 to 2 oxo group(s); a C1-C4 alkoxy group optionally substituted with one or more substituent(s) selected from the group consisting of 1 to 7 fluorine atom(s), 1 to 2 hydroxyl group(s) and 1 to 2 cyano group(s); a C3-C6 cycloalkyl-oxy groupcycloalkyl-oxy group optionally substituted with one or more substituent(s) selected from the group consisting of 1 to 4 methyl group(s), 1 to 7 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 fluorine atom(s), 1 to 2 hydroxyl group(s) and 1 to 2 cyano group(s); and the like. Here, when halogen atom(s) are included as the substituent(s) of substituent(s) of $R^1$, the number of the substituents is preferably 1 to 6, while when the substituent(s) of substituent(s) of $R^1$ are selected only from the substituents other than halogen atoms, the number of the substituents is preferably 1 to 2.

Preferably the substituent(s) of substituent(s) of $R^2$ are one or more substituent(s) selected from the group consisting of a halogen atom; a hydroxyl group; a cyano group; a nitro group; an amino group; a C1-C6 alkyl group optionally substituted with one or more substituent(s) selected from the group consisting of 1 to 9 fluorine atom(s), 1 to 2 hydroxyl group(s), 1 to 2 cyano group(s) and 1 to 2 oxo group(s); a C3-C8 cycloalkyl group optionally substituted with one or more substituent(s) selected from the group consisting of 1 to 4 methyl group(s), 1 to 9 fluorine atom(s), 1 to 2 hydroxyl group(s), 1 to 2 cyano group(s) and 1 to 2 oxo group(s); a C1-C6 alkoxy group optionally substituted with one or more substituent(s) selected from the group consisting of 1 to 9 fluorine atom(s), 1 to 2 hydroxyl group(s) and 1 to 2 cyano group(s); a C3-C8 cycloalkyl-oxy group cycloalkyl-oxy group optionally substituted with one or more substituent(s) selected from the group consisting of 1 to 4 methyl group(s), 1 to 9 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 halogen atom(s), 1 to 2 hydroxyl group(s) and 1 to 2 cyano group(s); and the like. When halogen atom(s) are included as the substituent(s) of substituent(s) of $R^2$, the number of the substituents is preferably 1 to 8. When the substituent(s) of substituent(s) of $R^2$ are selected only from the substituents other than halogen atoms, the number of the substituents is preferably 1 to 3. More preferably, the substituent(s) of substituent(s) of $R^2$ are one or more substituent(s) selected from the group consisting of a halogen atom; a hydroxyl group; a cyano group; a nitro group; an amino group; a C1-C4 alkyl group optionally substituted with one or more substituent(s) selected from the group consisting of 1 to 7 fluorine atom(s), 1 to 2 hydroxyl group(s), 1 to 2 cyano group(s) and 1 to 2 oxo group(s); a C3-C6 cycloalkyl group optionally substituted with one or more substituent(s) selected from the group consisting of 1 to 4 methyl group(s), 1 to 7 fluorine atom(s), 1 to 2 hydroxyl group(s), 1 to 2 cyano group(s) and 1 to 2 oxo group(s); a C1-C4 alkoxy group optionally substituted with one or more substituent(s) selected from the group consisting of 1 to 7 fluorine atom(s), 1 to 2 hydroxyl group(s) and 1 to 2 cyano group(s); a C3-C6 cycloalkyl-oxy groupcycloalkyl-oxy group optionally substituted with one or more substituent(s) selected from the group consisting of 1 to 4 methyl group(s), 1 to 7 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 halogen atom(s), 1 to 2 hydroxyl group(s) and 1 to 2 cyano group(s); and the like. Here, when halogen atom(s) are included as the substituent(s) of substituent(s) of $R^2$, the number of the substituents is preferably 1 to 8, while when the substituent(s) of substituent(s) of $R^2$ are selected only from the substituents other than halogen atoms, the number of the substituents is preferably 1 to 3. Further preferably, the substituent(s) of substituent(s) of $R^2$ are one or more substituent(s) selected from the group consisting of 1 to 5 halogen atom(s); 1 to 2 hydroxyl group(s); 1 to 2 cyano group(s); 1 to 2 amino group(s); a C1-C4 alkyl group optionally substituted with one or more substituent(s) selected from the group consisting of 1 to 5 fluorine atom(s), 1 to 2 hydroxyl group(s), 1 to 2 cyano group(s) and 1 to 2 oxo group(s); a C1-C4 alkoxy group optionally substituted with one or more substituent(s) selected from the group consisting of 1 to 5 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 halogen atom(s), 1 to 2 hydroxyl group(s) and 1 to 2 cyano group(s); and the like. Here, when halogen atom(s) are included as the substituent(s) of substituent(s) of $R^2$, the number of the substituents is preferably 1 to 6, while when the substituent(s) of substituent(s) of $R^2$ are selected only from the substituents other than halogen atoms, the number of the substituents is preferably 1 to 2.

Preferably the substituent(s) of substituent(s) of $R^3$ are one or more substituent(s) selected from the group consisting of a halogen atom; a hydroxyl group; an amino group; a C1-C6 alkyl group optionally substituted with one or more substituent(s) selected from the group consisting of 1 to 9 fluorine atom(s), 1 to 2 hydroxyl group(s), 1 to 2 cyano group(s) and 1 to 2 oxo group(s); a C3-C8 cycloalkyl group optionally substituted with one or more substituent(s) selected from the group consisting of 1 to 4 methyl group(s), 1 to 9 fluorine atom(s), 1 to 2 hydroxyl group(s), 1 to 2 cyano group(s) and 1 to 2 oxo group(s); a C1-C6 alkoxy group optionally substituted with one or more substituent(s) selected from the group consisting of 1 to 9 fluorine atom(s), 1 to 2 hydroxyl group(s) and 1 to 2 cyano group(s); a C3-C8 cycloalkyl-oxy groupcycloalkyl-oxy group optionally substituted with one or more substituent(s) selected from the group consisting of 1 to 4 methyl group(s), 1 to 9 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 fluorine atom(s), 1 to 2 hydroxyl group(s) and 1 to 2 cyano group(s); a C6-C14 aryl group optionally substituted with one or more substituent(s) selected from the group consisting of 1 to 2 methyl group(s), 1 to 5 fluorine atom(s), 1 to 2 hydroxyl group(s) and 1 to 2 cyano group(s); a heteroaryl group optionally substituted with one or more substituent(s) selected from the group consisting of 1 to 4 methyl group(s), 1 to 5 fluorine atom(s), 1 to 2 hydroxyl group(s) and 1 to 2 cyano group(s); and the like. When halogen atom(s) are included as the substituent(s) of substituent(s) of $R^3$, the number of the substituents is preferably 1 to 8. When the substituent(s) of substituent(s) of $R^3$ are selected only from the substituents other than halogen atoms, the number of the substituents is preferably 1 to 3. More preferably, the substituent(s) of substituent(s) of R3 are one or more substituent(s) selected from the group consisting of a halogen atom; a hydroxyl group; an amino group; a C1-C4 alkyl group optionally substituted with one or more substituent(s) selected from the group consisting of 1 to 7 fluorine atom(s), 1 to 2 hydroxyl group(s), 1 to 2 cyano group(s) and 1 to 2 oxo group(s); a C3-C6 cycloalkyl group optionally substituted with one or more substituent(s) selected from the group consisting of 1 to 4 methyl group(s), 1 to 7 fluorine atom(s), 1 to 2 hydroxyl group(s), 1 to 2 cyano group(s) and 1 to 2 oxo group(s); a C1-C4 alkoxy group optionally substituted with one or more substituent(s) selected from the group consisting of 1 to 7 fluorine atom(s), 1 to 2 hydroxyl group(s) and 1 to 2 cyano group(s); a C3-C6 cycloalkyl-oxy groupcycloalkyl-oxy group optionally substituted with one or more substituent(s) selected from the group consisting of 1 to 4 methyl group(s), 1 to 7 fluorine atom(s), 1 to 2 hydroxyl group(s) and 1 to 2 cyano group(s); a aliphatic heterocyclic group optionally substituted with one or more substituent(s) selected from the group consisting of 1 to 4 methyl group(s), 1 to 6 fluorine atom(s) and 1 to 2 hydroxyl group(s); a phenyl group optionally substituted with one or more substituent(s) selected from the group consisting of 1 to 4 methyl group(s), 1 to 5 fluorine atom(s) and 1 to 2 hydroxyl group(s); a heteroaryl group optionally substituted with one or more substituent(s) selected from the group consisting of 1 to 4 methyl group(s), 1 to 5 fluorine atom(s) and 1 to 2 hydroxyl group(s); and the like. Here, when halogen atom(s) are included as the substituent(s) of substituent(s) of $R^3$, the number of the substituents is preferably 1 to 8, while when the substituent(s) of substituent(s) of $R^3$ are selected only from the substituents other than halogen atoms, the number of the substituents is preferably 1 to 3. Further preferably, the substituent(s) of substituent(s) of $R^3$ are one or more substituent(s) selected from the group consisting of a halogen atom; a hydroxyl group; an amino group; a C1-C4 alkyl group optionally substituted with one or more substituent(s) selected from the group consisting of 1 to 5 fluorine atom(s), 1 to 2 hydroxyl group(s), 1 to 2 cyano group(s) and 1 to 2 oxo group(s); a C1-C4 alkoxy group optionally substituted with one or more substituent(s) selected from the group consisting of 1 to 5 fluorine atom(s), 1 to 2 hydroxyl group(s) and 1 to 2 cyano group(s); an aliphatic heterocyclic group optionally substituted with one or more substituent(s) selected from the group consisting of 1 to 4 methyl group(s), 1 to 6 fluorine atom(s) and 1 to 2 hydroxyl group(s); a heteroaryl group optionally substituted with one or more substituent(s) selected from the group consisting of 1 to 4 methyl group(s), 1 to 5 fluorine atom(s) and 1 to 2 hydroxyl group(s); and the like. Here, when halogen atom(s) are included as the substituent(s) of substituent(s) of $R^3$, the number of the substituents is preferably 1 to 6, while, when the substituent(s) of substituent(s) of $R^3$ are selected only from the substituents other than halogen atoms, the number of the substituents is preferably 1 to 2.

Preferred compounds for the pyrazolo[1,5-a]pyridine derivative represented by formula (I) are a compound comprising a combination of group(s) defined above for $R^1$ to $R^3$ and preferred group(s) described above for $R^1$ to $R^3$; a compound comprising a combination of preferred group(s) described above for $R^1$ to $R^3$; and the like.

The compound of the present invention may contain an acidic group(s) in the molecule. In this case, it may be converted to a pharmaceutically acceptable salt if necessary. As such salts, there may be mentioned salts with non-toxic cations. For example, there may be mentioned salts with alkali metal ions such as $Na^+$ and $K^+$, alkaline earth metal ions such as $Mg^{2+}$ and $Ca^{2+}$, metal ions such as $Al^{3+}$ and $Zn^{2+}$, and organic bases such as ammonia, triethylamine, ethylenediamine, propanediamine, pyrrolidine, piperidine, piperazine, pyridine, lysine, choline, ethanolamine, N,N-dimethylethanolamine, 4-hydroxypiperidine, glucosamine and N-methylglucamine.

The compound of the present invention may contain one or more chiral carbon atoms, and in this case it includes optically active forms and racemic forms. When the compound of the present invention exists in trans form and cis form, it includes the trans form and the cis form.

As examples of compound represented by formula (I) of the present invention, there may be mentioned compounds listed in the following Table A.

TABLE A

| Compound No. | $R^1$ | $R^2$ | $R^3$ |
|---|---|---|---|
| A-1 | 4-(ethoxymethoxy)phenyl | CH3 | piperidin-3-yl |
| A-2 | 4-(ethoxymethoxy)phenyl | CH2=CH-CH2- | piperidin-3-yl |
| A-3 | 3-fluoro-4-(ethoxymethoxy)phenyl | phenyl | pyrrolidin-3-yl |
| A-4 | 3-chloro-4-(ethoxymethoxy)phenyl | thiophen-2-yl | azepan-3-yl |

TABLE A-continued

| Compound No. | R¹ | R² | R³ |
|---|---|---|---|
| A-5 | 2-ethoxy-5-cyanophenyl | 1H-pyrrol-2-yl | piperidin-3-yl |
| A-6 | 4-ethoxyphenyl | 1H-pyrazol-3-yl | piperidin-3-yl |
| A-7 | 4-(pentafluoroethoxy)phenyl | cyclopropyl | azepan-4-yl |
| A-8 | phenyl | 3-hydroxypropyl | piperidin-3-yl |
| A-9 | 4-propoxyphenyl | 2-chlorophenyl | piperidin-4-yl |
| A-10 | 4-isopropoxyphenyl | 3-methoxyphenyl | piperidin-3-yl |
| A-11 | 4-isopropoxy-3-fluorophenyl | 4-(2-methoxyethoxy)phenyl | 2-amino-1,1-dimethylethyl |
| A-12 | 4-methoxyphenyl | 4-fluorobenzothiophen-6-yl | 4-hydroxycyclohexyl |
| A-13 | biphenyl-4-yl | methyl | pyrrolidin-3-yl |

TABLE A-continued
| Compound No. | R¹ | R² | R³ |
|---|---|---|---|
| A-14 | 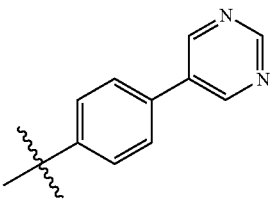 | 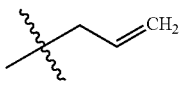 | 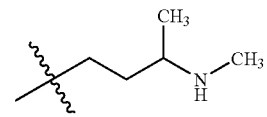 |
| A-15 | 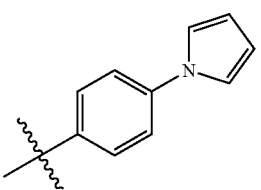 | 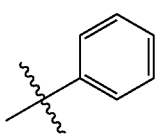 | 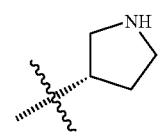 |
| A-16 | 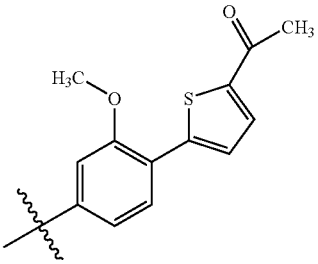 | 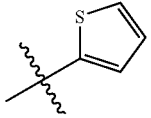 | 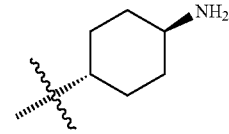 |
| A-17 | 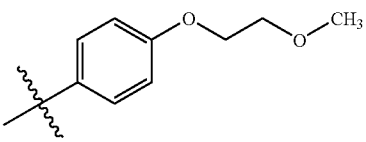 | 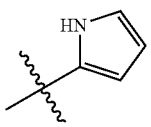 | 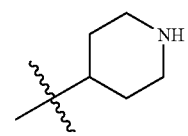 |
| A-18 | 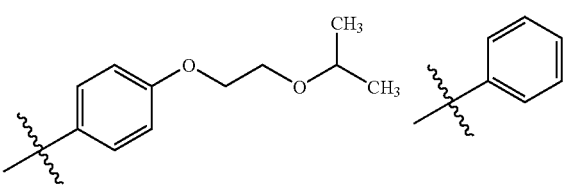 | 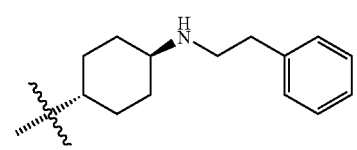 | 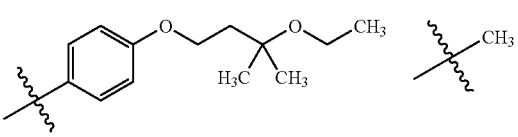 |
| A-19 | 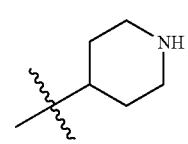 | 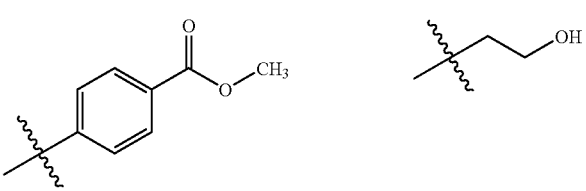 | 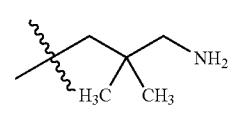 |
| A-20 |  |  |  |

TABLE A-continued
| Compound No. | R¹ | R² | R³ |
|---|---|---|---|
| A-21 | 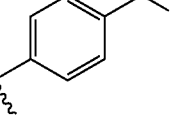 | 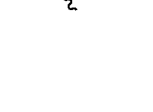 |  |
| A-22 | 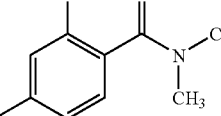 | 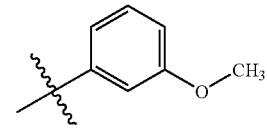 | 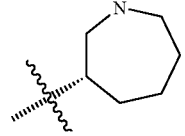 |
| A-23 | 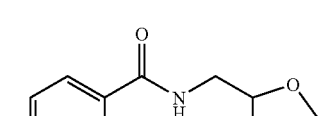 | 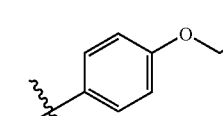 | 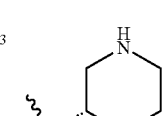 |
| A-24 | 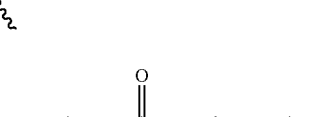 | 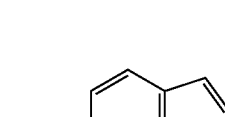 | 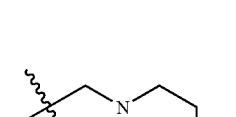 |
| A-25 | 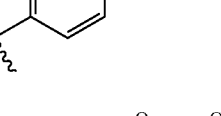 |  |  |
| A-26 | 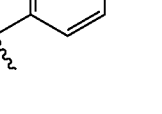 | 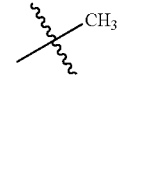 | 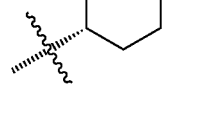 |
| A-27 | 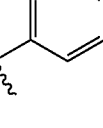 |  | 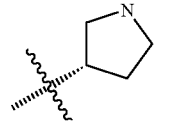 |
| A-28 | 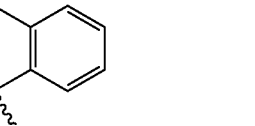 | 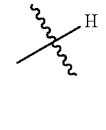 | 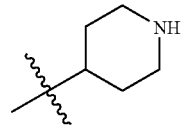 |

TABLE A-continued
| Compound No. | R¹ | R² | R³ |
|---|---|---|---|
| A-29 | 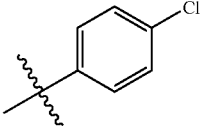 |  | 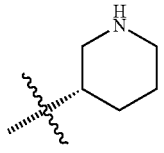 |
| A-30 | 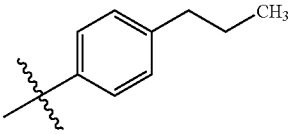 |  | 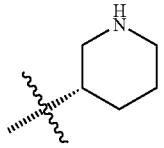 |
| A-31 | 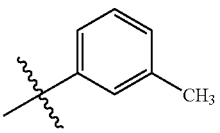 | 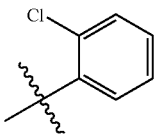 | 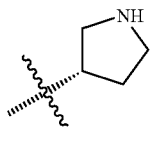 |
| A-32 | 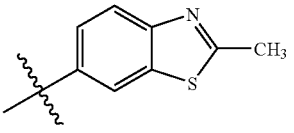 |  | 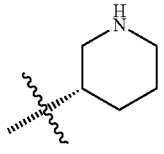 |
| A-33 | 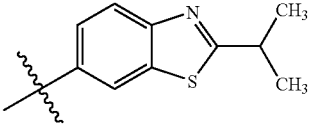 | 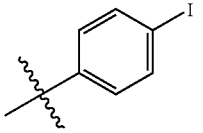 | 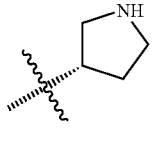 |
| A-34 | 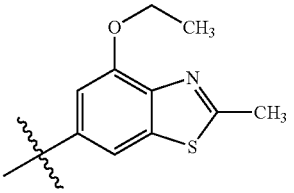 | 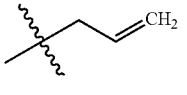 | 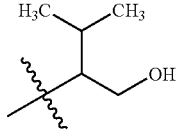 |
| A-35 | 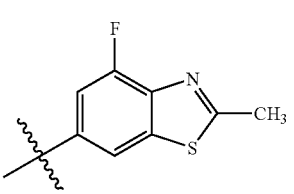 | 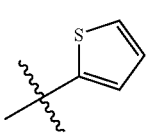 | 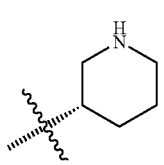 |
| A-36 | 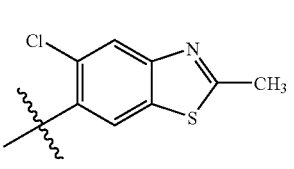 | 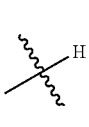 | 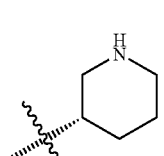 |
| A-37 | 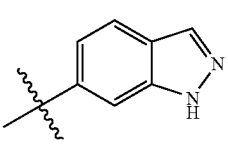 | 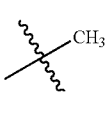 | 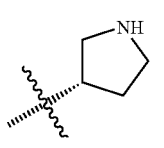 |

TABLE A-continued

| Compound No. | R¹ | R² | R³ |
|---|---|---|---|
| A-38 | 7-chloro-1H-indazol-6-yl | H | piperidin-3-ylmethyl |
| A-39 | 4-methyl-1H-indazol-6-yl | 3-fluorophenyl | (3)-pyrrolidin-3-yl |
| A-40 | 5-fluoro-1-methyl-1H-indazol-6-yl | 2,4-dimethylthiophen-5-yl | piperidin-4-yl |
| A-41 | 2,3-dimethylbenzo[b]thiophen-5-yl | 1-methyl-1H-pyrrol-2-yl | 3-amino-2,2-dimethylpropyl |
| A-42 | benzo[b]thiophen-5-yl | 3-methyl-1H-pyrazol-5-yl | piperidin-3-yl |
| A-43 | benzo[b]thiophen-6-yl | cyclopropyl | (3)-pyrrolidin-3-yl |
| A-44 | 4-(N-methylcarbamoyl)benzo[b]thiophen-6-yl | 3-hydroxypropyl | trans-4-aminocyclohexyl |
| A-45 | 3-(trifluoromethyl)benzo[b]thiophen-6-yl | 2-chloro-3-methoxyphenyl | (3)-pyrrolidin-3-yl |

TABLE A-continued
| Compound No. | R¹ | R² | R³ |
|---|---|---|---|
| A-46 | 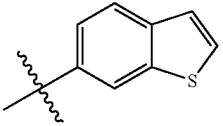 | 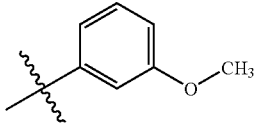 | 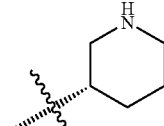 |
| A-47 | 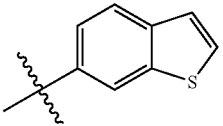 | 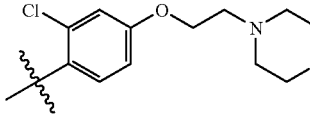 | 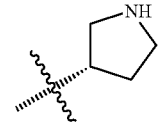 |
| A-48 | 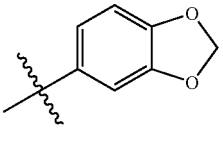 | 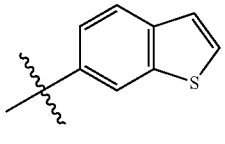 | 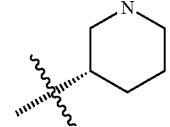 |
| A-49 | 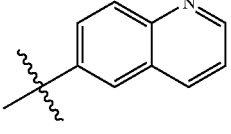 | 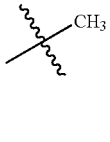 | 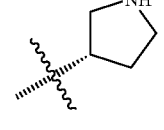 |
| A-50 | 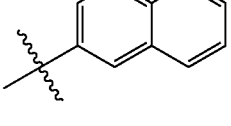 | 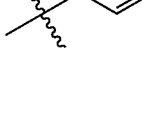 | 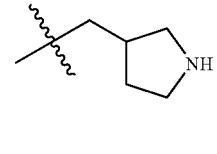 |
| A-51 | 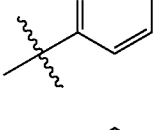 | 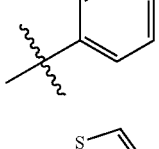 | 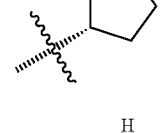 |
| A-52 | 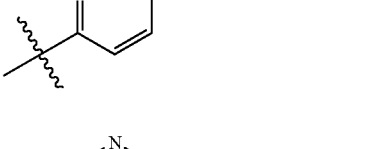 | 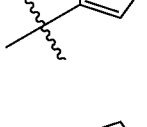 | 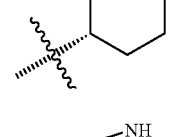 |
| A-53 | 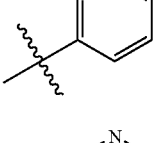 | 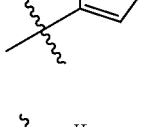 | 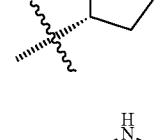 |
| A-54 | 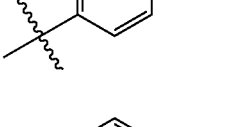 |  | 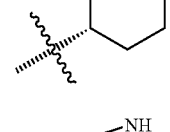 |
| A-55 | 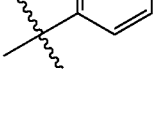 |  | 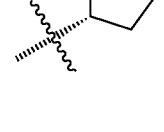 |

TABLE A-continued

| Compound No. | R¹ | R² | R³ |
|---|---|---|---|
| A-56 | 5-chloro-2-isobutoxypyridin-4-yl | 3-hydroxypropyl | (3)-piperidinyl |
| A-57 | 2-ethoxy-3-methylpyridin-4-yl | 2-chlorophenyl | (3)-pyrrolidinyl |
| A-58 | 3-methoxyphenyl | 3-methoxyphenyl | piperidin-3-ylmethyl |
| A-59 | 4-bromo-3-methoxyphenyl | H | (3)-pyrrolidinyl |
| A-60 | 3-methoxyphenyl | benzo[b]thiophen-6-yl | (3)-piperidinyl |
| A-61 | 3-(2-(4-cyanocyclohexyloxy)ethoxy)phenyl | CH₃ | (3)-pyrrolidinyl |
| A-62 | 3-(2-(4-methylpiperazin-1-yl)propoxy)phenyl | propyl | 1-methylpiperidin-3-yl |
| A-63 | 3-(methoxymethoxy)phenyl | CH₃ | (4-methylpiperazin-1-yl)methyl |
| A-64 | 3-(methoxymethyl)phenyl | ethyl | (3)-pyrrolidinyl |

TABLE A-continued

| Compound No. | R¹ | R² | R³ |
|---|---|---|---|
| A-65 | ethyl 3-benzoate | CH₃ (tert-butyl) | 1-methylpyrrolidin-3-yl |
| A-66 | 3-(N-methylcarbamoyl)phenyl | 4-methylpent-3-en-2-yl | pyrrolidin-3-yl (NH) |
| A-67 | 5-[N-(4-fluorophenyl)carbamoyl]-2-methoxyphenyl | 2-cyanophenyl | 4-methylpiperazin-1-yl |
| A-68 | 3-[N-(furan-2-ylmethyl)carbamoyl]phenyl | sec-butyl | 3-aminopropyl |
| A-69 | 3-[N-ethyl-N-methylcarbamoyl]phenyl | 1H-pyrrol-2-yl | pyrrolidin-3-yl (NH) |
| A-70 | 3-(pyridin-3-yl)phenyl | 1H-pyrazol-3-yl | 1-benzylpyrrolidin-3-yl |
| A-71 | 4'-methoxybiphenyl-3-yl | cyclopropyl | 2-(dimethylamino)ethyl |
| A-72 | 3'-amino-2-fluoro-4-methylbiphenyl-5-yl | 3-cyanopropyl | 1-benzylpyrrolidin-3-yl |

TABLE A-continued
| Compound No. | R¹ | R² | R³ |
|---|---|---|---|
| A-73 | 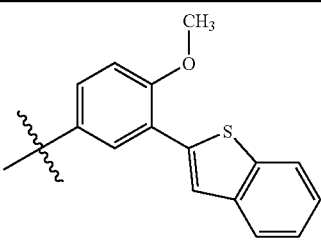 |  H | 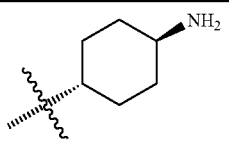 NH₂ |
| A-74 | 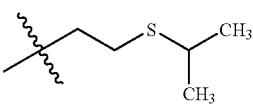 | 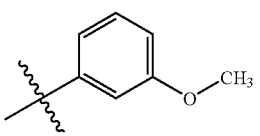 | 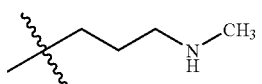 |
| A-75 | 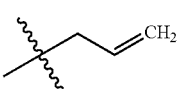 | 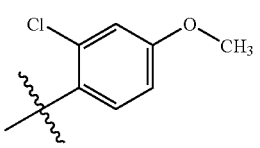 | 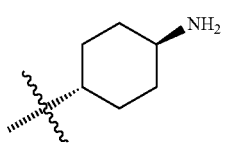 NH₂ |
| A-76 | 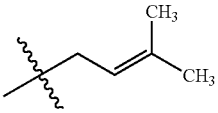 | 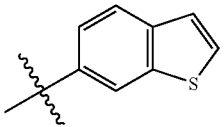 | 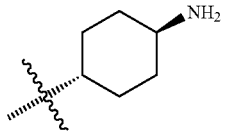 NH₂ |
| A-77 | 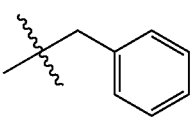 | 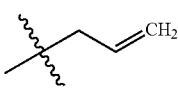 | 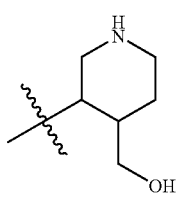 |
| A-78 | 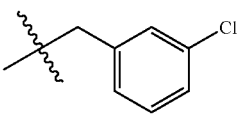 | 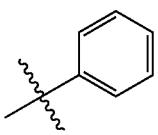 | 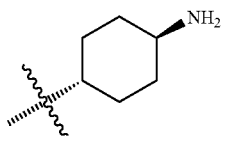 NH₂ |
| A-79 | 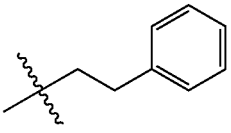 | 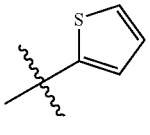 | 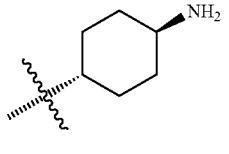 NH₂ |
| A-80 | 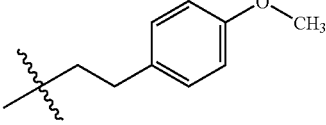 | 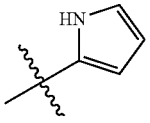 | 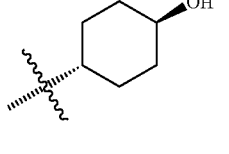 OH |
| A-81 | 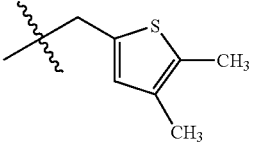 | 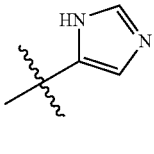 | 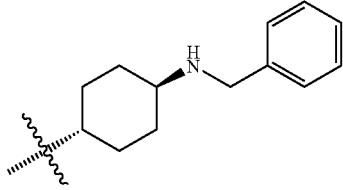 |

TABLE A-continued
| Compound No. | R¹ | R² | R³ |
|---|---|---|---|
| A-82 | 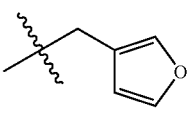 | 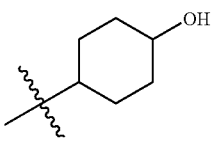 | 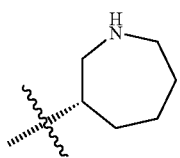 |
| A-83 | 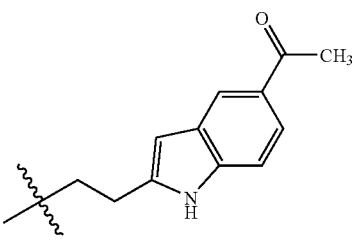 |  | 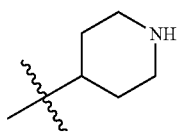 |
| A-84 | 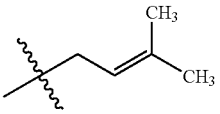 | 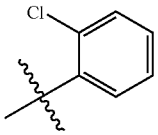 | 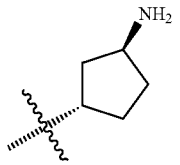 |
| A-85 | 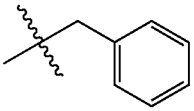 | 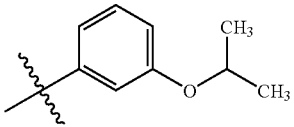 | 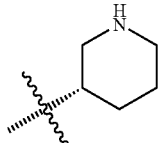 |
| A-86 | 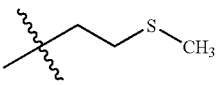 |  | 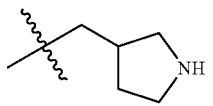 |
| A-87 | 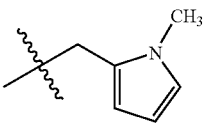 | 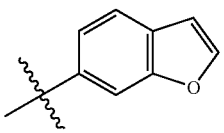 | 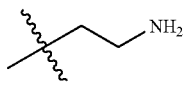 |
| A-88 | 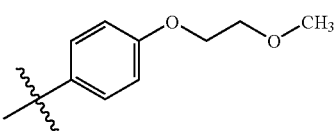 |  | 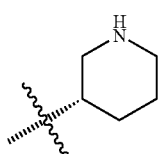 |
| A-89 | 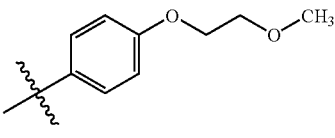 |  | 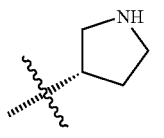 |
| A-90 | 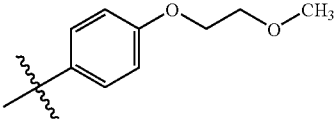 |  | 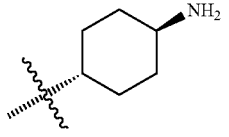 |

TABLE A-continued

| Compound No. | R¹ | R² | R³ |
| --- | --- | --- | --- |
| A-91 | 4-ethoxyphenyl | CH₂CH₂OH | piperidin-3-yl (NH) |
| A-92 | 4-ethoxyphenyl | H | piperidin-3-yl (NH) |
| A-93 | 2-chlorophenyl | H | piperidin-3-yl (NH) |
| A-94 | 2-chlorophenyl | H | 4-aminocyclohexyl |
| A-95 | 4-ethoxyphenyl | phenyl | piperidin-3-yl (NH) |
| A-96 | 2-methylbenzothiazol-6-yl | H | 4-aminocyclohexyl |
| A-97 | biphenyl-4-yl | H | 4-aminocyclohexyl |
| A-98 | 2-methoxyphenyl | H | 4-aminocyclohexyl |
| A-99 | 2-(methylthio)phenyl | H | 4-aminocyclohexyl |

TABLE A-continued
| Compound No. | R¹ | R² | R³ |
|---|---|---|---|
| A-100 | 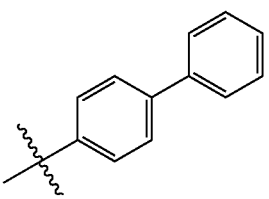 |  | 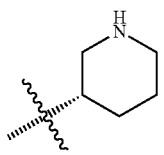 |
| A-101 | 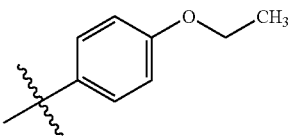 |  | 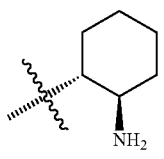 |
| A-102 | 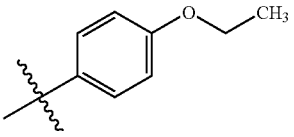 |  | 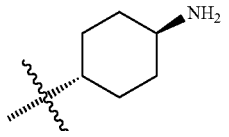 |
| A-103 | 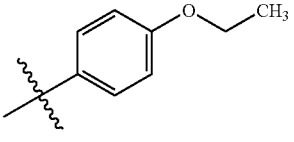 |  | 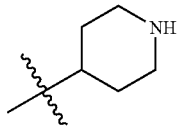 |
| A-104 | 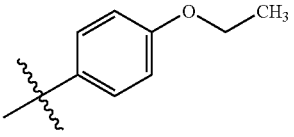 |  | 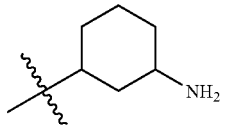 |
| A-105 | 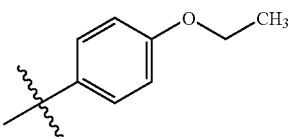 | 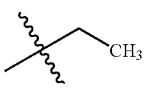 | 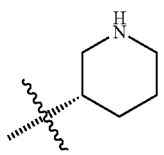 |
| A-106 | 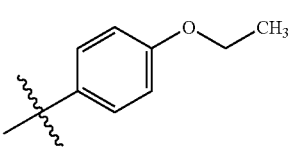 |  | 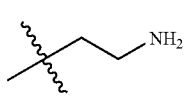 |
| A-107 | 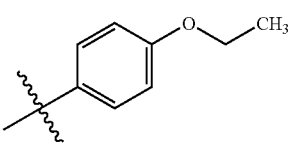 |  | 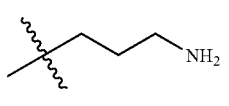 |
| A-108 | 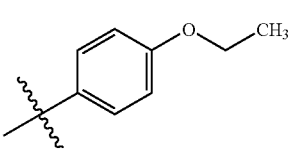 |  | 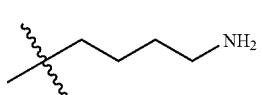 |

TABLE A-continued
| Compound No. | R¹ | R² | R³ |
|---|---|---|---|
| A-109 | 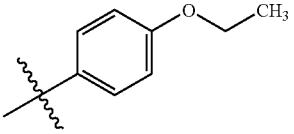 | 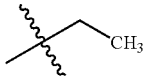 | 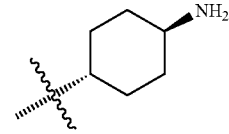 |
| A-110 | 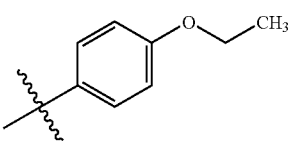 |  | 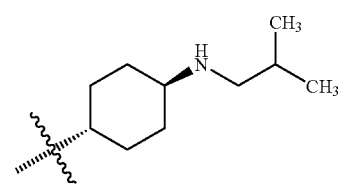 |
| A-111 | 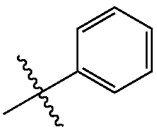 |  | 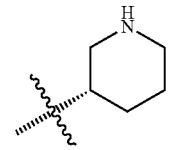 |
| A-112 | 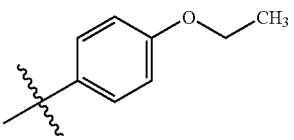 |  | 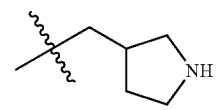 |
| A-113 | 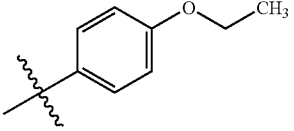 |  | 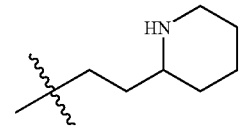 |
| A-114 | 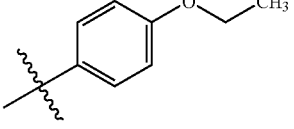 |  | 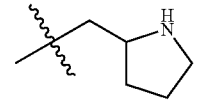 |
| A-115 | 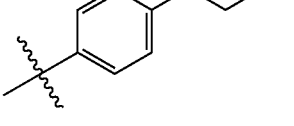 |  | 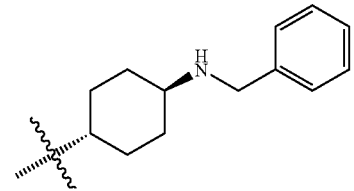 |
| A-116 | 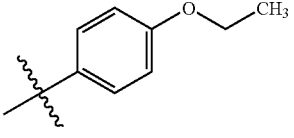 |  | 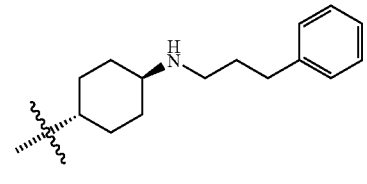 |
| A-117 | 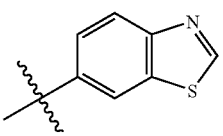 |  | 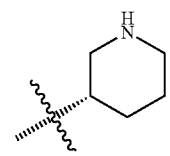 |

TABLE A-continued

| Compound No. | R¹ | R² | R³ |
|---|---|---|---|
| A-118 | 2-ethyl-benzothiazol-6-yl | CH₃ | 3-piperidinyl (NH) |
| A-119 | 4-ethoxyphenyl | CH₃ | 2-piperidinyl (NH) |
| A-120 | 4-ethoxyphenyl | CH₃ | -(CH₂)₃-NH-cyclohexyl |
| A-121 | 4-ethoxyphenyl | -CH₂CH₂CH₃ | 3-piperidinyl (NH) |
| A-122 | 4-ethoxyphenyl | -CH₂CH₂CH₃ | 4-aminocyclohexyl |
| A-123 | 4-ethoxyphenyl | -CH(CH₃)₂ | 3-piperidinyl (NH) |
| A-124 | 4-ethoxyphenyl | -CH(CH₃)₂ | 4-aminocyclohexyl |
| A-125 | 4-ethoxyphenyl | CH₃ | 4-(2-phenylethylamino)cyclohexyl |
| A-126 | 4-ethoxyphenyl | CH₃ | 4-(cyclohexylmethylamino)cyclohexyl |

TABLE A-continued
| Compound No. | R¹ | R² | R³ |
|---|---|---|---|
| A-127 | 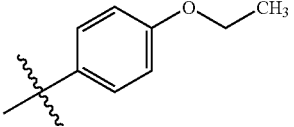 |  | 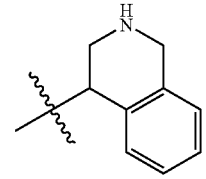 |
| A-128 | 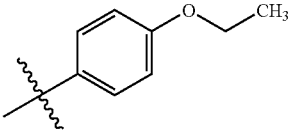 |  | 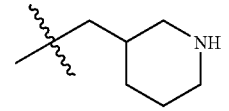 |
| A-129 | 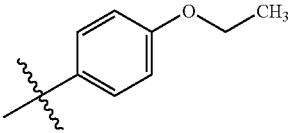 |  | 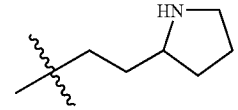 |
| A-130 | 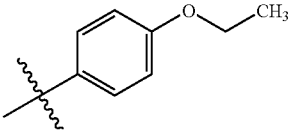 |  | 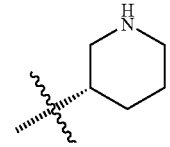 |
| A-131 | 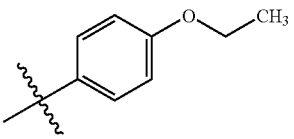 |  | 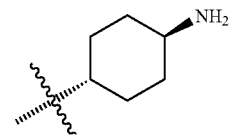 |
| A-132 | 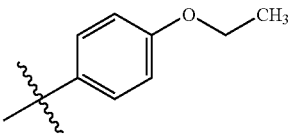 |  | 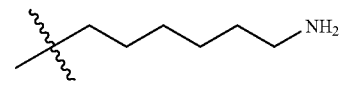 |
| A-133 | 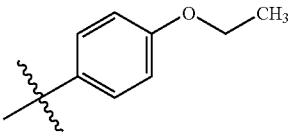 |  | 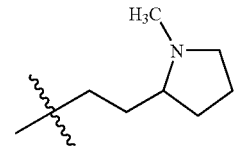 |
| A-134 | 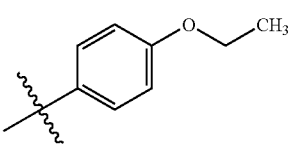 |  | 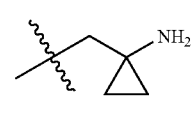 |
| A-135 | 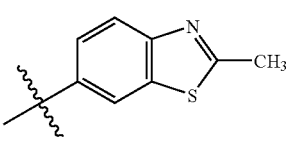 |  | 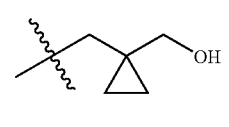 |

TABLE A-continued
| Compound No. | R¹ | R² | R³ |
|---|---|---|---|
| A-136 | 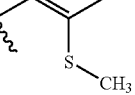 |  | 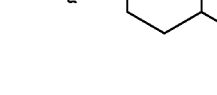 |
| A-137 |  |  | 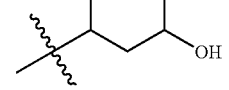 |
| A-138 | 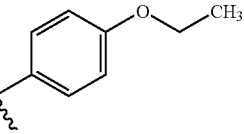 |  | 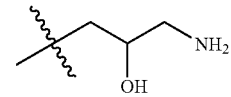 |
| A-139 | 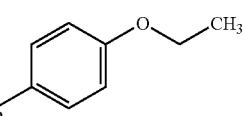 |  | 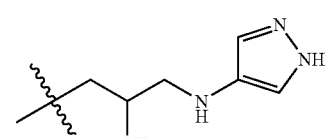 |
| A-140 | 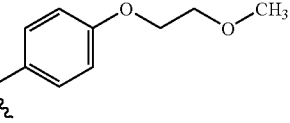 | 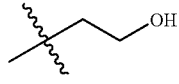 | 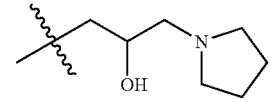 |
| A-141 | 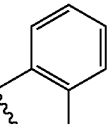 |  | 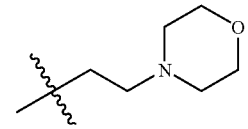 |
| A-142 | 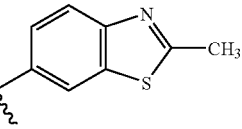 |  | 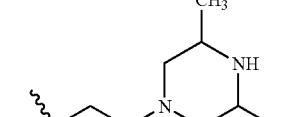 |
| A-143 | 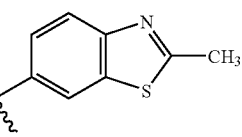 |  | 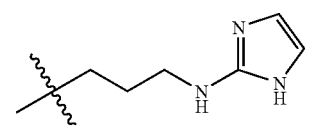 |
| A-144 | 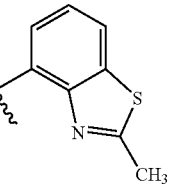 |  | 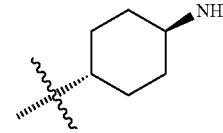 |

TABLE A-continued

| Compound No. | R¹ | R² | R³ |
|---|---|---|---|
| A-145 | benzothiazole-2-methyl (7-yl) | H | piperidin-3-yl |
| A-146 | 4-[N-ethyl-N-(2-methoxyethyl)amino]phenyl | CH₃ | piperidin-3-yl |
| A-147 | 1H-indazol-4-yl | H | trans-4-aminocyclohexyl |
| A-148 | benzoxazol-4-yl | H | piperidin-3-yl |
| A-149 | 2-(ethylthio)-1-methyl-1H-imidazol-5-yl | H | trans-4-aminocyclohexyl |
| A-150 | α-carboxybenzyl (PhCH(COOH)–) | CH₃ | pyrrolidin-3-yl |
| A-151 | 4-(ethoxymethyl)phenyl | CH₂CH₂CH₂OH | pyrrolidin-3-yl |
| A-152 | 2-methyl-1H-benzimidazol-5-yl | CH₃ | trans-4-aminocyclohexyl |

TABLE A-continued

| Compound No. | R¹ | R² | R³ |
|---|---|---|---|
| A-153 | CH₂CN | CH₃ | 4-aminocyclohexyl |
| A-154 | 2-methyl-1H-benzimidazol-5-yl | CH₂CH₂OCH₃ | piperidin-3-yl |
| A-155 | 4-ethoxyphenyl | CH₃ | 4-methylpentan-2-amine |
| A-156 | 4-ethoxyphenyl | CH₃ | 4-(1H-imidazol-4-yl)cyclohexyl |
| A-157 | 4-[ethyl(2-methoxyethyl)amino]phenyl | CH₃ | 3-(1H-imidazol-4-yl)propyl |
| A-158 | 4-(2-methoxyethoxy)phenyl | CH₂CH₂OCH₃ | 2-ethyl-3-(methylamino)propyl |
| A-159 | 2-methyl-1,3-benzothiazol-7-yl | CH₂CH₂OH | piperidin-3-yl |
| A-160 | 4-(2-methoxyethoxy)phenyl | CH₃ | azepan-4-yl |
| A-161 | 4-(2-methoxyethoxy)phenyl | CH₂CH₂OH | piperidin-3-yl |

TABLE A-continued

| Compound No. | R¹ | R² | R³ |
|---|---|---|---|
| A-162 | 1H-indazol-6-yl | sec-butyl (CH-CH₃ with ethyl) | trans-4-aminocyclohexyl |
| A-163 | 3-methyl-1H-indazol-6-yl | tert-butyl | piperidin-3-yl |
| A-164 | 1-methyl-1H-indazol-5-yl | 3-hydroxypropyl-2-yl | pyrrolidin-3-yl |
| A-165 | 1H-indazol-5-yl | phenyl | piperidin-3-yl |
| A-166 | benzo[b]thiophen-5-yl | tert-butyl | azepan-4-yl |
| A-167 | 2-methylbenzo[b]thiophen-5-yl | 3-hydroxypropyl-2-yl | piperidin-3-yl |
| A-168 | benzo[b]thiophen-6-yl | H | 4-(2-hydroxyethyl)piperidin-3-yl |
| A-169 | 2-ethylbenzo[b]thiophen-6-yl | tert-butyl | trans-4-aminocyclohexyl |
| A-170 | benzo[d]oxazol-6-yl | 1H-pyrrol-2-yl | 4-(methylamino)pentan-2-yl |

TABLE A-continued
| Compound No. | R¹ | R² | R³ |
|---|---|---|---|
| A-171 | 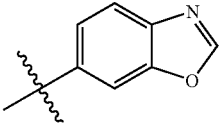 |  | 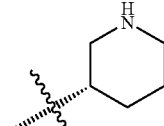 |
| A-172 | 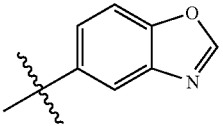 |  | 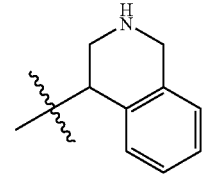 |
| A-173 | 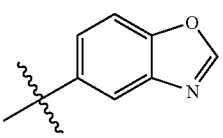 | 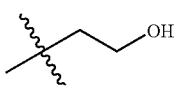 | 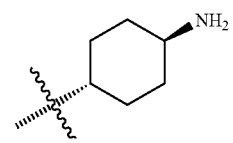 |
| A-174 | 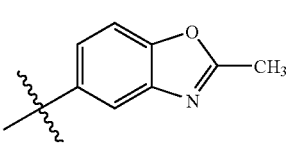 |  | 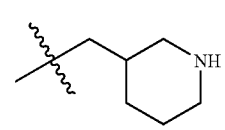 |
| A-175 | 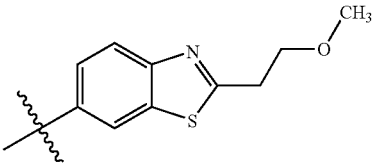 |  | 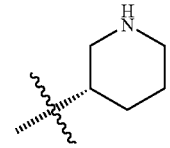 |
| A-176 | 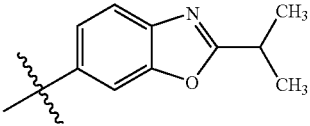 | 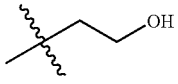 | 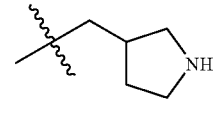 |
| A-177 | 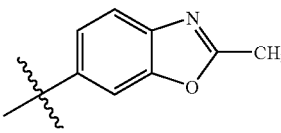 |  | 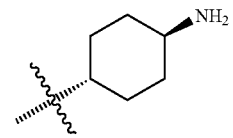 |
| A-178 | 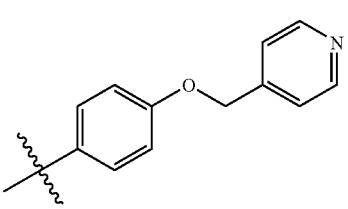 |  | 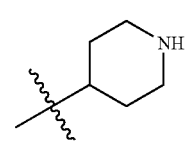 |
| A-179 | 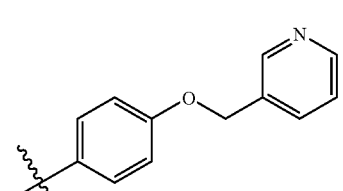 |  | 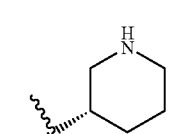 |

TABLE A-continued
| Compound No. | R¹ | R² | R³ |
|---|---|---|---|
| A-180 | 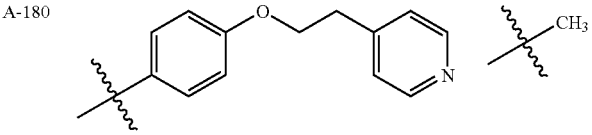 |  | 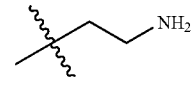 |
| A-181 | 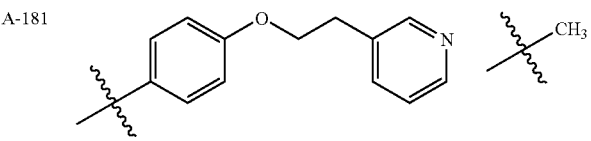 |  | 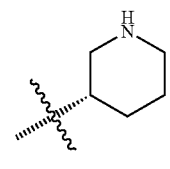 |
| A-182 | 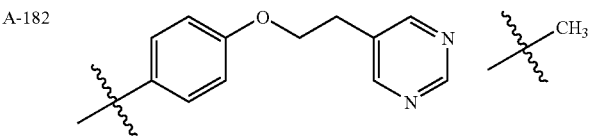 |  | 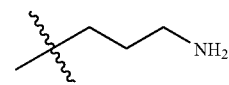 |
| A-183 | 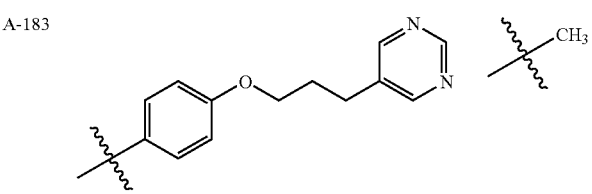 |  | 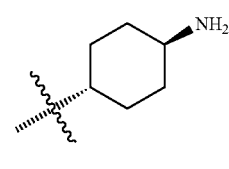 |
| A-184 | 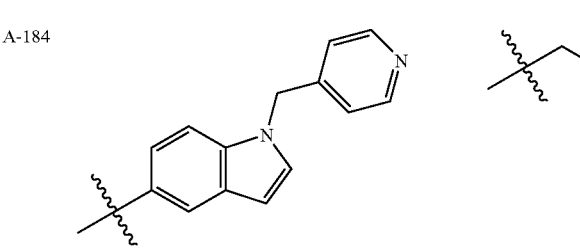 | 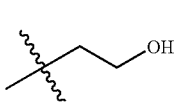 | 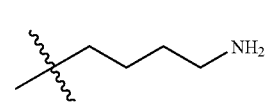 |
| A-185 | 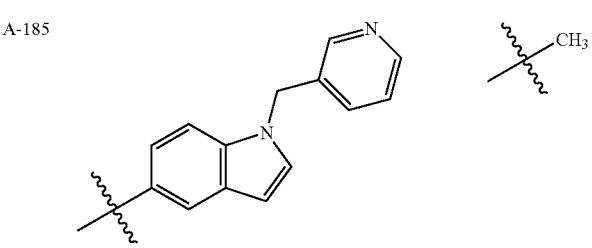 |  | 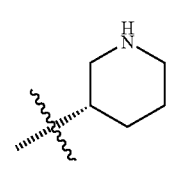 |
| A-186 | 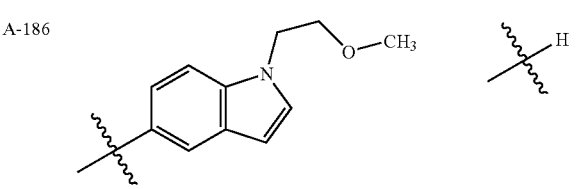 |  | 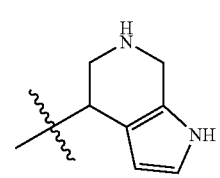 |

TABLE A-continued

| Compound No. | R¹ | R² | R³ |
|---|---|---|---|
| A-187 | 5-(2-(cyclopentyloxy)ethyl)-1H-indol-1-yl | CH₃ | piperidin-3-yl |
| A-188 | 5-(2-(pyrrolidin-1-yl)ethyl)-1H-indol-1-yl | CH₃ | 4-aminocyclohexyl |
| A-189 | 5-(2-(tetrahydrofuran-3-yl)ethyl)-1H-indol-1-yl | CH₂CH₂OH | piperidin-3-yl |
| A-190 | 5-(2-morpholinoethyl)-1H-indol-1-yl | cyclopropylmethyl | piperidin-3-yl |
| A-191 | 5-(2-(4-methylpiperazin-1-yl)ethyl)-1H-indol-1-yl | CH₃ | 4-aminocyclohexyl |
| A-192 | 5-((tetrahydrofuran-2-yl)methyl)-1H-indol-1-yl | 1H-pyrrol-2-yl | pyrrolidin-3-yl |
| A-193 | 5-ethyl-1H-indol-1-yl | CH₃ | piperidin-3-yl |

TABLE A-continued
| Compound No. | R¹ | R² | R³ |
|---|---|---|---|
| A-194 | 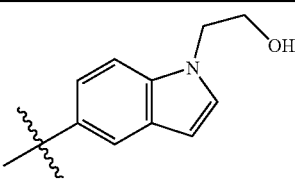 |  | 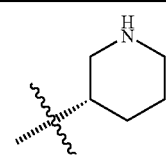 |
| A-195 | 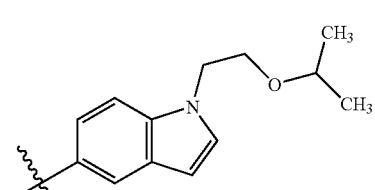 |  | 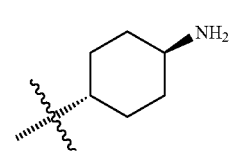 |
| A-196 | 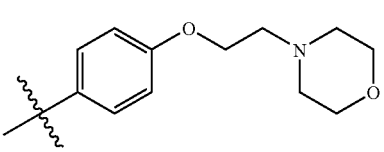 | 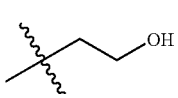 | 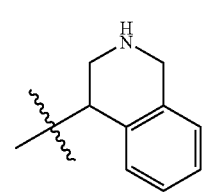 |
| A-197 | 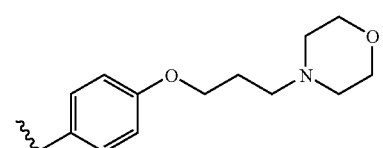 |  | 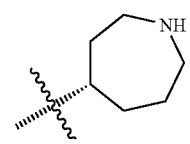 |
| A-198 | 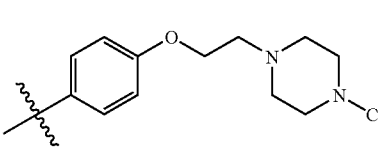 |  | 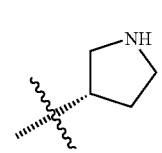 |
| A-199 | 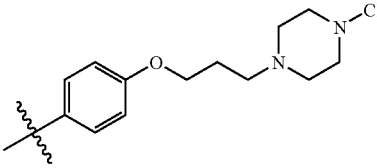 |  | 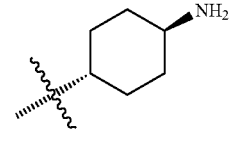 |
| A-200 | 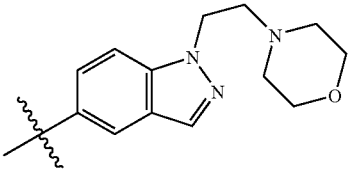 |  | 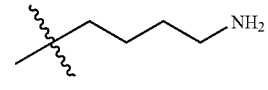 |
| A-201 | 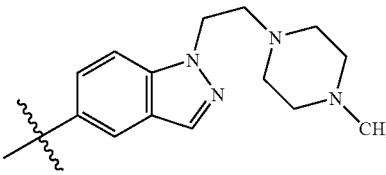 |  | 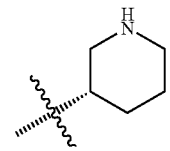 |

TABLE A-continued

| Compound No. | R¹ | R² | R³ |
|---|---|---|---|
| A-202 | 1-(2-methoxyethyl)-1H-indazol-5-yl | CH₃ | 4-aminocyclohexyl |
| A-203 | 1-(pyridin-3-ylmethyl)-1H-indazol-5-yl | CH₃ | piperidin-3-yl |
| A-204 | thiophen-3-yl | cyclopropyl | 4-aminocyclohexyl |
| A-205 | thiophen-3-yl | CH₃ | piperidin-3-yl |
| A-206 | 5-methylthiophen-3-yl | CH₃ | azepan-4-yl |
| A-207 | 5-methylthiophen-3-yl | CH₂CH₂OH | piperidin-3-yl |
| A-208 | 1-methyl-1H-pyrrol-3-yl | CH₃ | 4-(hydroxymethyl)piperidin-3-yl |
| A-209 | 1-methyl-1H-pyrazol-4-yl | phenyl | 4-aminocyclohexyl |

TABLE A-continued

| Compound No. | R¹ | R² | R³ |
|---|---|---|---|
| A-210 | 4-methyl-5-methyl-thiazol-2-yl | –CH₂CH₂OH (from quaternary C) | –C(CH₃)(CH₂CH₂CH(CH₃)NHCH₃) |
| A-211 | benzothiazol-2-yl | –C(CH₃)₃ | (R)-piperidin-3-yl |
| A-212 | 1-(carboxymethyl)-1H-indol-5-yl | –C(CH₃)₃ | (R)-piperidin-3-yl |
| A-213 | 1-(methoxycarbonylmethyl)-1H-indol-5-yl | –C(CH₃)₃ | (R)-piperidin-3-yl |

The pyrazolo[1,5-a]pyridine derivatives represented by the above formula (I) exist in tautomeric forms represented, for example, by the following formula (II):

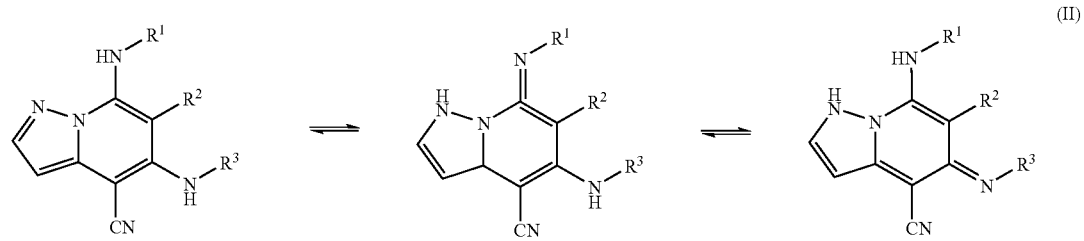

(wherein, R¹, R² and R³ are as defined in the above formula (I)).

These tautomers are also included in the scope of the present invention.

The compounds of the present invention can be synthesized by the following methods. In each formula, R¹, R² and R³ are as defined in formula (I). Reagents and solvents shown as conditions in chemical formulae are mere examples, as mentioned in the text. Each substituent may be, if necessary, protected with a suitable protective group and deprotection may be carried out in an appropriate step. Each of abbreviations of substituents, reagents and solvents in the text and tables represent the following.

Me: methyl
Et: ethyl
Boc: tert-butoxycarbonyl
DMAP: 4-N,N-dimethylaminopyridine
THF: tetrahydrofuran
DHP: dihydropyran
THP: tetrahydropyranyl
Ph: phenyl
TFA: trifluoroacetic acid
Tf: trifluoromethanesulfonyl 1) Syntheses of Compounds 1-4

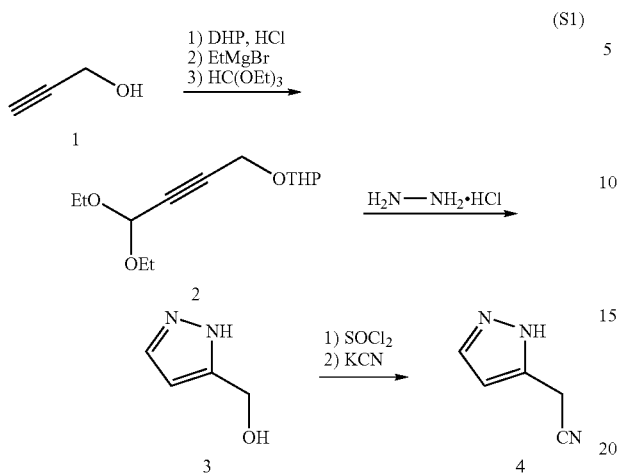

Compounds represented by formulae 1-4 are known compounds and can be synthesized by methods known for ones skilled in the art, for example, by the steps shown above. Compound 3 can be synthesized according to "R. G. Jones and M. J. Mann, J. Am. Chem. Soc. 1953, 75, 4048-4052" while compound 4 can be synthesized according to "R. G. Jones, J. Am. Chem. Soc. 1949, 71, 3994-4000."

2) Synthesis of Compound of Formula (6) from Compound 4

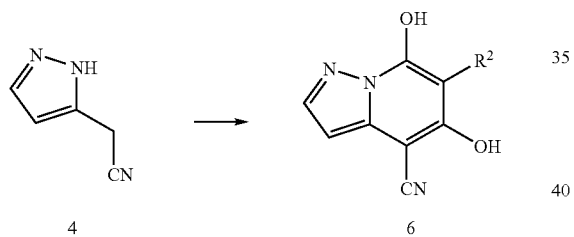

Compound of formula (6) can be obtained by reaction of compound 4 with a monosubstituted malonic diester in the presence of an appropriate base (for example, sodium ethoxide) in an appropriate organic solvent (for example, ethanol) at a temperature from 0° C. to the refluxing temperature of the solvent.

3) Synthesis of Compound of Formula (7) from Compound Formula (6)

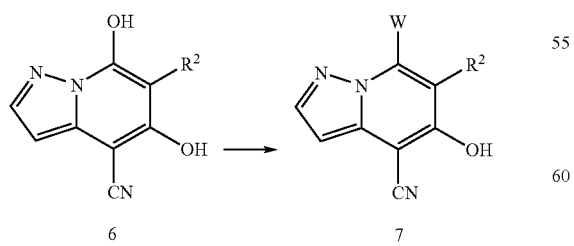

Compound of formula (7) can be obtained by halogenation of compound of formula (6) with an appropriate halogenating agent (for example, phosphoryl oxychloride) in the presence of an appropriate base (for example, N,N-dimethylaniline) or without base in an appropriate organic solvent (for example, acetonitrile) or without solvent at a temperature from 0° C. to 140° C. followed by hydrolysis with an aqueous solution containing an appropriate base (for example, sodium hydroxide) in an appropriate organic solvent (for example, 1,4-dioxane) at a temperature from 0° C. to the refluxing temperature of the solvent.

4) Synthesis of Compound of Formula (8) from Compound of Formula (7)

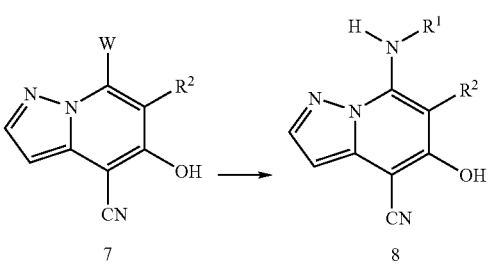

Compound of formula (8) can be obtained by reaction of compound of formula (7) with an amine derivative represented as $R^1NH_2$ in the presence of an appropriate base (for example, pyridine) or without base in an appropriate organic solvent (for example, 2-propanol) or without solvent at a temperature from 0° C. to 140° C.

5) Synthesis of Compound of Formula (9) from Compound of Formula (8)

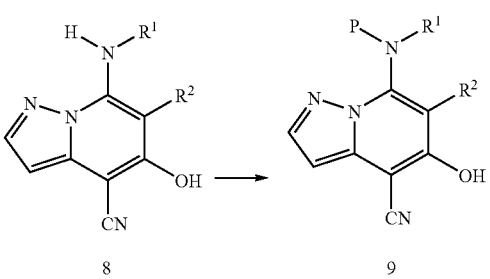

Compound of formula (9) can be obtained by reaction of compound of formula (7) with an appropriately activated reagent for introducing a P-group (di-tert-butyl dicarbonate when P is Boc) in the presence of an appropriate base (for example, triethylamine) or without base in the presence of an appropriate catalyst (for example, 4-N,N-dimethylaminopyridine) or without catalyst in an appropriate organic solvent (for example, 1,4-dioxane) at a temperature from 0° C. to the refluxing temperature of the solvent followed by hydrolysis in an appropriate solvent (for example, 1,4-dioxane) by adding an aqueous solution containing an appropriate base (for example, sodium hydroxide) or an aqueous solution containing no base at a temperature from 0° C. to the refluxing temperature of the solvent.

6) Synthesis of Compound of Formula (11) from Compound of Formula (9)

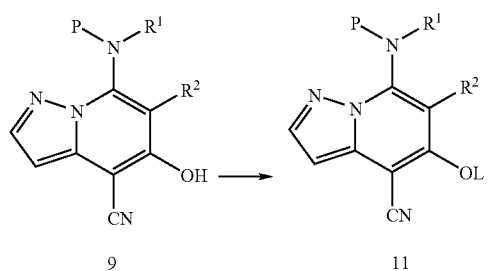

Compound of formula (11) can be obtained by reaction of compound of formula (9) with an appropriately activated reagent for introducing an L-group (a triflating agent (for example, trifluoromethanesulfonic anhydride) when L is Tf) in the presence of an appropriate base (for example, triethylamine) in an appropriate organic solvent (for example, pyridine) at a temperature from 0° C. to 50° C.

7) Synthesis of Compound of Formula (13) from Compound of Formula (11)

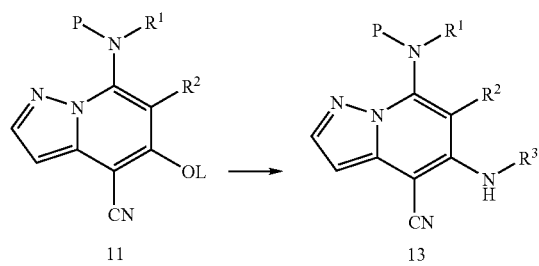

Compound of formula (13) can be obtained by reaction of compound of formula (11) with an amine derivative represented as $R^3NH_2$ in an appropriate organic solvent (for example, tetrahydrofuran) or without solvent in the presence of an appropriate base (for example, triethylamine) or without base at a temperature from room temperature to the refluxing temperature of the solvent.

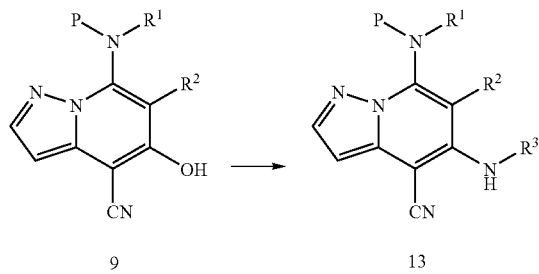

Compound of formula (13) can be also obtained by reaction of compound of formula (9) with an activating agent (for example, bromotris(pyrrolidino)phosphonium hexafluorophosphate or benzotriazol-1-yloxytris(pyrrolidino)phosphonium hexafluorophosphate) and an amine derivative represented as $R^3NH_2$ in an appropriate organic solvent (for example, 1,4-dioxane or N,N-dimethylformamide) in the presence of an appropriate base (for example, triethylamine) at a temperature from 0° C. to the refluxing temperature of the solvent according to the literature (Journal of Organic Chemistry, 2005, 70, 1957-1960).

8) Synthesis of Compound of Formula (14) from Compound of Formula (13)

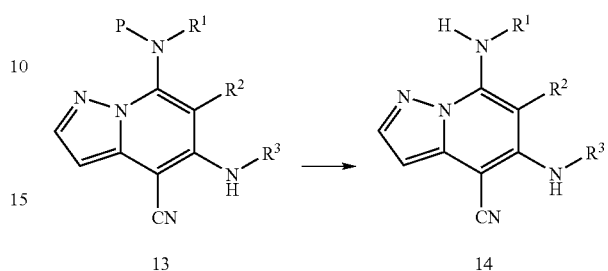

Compound of formula (14) can be obtained by reaction of compound of formula (13) with an appropriate deprotecting agent (a strong acid (for example, trifluoroacetic acid) when P is Boc) in an appropriate organic solvent (for example, dichloromethane) or without solvent at a temperature from 0° C. to the refluxing temperature of the solvent.

Pyrazolo[1,5-a]pyridine derivatives represented by formulae (5)-(10), (13) and (14) also exist in tautomeric forms as the above formula (II).

Preferred examples of $R^1$-$R^3$ in pyrazolo[1,5-a]pyridine derivatives represented by formulae (5)-(14) and the like include the preferred groups described for $R^1$-$R^3$ in the final products, that is, pyrazolo[1,5-a]pyridine derivatives represented by formula (I). Preferred examples of pyrazolo[1,5-a]pyridine derivatives represented by formulae (5)-(14) and the like include a compound comprising a combination of group(s) defined for $R^1$-$R^3$ and preferred group(s) described for $R^1$-$R^3$; a compound comprising a combination of preferred groups described for $R^1$-$R^3$; and the like.

A formulation comprising the compound of the present invention or the pharmaceutically acceptable salt thereof as an active ingredient is prepared by using carriers, excipients or other additives usually used for formulation. As carriers and excipients used for formulation, either solid or liquid may be used, and for example, there may be mentioned lactose, magnesium stearate, starch, talc, gelatin, agar, pectin, gum arabic, olive oil, sesame oil, cacao butter, ethylene glycol and others conventionally used. The formulation may be administered either orally as tablets, pills, capsules, granule, powder, liquid or the like or parenterally through injection such as an intravenous injection and an intramuscular injection, suppository, percutaneous administration or the like.

As diseases for which the MAPKAP-K2 inhibitor of the present invention is effective, there may be mentioned neurodegenerative/neurological disorders (including dementia), sepsis, autoimmune diseases, destructive osteopathy, inflammatory bowel disease, psoriasis, diabetes mellitus, cancer, ischemic reperfusion injury, angiodysplasia, cachexia, obesity, angiogenesis, asthma and/or chronic obstructive pulmonary disease (COPD).

As autoimmune diseases, specifically, there may be mentioned rheumatoid arthritis, ankylosing spondylitis, juvenile rheumatoid arthritis, psoriatic arthritis, graft-versus-host disease, diabetes mellitus or Crohn's disease.

The dose of the compound of present invention is, although it varies depending on the kind of disease, the administration route, the age and sex of patient and the degree of disease, usually 1-500 mg/day for one adult.

EXAMPLES

The present invention will be explained with specific examples. However, the present invention is not limited to these examples.

The compound number given to each compound in the following examples corresponds to the compound number given to the compound mentioned as preferred example in Table A. The structures of novel compounds isolated were confirmed by $^1$H-NMR and/or mass analysis measured on a single quadrupole instrumentation equipped with an electrospray source or other appropriate analytical methods.

For $^1$H-NMR spectra (400 MHz, DMSO-$d_6$ or CDCl$_3$), chemical shifts (δ:ppm) and coupling constants (J:Hz) are shown. Each of the following abbreviation represents the followings: s=singlet, d=doublet, t=triplet, q=quartet, brs=broad singlet, m=multiplet. For results of mass analysis, M$^+$+H, that is, the measured value observed as the molecular mass of compound (M) with one proton (H$^+$) added, is shown. "HPLC retention time" represents the retention time (unit: min) of compound in HPLC analysis under the following analytical conditions.

Conditions for HPLC (High Performance Liquid Chromatography)
Instrumental system: Hewlett-Packard 1100HPLC
Column: Cadenza CD-C18 (Imtakt) 100 mm×4.6 mm (i.d.)
Solvent: A: H$_2$O/acetonitrile=95/5, 0.05% TFA
B: H$_2$O/acetonitrile=5/95, 0.05% TFA
Flow rate: 1.0 mL/min
Gradient:
0 to 1 min; Solvent B: 10%, Solvent A: 90%
1 to 13 min; Solvent B: from 10% to 70%, Solvent A: from 90% to 30%
13 to 14 min; Solvent B: from 70% to 100%, Solvent A: from 30% to 0%
14 to 16 min; Solvent B: 100%, Solvent A: 0%
16 to 19 min; Solvent B: from 100% to 10%, Solvent A: from 0% to 90%

Example 1

Synthesis of 5,7-dihydroxy-6-methylpyrazolo[1,5-a]pyridine-4-carbonitrile (5)

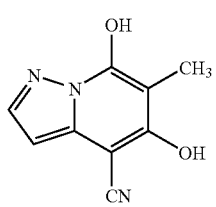

2-(Pyrazol-3-yl)ethanenitrile (4) (2.14 g), which was synthesized as shown in the above scheme (S1), was dissolved in anhydrous ethanol (40 mL). Diethyl methylmalonate (3.78 mL) was added to this solution and the resultant mixture was stirred. To this solution, sodium ethoxide (3.40 g) was added and the mixture was stirred under reflux with heating for 3 days. After cooled to room temperature, the reaction solution was diluted with water (100 mL) and the pH of the solution was adjusted to 2 by adding 6 mol/L hydrochloric acid. The resultant crude product was collected by filtration, washed with brine, and dried under reduced pressure to obtain the title compound (5) (3.06 g), a part of which was purified with preparative HPLC and the NMR spectrum was recorded.

H-NMR (400 MHz, DMSO-$d_6$) δ (ppm): 10.37 (brs, 1H), 8.22 (d, J=3.2 Hz, 1H), 6.42 (d, J=3.2 Hz, 1H), 1.99 (s, 3H). ESI/MS: 190.0 (M$^+$+H, C$_9$H$_7$N$_3$O$_2$). HPLC retention time: 4.58 min Compounds described below in Examples 2 to 8 were synthesized by the method described in Example 1 using the corresponding starting materials and reagents.

Example 2

5,7-Dihydroxy-6-(2-propenyl)pyrazolo[1,5-a]pyridine-4-carbonitrile (6)

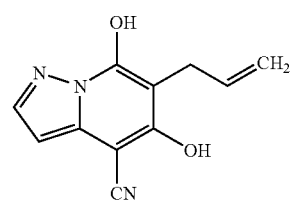

ESI/MS: 216.2 (M$^+$+H, C$_{11}$H$_9$N$_3$O$_2$). HPLC retention time: 4.84 min

Example 3

5,7-Dihydroxy-6-phenylpyrazolo[1,5-a]pyridine-4-carbonitrile (7)

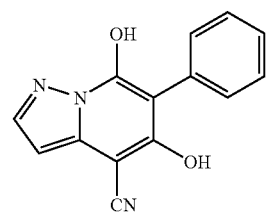

ESI/MS: 252.2 (M$^+$+H, C$_{14}$H$_9$N$_3$O$_2$).

Example 4

5,7-Dihydroxypyrazolo[1,5-a]pyridine-4-carbonitrile (8)

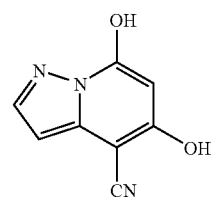

$^1$H-NMR (400 MHz, DMSO-d$_6$) δ (ppm): 11.41 (brs, 1H), 8.19 (d, J=2.8 Hz, 1H), 6.41 (d, J=2.8 Hz, 1H), 5.55 (s, 1H). ESI/MS: 176.3 (M$^+$+H, C$_8$H$_5$N$_3$O$_2$).

Example 5

5,7-Dihydroxy-6-ethylpyrazolo[1,5-a]pyridine-4-carbonitrile (9)

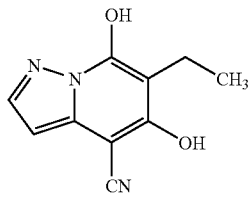

$^1$H-NMR (400 MHz, DMSO-d$_6$) δ (ppm): 8.24 (dd, J=3.2, 0.8 Hz, 1H), 6.42 (dd, J=3.2, 0.8 Hz, 1H), 2.56 (q, J=7.6 Hz, 2H), 1.00 (t, J=7.6 Hz, 3H). ESI/MS: 204.0 (M$^+$+H, C$_{10}$H$_9$N$_3$O$_2$).

Example 6

5,7-Dihydroxy-6-propylpyrazolo[1,5-a]pyridine-4-carbonitrile (10)

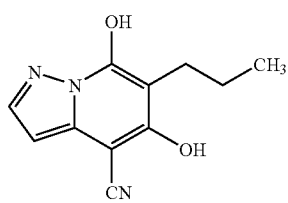

$^1$H-NMR (400 MHz, DMSO-d$_6$) δ (ppm): 8.22 (d, J=4.0 Hz, 1H), 6.41 (d, J=4.0 Hz, 1H), 2.54-2.48 (m, 2H), 1.42 (m, J=7.5, 7.3 Hz, 2H), 0.87 (t, J=7.3 Hz, 3H). ESI/MS: 218.1 (M$^+$+H, C$_{11}$H$_{11}$N$_3$O$_2$).

Example 7

5,7-Dihydroxy-6-(methylethyl)pyrazolo[1,5-a]pyridine-4-carbonitrile (11)

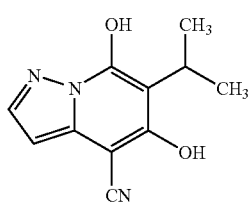

$^1$H-NMR (400 MHz, DMSO-d$_6$) δ (ppm): 8.23 (d, J=3.2 Hz, 1H), 6.40 (d, J=3.2 Hz, 1H), 3.16 (m, J=7.0 Hz, 1H), 1.42 (d, J=7.0 Hz, 6H). ESI/MS: 218.1 (M$^+$+H, C$_{11}$H$_{11}$N$_3$O$_2$).

Example 8

5,7-Dihydroxy-6-cyclopropylpyrazolo[1,5-a]pyridine-4-carbonitrile (12)

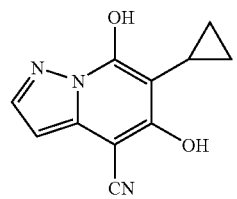

$^1$H-NMR (400 MHz, DMSO-d$_6$) δ (ppm): 8.17 (brs, 1H), 6.37 (brs, 1H), 1.54-1.50 (m, 1H), 0.83-0.80 (m, 2H), 0.72-0.68 (m, 2H). ESI/MS: 216.1 (M$^+$+H, C$_{11}$H$_9$N$_3$O$_2$).

Example 9

Synthesis of 7-chloro-5-hydroxy-6-methylpyrazolo[1,5-a]pyridine-4-carbonitrile (13)

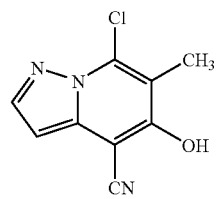

To the crude product (378 mg) of 5,7-dihydroxy-6-methylpyrazolo[1,5-a]pyridine-4-carbonitrile (5), N,N-dimethylaniline (380 μL) was added and this mixture was suspended in phosphoryl chloride (20 mL). This suspension was stirred under reflux with heating for 3 h. After the reaction solution was cooled to room temperature, excessive phosphoryl chloride was removed under reduced pressure. The residue was diluted with ethyl acetate and water, and two layers were separated. The organic layer was reversely extracted with saturated aqueous sodium hydrogen carbonate solution, and the aqueous extract was combined with the aqueous layer. The pH of combined aqueous layers were adjusted to 10 with 2 mol/L aqueous sodium hydroxide solution, and the solution was stirred for 4 days. This mixture was acidified to pH 2 with 1 mol/L hydrochloric acid and extracted with ethyl acetate three times. The combined organic layers were washed with a mixture of brine and 1 mol/L hydrochloric acid (5:1) and dried over sodium sulfate. The solvent was removed under reduced pressure to obtain the title compound (13) (211 mg), a part of which was purified with preparative HPLC and the NMR spectrum was recorded.

$^1$H-NMR (400 MHz, DMSO-d$_6$) δ (ppm): 8.04 (d, J=2.2 Hz, 1H), 6.53 (d, J=2.2 Hz, 1H), 2.29 (s, 3H). ESI/MS: 208.0 (M$^+$+H, C$_9$H$_6$ClN$_3$O). HPLC retention time: 8.07 min Compounds described below in Examples 10 to 16 were synthesized by the method described in Example 9 using the corresponding starting materials and reagents.

Example 10

7-Chloro-5-hydroxy-6-(2-propenyl)pyrazolo[1,5-a]pyridine-4-carbonitrile (14)

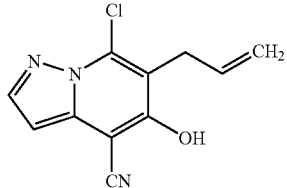

$^1$H-NMR (400 MHz, CDCl$_3$) δ (ppm): 8.05 (d, J=2.2 Hz, 1H), 6.62 (d, J=2.2 Hz, 1H), 5.93 (m, 1H), 5.21-5.15 (m, 2H), 3.64 (dt, J=6.2, 1.5 Hz, 2H). ESI/MS: 234.3 (M$^+$+H, C$_{11}$H$_8$ClN$_3$O).

Example 11

7-Chloro-5-hydroxy-6-phenylpyrazolo[1,5-a]pyridine-4-carbonitrile (15)

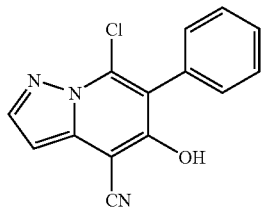

ESI/MS: 270.1 (M$^{++H,}$ C$_{14}$H$_8$ClN$_3$O).

Example 12

7-Chloro-5-hydroxypyrazolo[1,5-a]pyridine-4-carbonitrile (16)

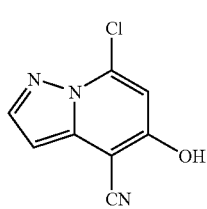

$^1$H-NMR (400 MHz, DMSO-d$_6$) δ (ppm): 8.12 (d, J=2.0 Hz, 1H), 6.86 (s, 1H), 6.60 (d, J=2.0 Hz, 1H). ESI/MS: 194.1 (M$^+$+H, C$_8$H$_4$ClN$_3$O).

Example 13

7-Chloro-5-hydroxy-6-ethylpyrazolo[1,5-a]pyridine-4-carbonitrile (17)

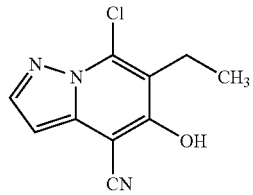

$^1$H-NMR (400 MHz, DMSO-d$_6$) δ (ppm): 8.06 (dd, J=1.7, 1.7 Hz, 1H), 6.55 (dd, J=1.7, 1.7 Hz, 1H), 2.77 (q, J=7.6 Hz, 2H), 1.10 (t, J=7.6 Hz, 3H). ESI/MS: 222.0 (M$^+$+H, C$_{10}$H$_8$ClN$_3$O).

Example 14

7-Chloro-5-hydroxy-6-propylpyrazolo[1,5-a]pyridine-4-carbonitrile (18)

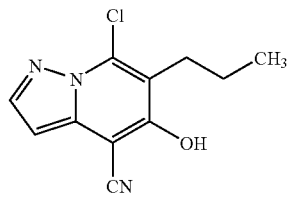

$^1$H-NMR (400 MHz, DMSO-d$_6$) δ (ppm): 8.06 (d, J=2.2 Hz, 1H), 6.54 (d, J=2.2 Hz, 1H), 2.74 (t, J=7.8 Hz, 2H), 1.53 (m, J=7.8, 7.6 Hz, 2H), 0.94 (t, J=7.6 Hz, 3H). ESI/MS: 236.1 (M$^+$+H, C$_{11}$H$_{10}$ClN$_3$O).

Example 15

7-Chloro-5-hydroxy-6-(methylethyl)pyrazolo[1,5-a]pyridine-4-carbonitrile (19)

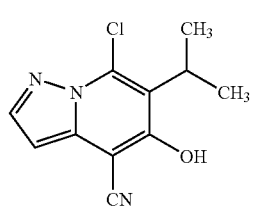

$^1$H-NMR (400 MHz, CDCl$_3$) δ (ppm): 8.04 (d, J=2.2 Hz, 1H), 6.58 (d, J=2.2 Hz, 1H), 3.69 (m, J=7.1 Hz, 1H), 1.43 (d, J=7.1 Hz, 6H). ESI/MS: 236.2 (M$^+$+H, C$_{11}$H$_{10}$ClN$_3$O).

Example 16

7-Chloro-5-hydroxy-6-cyclopropylpyrazolo[1,5-a]pyridine-4-carbonitrile (20)

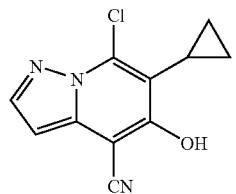

$^1$H-NMR (400 MHz, CDCl$_3$) δ (ppm): 8.05 (d, J=2.2 Hz, 1H), 6.64 (d, J=2.2 Hz, 1H), 1.78 (tt, J=8.0, 3.6 Hz, 1H), 1.35-1.31 (m, 2H), 1.35-1.31 (m, 2H). ESI/MS: 234.0 (M$^+$+H, C$_{11}$H$_8$ClN$_3$O).

Example 17

Synthesis of 7-[(4-ethoxyphenyl)amino]-5-hydroxy-6-methyl-pyrazolo[1,5-a]pyridine-4-carbonitrile (21)

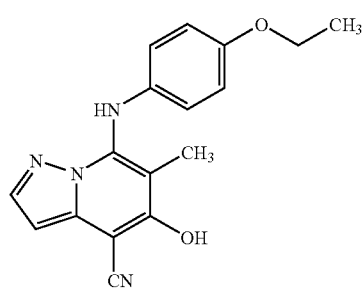

The crude product (9.25 mg) of 7-chloro-5-hydroxy-6-methylpyrazolo[1,5-a]pyridine-4-carbonitrile (13) was dissolved in 2-propanol (2.2 mL). To this solution, p-phenetidine (289 μL) was added and the mixture was stirred under reflux with heating for 3 days. After cooled to room temperature, the reaction solution was diluted with ethyl acetate. This solution was washed with a mixture of brine and 1 mol/L hydrochloric acid (1:1) and then with a mixture of brine and saturated aqueous sodium hydrogen carbonate solution (9:1) and dried over sodium sulfate. After the solvent was removed under reduced pressure, the residue was purified with silica-gel column chromatography (hexane/ethyl acetate=1/1) to obtain the title compound (21) (77.8 mg, Yield 56%).

$^1$H-NMR (400 MHz, CDCl$_3$) δ (ppm): 8.09 (brs, 1H), 7.91 (d, J=2.2 Hz, 1H), 7.04 (d, J=8.9 Hz, 2H), 6.88 (d, J=8.9 Hz, 2H), 6.48 (d, J=2.2 Hz, 1H), 5.30 (brs, 1H), 4.04 (q, J=7.0 Hz, 2H), 1.78 (s, 3H), 1.43 (t, J=7.0 Hz, 3H). ESI/MS: 309.1 (M$^+$+H, C$_{17}$H$_{16}$N$_4$O$_2$). HPLC retention time: 13.14 min The compounds described below in Examples 18 to 21 were synthesized by the method described in Example 17 using the corresponding starting materials and reagents.

Example 18

7-[(4-Ethoxyphenyl)amino]-5-hydroxy-6-(2-propenyl)pyrazolo[1,5-a]pyridine-4-carbonitrile (22)

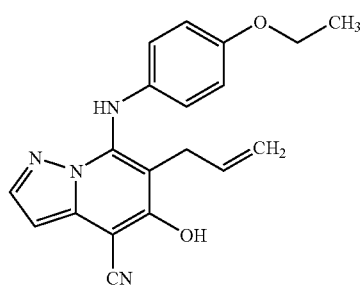

$^1$H-NMR (400 MHz, CDCl$_3$) δ (ppm): 8.09 (s, 1H), 7.91 (d, J=2.0 Hz, 1H), 7.11 (d, J=8.8 Hz, 2H), 6.87 (d, J=8.8 Hz, 2H), 6.49 (d, J=2.0 Hz, 1H), 5.72-5.60 (m, 1H), 5.04 (dq, J=10.1, 1.5 Hz, 1H), 4.93 (dq, J=17.1, 1.5 Hz, 1H), 4.04 (q, J=7.0 Hz, 2H), 3.09 (dt, J=5.8, 1.6 Hz, 2H), 1.43 (t, J=7.0 Hz, 3H). ESI/MS: 335.4 (M$^+$+H, C$_{19}$H$_{18}$N$_4$O$_2$).

Example 19

5-Hydroxy-7-{[4-(2-methoxyethoxy)phenyl]amino}-6-methylpyrazolo[1,5-a]pyridine-4-carbonitrile (23)

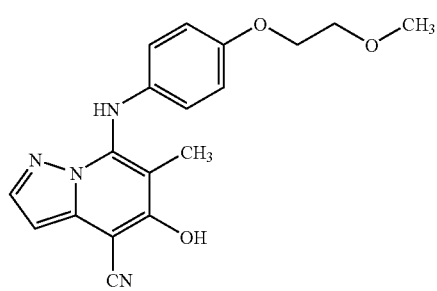

ESI/MS: 339.1 (M$^+$+H, C$_{18}$H$_{18}$N$_4$O$_3$).

Example 20

5-Hydroxy-6-methyl-7-[(2-methylbenzothiazol-6-yl)amino]pyrazolo[1,5-a]pyridine-4-carbonitrile (24)

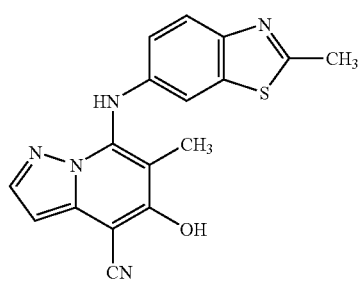

ESI/MS: 336.0 (M$^+$+H, C$_{17}$H$_{13}$N$_5$OS).

Example 21

7-(benzothiazol-6-ylamino)-5-hydroxy-6-methylpyrazolo[1,5-a]pyridine-4-carbonitrile (25)

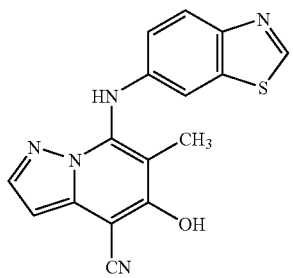

ESI/MS: 322.1 (M⁺+H, $C_{16}H_{11}N_5OS$).

Example 22

Synthesis of tert-butoxy-N-(4-cyano-5-hydroxy-6-methylpyrazolo[1,5-a]pyridin-7-yl)-N-(4-ethoxyphenyl)carboxamide (26)

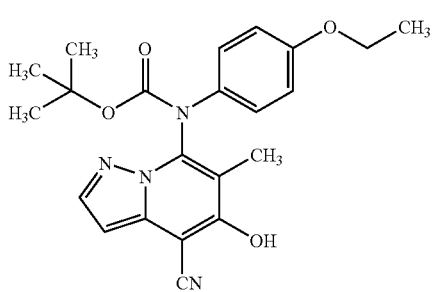

7-(4-Ethoxyphenylamino)-5-hydroxy-6-methylpyrazolo[1,5-a]pyridine-4-carbonitrile (21) (195 mg) was dissolved in 1,4-dioxane (6.3 mL). To this solution, di-tert-butyl dicarbonate (346 mg) and 4-N,N-dimethylaminopyridine (19 mg) were added and the mixture was stirred at room temperature for 1 h. To this solution, 0.5 mol/L aqueous sodium hydroxide solution (1.3 mL) was added and the mixture was stirred at room temperature for 3 hr. The reaction solution was diluted with ethyl acetate, washed with a mixture of brine and saturated aqueous ammonium chloride solution (1:1) and dried over sodium sulfate. The solvent was removed under reduced pressure and the residue was purified with silica-gel column chromatography (hexane/ethyl acetate=1/1) to obtain the title compound (26) (242 mg, Yield 93%).

¹H-NMR (400 MHz, DMSO-d₆) δ (ppm): 8.01 (brs, 1H), 7.17 (d, J=8.7 Hz, 2H), 6.85 (d, J=8.7 Hz, 2H), 6.51 (d, J=2.0 Hz, 1H), 6.12 (brs, 1H), 3.96 (q, J=7.0 Hz, 2H), 2.07 (brs, 3H), 1.35 (s, 9H), 1.28 (t, J=7.0 Hz, 3H). ESI/MS: 409.2 (M⁺+H, $C_{22}H_{24}N_4O_4$). HPLC retention time: 14.54 min The compounds described below in Examples 23 to 37 were synthesized by the method described in Example 22 using the corresponding starting materials and reagents.

Example 23 tert-Butoxy-N-[4-cyano-5-hydroxy-6-(2-propenyl)pyrazolo[1,5a]pyridin-7-yl]-N-(4-ethoxyphenyl)carboxamide (27)

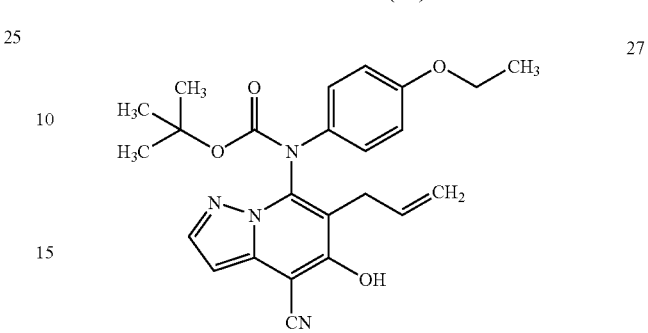

¹H-NMR (400 MHz, DMSO-d₆) δ (ppm): 12.09 (brs, 1H), 7.11 (d, J=8.8 Hz, 2H), 6.85 (d, J=8.8 Hz, 2H), 6.54 (d, J=1.7 Hz, 1H), 5.75-5.55 (m, 1H), 5.00-4.80 (m, 2H), 3.96 (q, J=7.2 Hz, 2H), 3.45-3.30 (m, 2H), 1.28 (t, J=7.0 Hz, 3H), 1.15 (brs, 9H). ESI/MS: 435.3 (M⁺+H, $C_{24}H_{26}N_4O_4$). HPLC retention time 15.29 min

Example 24

(tert-Butoxy)-N-(4-cyano-5-hydroxy-6-methylpyrazolo[1,5-a]pyridin-7-yl)-N-[4-(2-methoxyethoxy)phenyl]carboxamide (28)

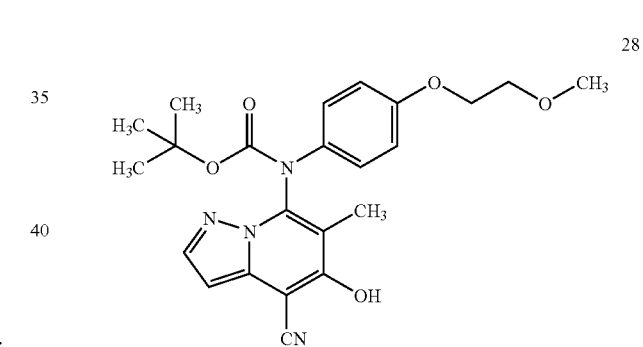

ESI/MS: 383.1 (M⁺+H, $C_{23}H_{26}N_4O_5$: fragment ion generated by elimination of isobutene ($C_4H_8$: 56) was observed).

Example 25

(tert-Butoxy)-N-(4-cyano-5-hydroxy-6-methylpyrazolo[1,5-a]pyridin-7-yl)-N-(2-methylbenzothiazol-6-yl)carboxamide (29)

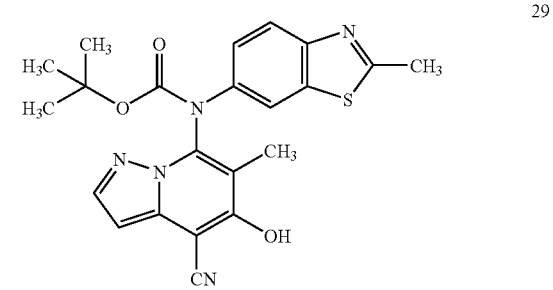

ESI/MS: 436.1 (M⁺+H, $C_{22}H_{21}N_5O_3S$).

Example 26 tert-Butoxy-N-(4-cyano-5-hydroxy-6-phenylpyrazolo[1,5-a]pyridin-7-yl)-N-(4-ethoxyphenyl)carboxamide (30)

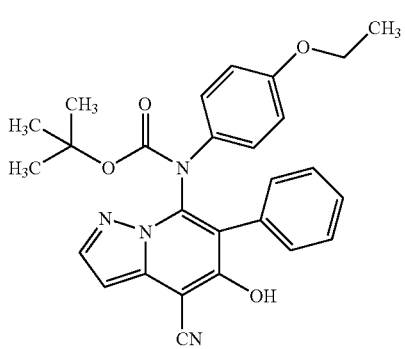

ESI/MS: 471.4 (M$^+$+H, C$_{27}$H$_{26}$N$_4$O$_4$).

Example 27 tert-Butoxy-N-(4-cyano-5-hydroxy-6-ethylpyrazolo[1,5-a]pyridin-7-yl)-N-(4-ethoxyphenyl)carboxamide (31)

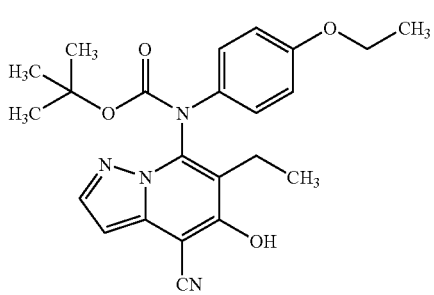

$^1$H-NMR (400 MHz, CDCl$_3$) δ (ppm): 7.81 (d, 1.7H, 1H), 7.20 (d, J=8.7 Hz, 2H) 6.75 (d, J=8.7 Hz, 2H), 6.26 (d, J=1.7 Hz, 1H), 3.94 (q, J=7.1 Hz, 2H), 3.14 (q, J=7.3 Hz, 2H), 1.36 (t, J=7.1 Hz, 3H), 1.30 (t, J=7.3 Hz, 3H), 1.26 (s, 9H). ESI/MS: 423.2 (M$^+$+H, C$_{23}$H$_{26}$N$_4$O$_4$).

Example 28 tert-Butoxy-N-(4-cyano-5-hydroxy-6-propylpyrazolo[1,5-a]pyridin-7-yl)-N-(4-ethoxyphenyl)carboxamide (32)

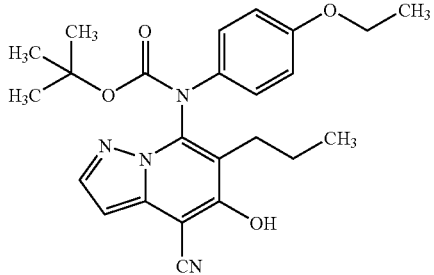

ESI/MS: 437.2 (M$^+$+H, C$_{24}$H$_{28}$N$_4$O$_4$).

Example 29 tert-Butoxy-N-{4-cyano-5-hydroxy-6-(methylethyl)pyrazolo[1,5-a]pyridin-7-yl}-N-(4-ethoxyphenyl)carboxamnide (33)

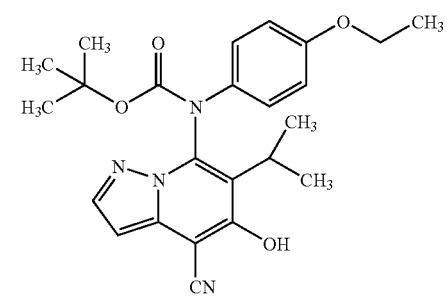

$^1$H-NMR (400 MHz, CDCl$_3$) δ (ppm): 7.97 (d, 1.7H, 1H), 7.21 (d, J=8.8 Hz, 2H) 6.79 (d, J=8.8 Hz, 2H), 6.51 (d, 1.7H, 1H), 3.96 (q, J=7.0 Hz, 2H), 3.45-3.38 (m, 1H), 1.37 (brs, 6H), 1.27 (brs, 9H). ESI/MS: 437.2 (M$^+$+H, C$_{24}$H$_{28}$N$_4$O$_4$).

Example 30 tert-Butoxy-N-(4-cyano-5-hydroxy-6-cyclopropylpyrazolo[1,5-a]pyridin-7-yl)-N-(4-ethoxy-phenyl)carboxamide (34)

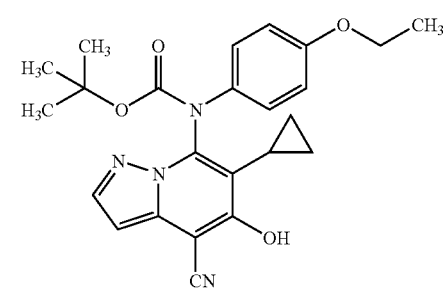

ESI/MS: 435.2 (M$^+$+H, C$_{24}$H$_{26}$N$_4$O$_4$).

Example 31

(tert-Butoxy)-N-(2-chlorophenyl)-N-[4-cyano-5-hydroxy(pyrazolo[1,5-a]pyridin-7-yl)]carboxamide (35)

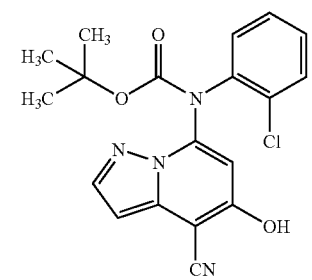

$^1$H-NMR (400 MHz, CDCl$_3$) δ (ppm): 8.08 (d, J=2.4 Hz, 1H), 7.64 (dd, J=8.0, 2.4 Hz, 1H), 7.51 (dd, J=8.0, 2.4 Hz, 1H), 7.32-7.22 (m, 2H), 6.75 (s, 1H), 6.68 (d, J=2.4 Hz, 1H), 1.47 (s, 9H). ESI/MS: 385.2 (M$^+$+H, C$_{19}$H$_{17}$ClN$_4$O$_3$).

Example 32

(tert-Butoxy)-N-[4-cyano-5-hydroxy(pyrazolo[1,5-a]pyridin-7-yl)]-N-(2-methylthiophenyl)carboxamide (36)

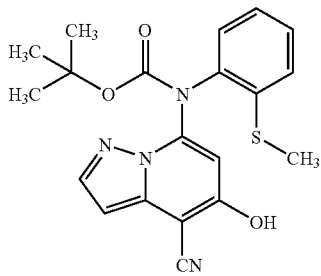

$^1$H-NMR (400 MHz, CDCl$_3$) δ (ppm): 8.00 (s, 1H), 7.48 (dd, J=8.0, 1.2 Hz, 1H), 7.31-7.24 (m, 2H), 7.04 (td, J=8.0, 1.2 Hz, 1H), 6.78 (s, 1H), 6.54 (d, J=2.4 Hz, 1H), 2.48 (s, 3H), 1.36 (s, 9H). ESI/MS: 397.4 (M$^+$+H, C$_{20}$H$_{20}$N$_4$O$_3$S).

Example 33

(tert-Butoxy)-N-[4-cyano-5-hydroxy(pyrazolo[1,5-a]pyridin-7-yl)]-N-(2-methoxyphenyl)carboxamide (37)

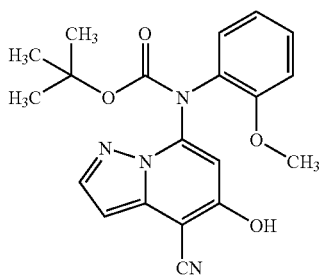

$^1$H-NMR (400 MHz, CDCl$_3$) δ (ppm): 7.98 (d, 1H), 7.37 (dd, J=8.0, 1.6 Hz, 1H), 7.26 (t, J=8 Hz, 1H), 6.94 (d, J=8.0 Hz, 1H), 6.84 (t, J=8.0 Hz, 1H), 6.53 (d, J=2.0 Hz, 1H), 6.44 (s, 1H), 3.83 (s, 3H), 1.35 (s, 3H). ESI/MS: 381.4 (M$^+$+H, C$_{20}$H$_{20}$N$_4$O$_4$).

Example 34

(tert-Butoxy)-N-[4-cyano-5-hydroxy(pyrazolo[1,5-a]pyridin-7-yl)]-N-(2-methylphenyl)carboxamide (38)

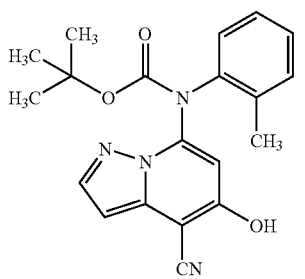

$^1$H-NMR (400 MHz, CDCl$_3$) δ (ppm): 7.98 (d, J=2.0 Hz, 1H), 7.25-7.15 (m, 3H), 7.07 (t, J=8.0 Hz, 1H), 6.87 (s, 1H), 6.52 (d, J=2.0 Hz, 1H), 6.21 (s, 1H), 2.28 (s, 3H), 1.35 (s, 9H). ESI/MS: 365.6 (M$^+$+H, C$_{20}$H$_{20}$N$_4$O$_3$).

Example 35

(tert-Butoxy)-N-[4-cyano-5-hydroxy(pyrazolo[1,5-a]pyridin-7-yl)]-N-(2-methylbenzothiazol-6-yl)carboxamide (39)

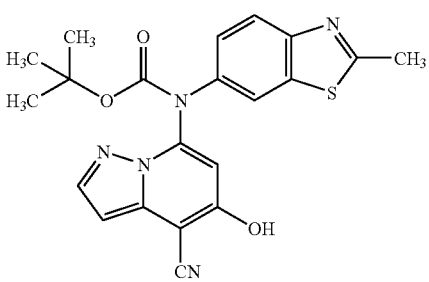

$^1$H-NMR (400 MHz, CDCl$_3$) δ (ppm): 8.03 (d, J=2.0 Hz, 1H), 7.45 (dt, J=8.0, 2.0 Hz, 1H), 7.05 (ddd, J=8.0, 2.0, 1.6 Hz, 1H), 6.61 (d, J=2.0 Hz, 1H), 6.47 (s, 1H), 2.89 (s, 9H). ESI/MS: 422.3 (M$^+$+H, C$_{12}$H$_{19}$N$_5$O$_3$S).

Example 36

(tert-Butoxy)-N-[4-cyano-5-hydroxy(pyrazolo[1,5-a]pyridin-7-yl)]-N-(4-biphenylyl)carboxamide (40)

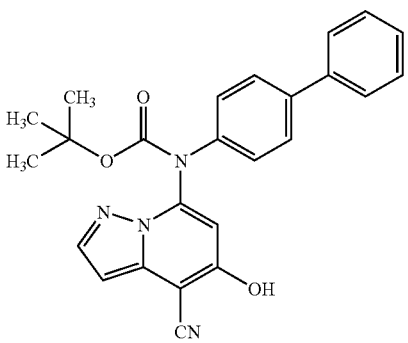

$^1$H-NMR (400 MHz, CDCl$_3$) δ (ppm): 8.01 (d, J=2.0 Hz, 1H), 7.52-7.50 (m, 4H), 7.41-7.35 (m, 5H), 6.87 (s, 1H), 6.58 (d, J=2.0 Hz, 1H), 6.45 (s, 1H), 1.38 (s, 9H). ESI/MS: 427.1 (M$^+$+H, C$_{25}$H$_{22}$N$_4$O$_3$).

Example 37

N-Benzothiazol-6-yl(tert-butoxy)-N-[4-cyano-5-hydroxy-6-methyl(pyrazolo[1 5-a]pyridin-7-yl)]carboxamide (41)

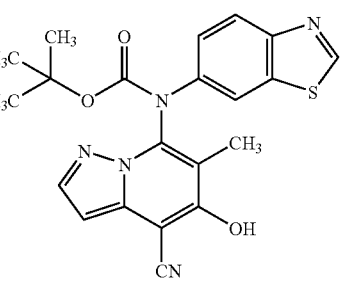

ESI/MS: 422.3 (M$^+$+H, C$_{21}$H$_{19}$N$_5$O$_3$S).

Example 38

Synthesis of tert-butoxy-N-[4-cyano-5-hydroxy-6-(2-hydroxyethyl)pyrazolo[1,5-a]pyridin-7-yl]-N-(4-ethoxyphenyl)carboxamide (42)

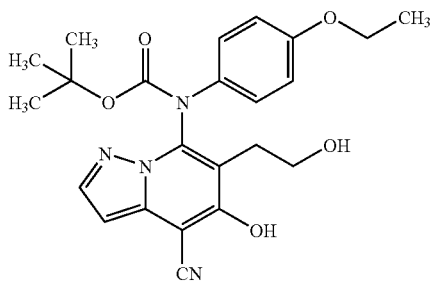

tert-Butoxy-N-[4-cyano-5-hydroxy-6-(2-propenyl)pyrazolo[1,5-a]pyridin-7-yl]-N-(4-ethoxyphenyl)carboxamide (27) (248 mg) was dissolved in a mixture of tetrahydrofuran (4.6 mL) and water (1.1 mL). To this solution, sodium periodate (611 mg) was added and the solution was cooled to 0° C. To this solution, osmium tetroxide (0.58 mL, 2.5 wt. % 2-methyl-2-propanol solution) was added dropwise and the mixture was stirred at room temperature for 2 h. The reaction solution was diluted with ethyl acetate and aqueous sodium thiosulfate solution was added to quench the reaction. After the organic layer was separated, the aqueous layer was extracted with ethyl acetate. The combined organic layers were washed with a mixture of brine and saturated aqueous ammonium chloride solution (9:1) and dried over sodium sulfate. The solvent was removed under reduced pressure and the residue was dissolved in methanol (5.7 mL). Here sodium borohydride (21.6 mg) was added and the solution was stirred at room temperature for 1 h. The reaction solution was diluted with ethyl acetate and washed with brine. The organic layer was dried over sodium sulfate, the solvent was removed under reduced pressure and the resultant crude product was purified with silica-gel column chromatography (hexane/ethyl acetate=2/1 to 1/2) to obtain the title compound (42) (128 mg, Yield 51%).

$^1$H-NMR (400 MHz, CDCl$_3$) δ (ppm): 10.39 (brs, 1H), 7.95 (brs, 1H), 7.12 (d, J=9.0 Hz, 2H), 6.78 (d, J=9.0 Hz, 2H), 6.55 (brs, 1H), 3.96 (q, J=7.0 Hz, 2H), 3.78 (brs, 1H), 3.10 (brs, 1H), 3.04-2.86 (m, 2H), 1.37 (t, J=7.0 Hz, 3H), 1.26 (brs, 9H). ESI/MS: 439.4 (M$^+$+H, C$_{23}$H$_{26}$N$_4$O$_5$).

Example 39

Synthesis of tert-butoxy-N-{4-cyano-5-hydroxy-6-[2-(tert-butyldimethylsilyloxy)ethyl]pyrazolo[1,5-a]pyridin-7-yl}-N-(4-ethoxyphenyl)carboxamide (43)

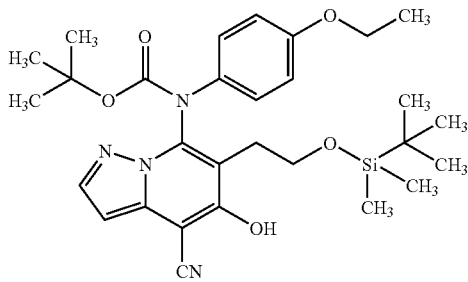

tert-Butoxy-N-[4-cyano-5-hydroxy-6-(2-hydroxyethyl)pyrazolo[1,5-a]pyridin-7-yl]-N-(4-ethoxyphenyl)carboxamide (42) (128 mg) was dissolved in dichloromethane (2.9 mL). To this solution, tert-butyldimethylchlorosilane (110 mg) and imidazole (50 mg) were added and the solution was stirred at room temperature for 3 h. To this reaction solution, methanol (2.9 mL) was added and the solution was further stirred at room temperature for 15 h. The reaction solution was diluted with ethyl acetate and washed with brine. After the organic layer was dried over sodium sulfate, the solvent was removed under reduced pressure and the residue was purified with silica-gel column chromatography (hexane/ethyl acetate=3/1 to 1/1) to obtain the title compound (43) (107.3 mg, Yield 66%).

$^1$H-NMR (400 MHz, CDCl$_3$) δ (ppm): 9.96 (brs, 1H), 7.99 (d, J=1.8 Hz, 1H), 7.12 (d, J=8.8 Hz, 2H), 6.79 (d, J=8.8 Hz, 2H), 6.59 (d, J=1.8 Hz, 1H), 3.97 (m, 2H), 3.76 (brs, 1H), 3.15-2.90 (m, 3H), 1.38 (t, J=6.9 Hz, 3H), 1.26 (brs, 9H), 0.84 (s, 9H), 0.03 (s, 3H), 0.01 (s, 3H). ESI/MS: 553.5 (M$^+$+H, C$_{29}$H$_{40}$N$_4$O$_5$Si).

Example 40

Synthesis of 7-[N-tert-butoxycarbonyl-N-(4-ethoxyphenyl)amino]-4-cyano-6-methylpyrazolo[1,5-a]pyridin-5-yl(trifluoromethyl)sulfonate (44)

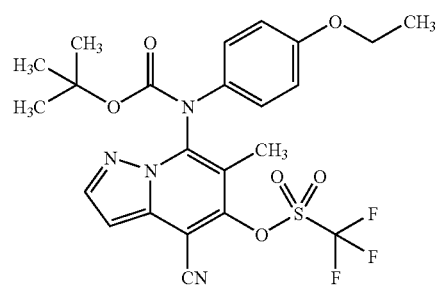

tert-Butoxy-N-(4-cyano-5-hydroxy-6-methylpyrazolo[1,5-a]pyridin-7-yl)-N-(4-ethoxyphenyl)carboxamide (26) (20.4 mg) was dissolved in pyridine (250 μL) and the solution was cooled to 0° C. To this solution, trifluoromethanesulfonic anhydride (12.6 μL) was added dropwise and the mixture was stirred at room temperature for 1 h. The reaction solution was diluted with ethyl acetate and the organic layer was washed with 1 mol/L hydrochloric acid and dried over sodium sulfate. The solvent was removed under reduced pressure to obtain crude product of the title compound (44) (27.0 mg), a part of which was purified with preparative HPLC and the NMR spectrum was recorded.

$^1$H-NMR (400 MHz, CDCl$_3$) δ (ppm): 8.16 (d, J=2.1 Hz, 1H), 7.20 (d, J=8.9 Hz, 2H), 6.94 (d, J=2.1 Hz, 1H), 6.82 (d, J=8.9 Hz, 2H), 3.99 (q, J=7.0 Hz, 2H), 2.33 (s, 3H), 1.39 (t, J=7.0 Hz, 3H), 1.29 (brs, 9H). ESI/MS: 541.2 (M$^+$+H, C$_{23}$H$_{23}$F$_3$N$_4$O$_6$S).

Example 41

Synthesis of tert-butyl(3S)-3-{7-[N-tert-butoxycarbonyl-N-(4-ethoxyphenyl)amino]-4-cyano-6-methylpyrazolo[1,5-a]pyridin-5-ylamino}piperidinecarboxylate (45)

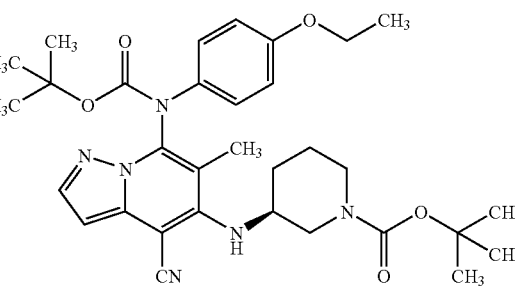

To 7-[N-tert-butoxycarbonyl-N-(4-ethoxyphenyl)amino]-4-cyano-6-methylpyrazolo[1,5-a]pyridin-5-yl(trifluoromethyl)sulfonate (44) (108 mg), tert-butyl(3S)-3-aminopiperidinecarboxylate (801 mg) was added and the mixture was stirred at 100° C. for 1 h.

After cooled to room temperature, the reaction mixture was diluted with ethyl acetate and the organic layer was successively washed with 0.1 mol/L aqueous sodium hydroxide solution, a mixture of brine and 1 mol/L hydrochloric acid (1:1), and then a mixture of brine and saturated aqueous sodium hydrogen carbonate solution (1:1). After the organic layer was dried over sodium sulfate, the solvent was removed under reduced pressure and the residue was purified with silica-gel column chromatography (hexane/ethyl acetate=7/3) to obtain the title compound (45) (5.9 mg, Yield 5%).

$^1$H-NMR (400 MHz, DMSO-d$_6$) δ (ppm): 7.89 (brs, 1H), 7.24-7.12 (m, 2H), 6.90-6.78 (m, 2H), 6.30 (brs, 1H), 5.91 (brs, 1H), 4.21 (brs, 1H), 3.96 (q, J=7.1 Hz, 2H), 3.88-3.52 (m, 2H), 3.40-2.86 (m, 2H), 2.08 (brs, 3H), 1.78-1.65 (m, 2H), 1.50-1.10 (m, 23H). ESI/MS: 591.2 (M$^+$+H, C$_{32}$H$_{42}$N$_6$O$_5$). HPLC retention time: 16.38 min Example 42

Synthesis of N-{5-[(trans-4-aminocyclohexyl)amino]-4-cyano(pyrazolo[1,5-a]pyridin-7-yl)}(tert-butoxy)-N-(4-biphenylyl)carboxamide (46)

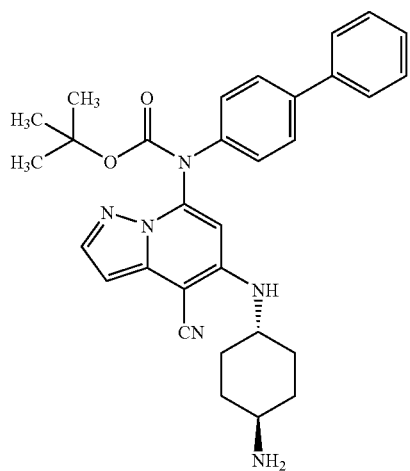

(tert-Butoxy)-N-[4-cyano-5-hydroxy(pyrazolo[1,5-a]pyridin-7-yl)]7-N-(4-biphenylyl)carboxamide (40) (27 mg) was dissolved in 1,4-dioxane (600 μL)and to this solution were added triethylamine (22 μL) and benzotriazol-1-yloxy-tris(pyrrolidino)phosphonium hexafluorophosphate (36 mg). This mixture was stirred at room temperature for 10 min. Trans-1,4-Diaminocyclohexane (145 mg) was added and the mixture was further stirred at room temperature for 4 h. The reaction mixture was diluted with ethyl acetate and the organic layer was washed with 1 mol/L aqueous sodium hydroxide solution, dried over sodium sulfate. The solvent was removed under reduced pressure and the residue was purified with thin layer silica gel column chromatography (ethyl acetate/2 mol/L methanolic ammonia solution=5/1) to obtain the title compound (46).

ESI/MS: 523.2 (M$^+$+H, C$_{31}$H$_{34}$N$_6$O$_2$).

The compounds described below in Examples 43 to 80 were synthesized by either the methods in described in Examples 40 and 41 or the method described in Example 42 using the corresponding starting materials and reagents.

Example 43 tert-Butyl (3S)-3-({7-[tert-butoxy-N-(4-ethoxyphenyl)carbonylamino]-4-cyano-6-(2-propenyl)pyrazolo[1,5-a]pyridin-5-yl}amino)piperidinecarboxylate (47)

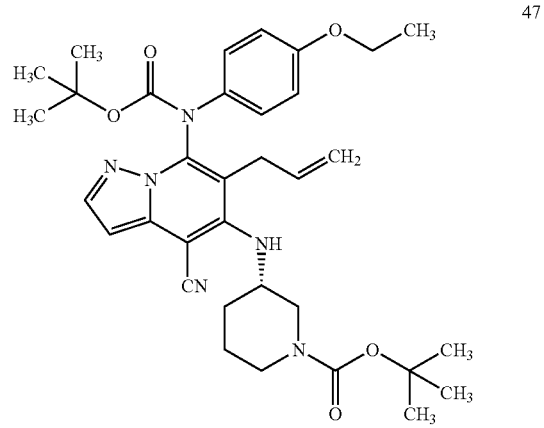

ESI/MS: 617.4 (M$^+$+H, C$_{34}$H$_{44}$N$_6$O$_5$).

Example 44 tert-Butyl (3R)-3-[(7-{tert-butoxy-N-[4-(2-methoxyethoxy)phenyl]carbonylamino}-4-cyano-6-methyl(pyrazolo[1,5-a]pyridin-5-yl))amino]piperidinecarboxylate (48)

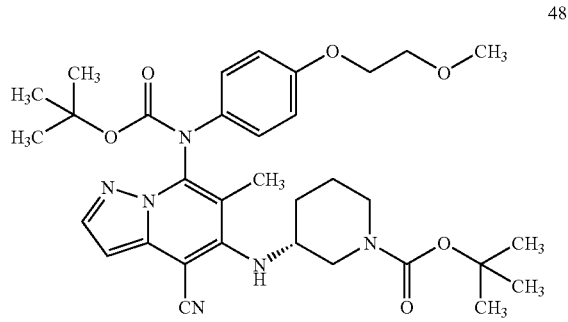

ESI/MS: 621.3 (M$^+$+H, C$_{33}$H$_{44}$N$_6$O$_6$).

Example 45 tert-Butyl (3S)-3-[(7-{tert-butoxy-N-[4-(2-methoxyethoxy)phenyl]carbonylamino}-4-cyano-6-methyl(pyrazolo[1,5-a]pyridin-5-yl))amino]piperidinecarboxylate (49)

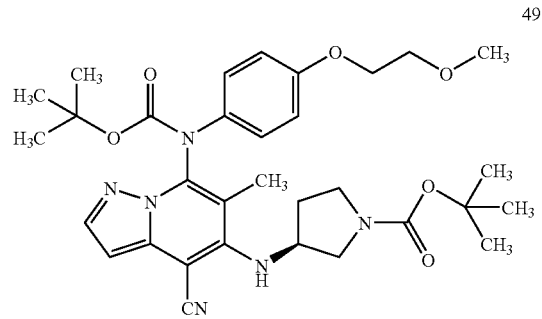

ESI/MS: 607.3 (M$^+$+H, C$_{32}$H$_{42}$N$_6$O$_6$).

Example 46

N-{5-[trans-(4-Aminocyclohexyl)amino]-4-cyano-6-methyl(pyrazolo[1,5-a]pyridin-7-yl)}(tert-butoxy)-N-[4-(2-methoxyethoxy)phenyl]carboxamide (50)

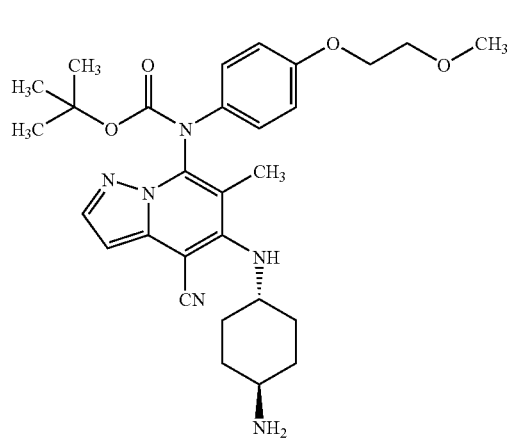

ESI/MS: 535.3 (M$^+$+H, C$_{29}$H$_{38}$N$_6$O$_4$).

Example 47 tert-Butyl (3S)-3-({7-[(tert-butoxy)-N-(2-methylbenzothiazol-6-yl)carbonylamino]-4-cyano-6-methyl(pyrazolo[1,5-a]pyridin-5-yl)}amino)piperidinecarboxylate (51)

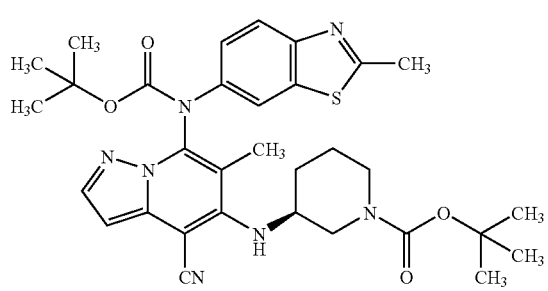

ESI/MS: 618.2 (M$^+$+H, C$_{32}$H$_{39}$N$_7$O$_4$S).

Example 48 tert-Butyl (3S)-3-{7-[N-tert-butoxycarbonyl-N-(4-ethoxyphenyl)amino]-4-cyano-6-pheylpyrazolo[1,5-a]pyridin-5-ylamino}piperidinecarboxylate (52)

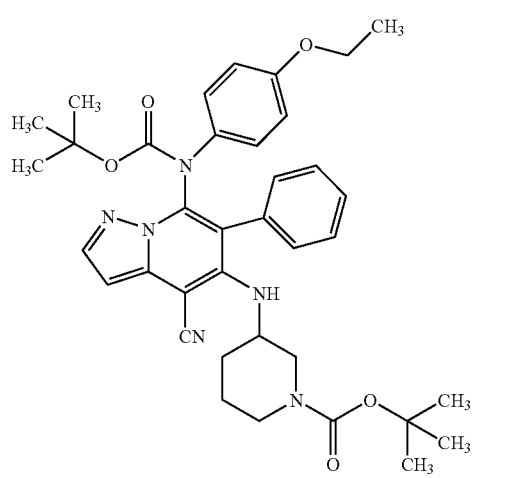

ESI/MS: 653.5 (M$^+$+H, C$_{37}$H$_{44}$N$_6$O$_5$).

Example 49 tert-Butyl (3S)-3-{7-[N-tert-butoxycarbonyl-N-(4-ethoxphenyl)amino]-4-cyano-6-ethylpyrazolo[1,5-a]pyridin-5-ylamino}piperidinecarboxylate (53)

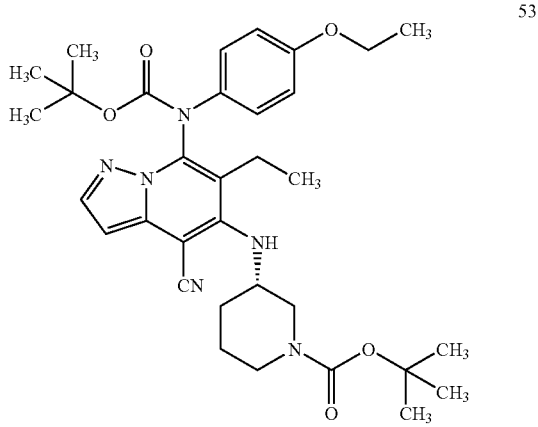

ESI/MS: 605.5 (M$^+$+H, C$_{33}$H$_{44}$N$_6$O$_5$).

Example 50

N-{5-[(trans-4-Aminocyclohexyl)amino]-4-cyano-6-ethyl(pyrazolo[1,5-a]pyridin-7-yl)}(tert-butoxy)-N-(4-ethoxyphenyl)carboxamide (54)

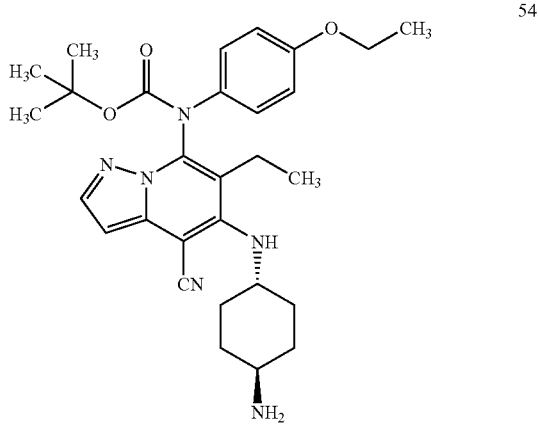

ESI/MS: 519.5 (M$^+$+H, C$_{29}$H$_{38}$N$_6$O$_3$).

Example 51 tert-Butyl (3S)-3-{7-[N-tert-butoxycarbonyl-N-(4-ethoxphenyl)amino]-4-cyano-6-propylpyrazolo[1,5-a]pyridin-5-ylamino}piperidinecarboxylate (55)

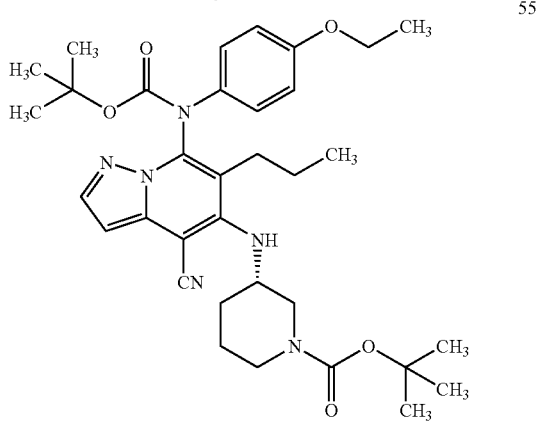

ESI/MS: 619.6 (M$^+$+H, C$_{34}$H$_{46}$N$_6$O$_5$).

Example 52

N-{5-[(trans-4-Amninocyclohexyl)amino]-4-cyano-6-propyl(pyrazolo[1,5-a]pyridin-7-yl)}(tert-butoxy)-N-(4-ethoxyphenyl)carboxamide (56)

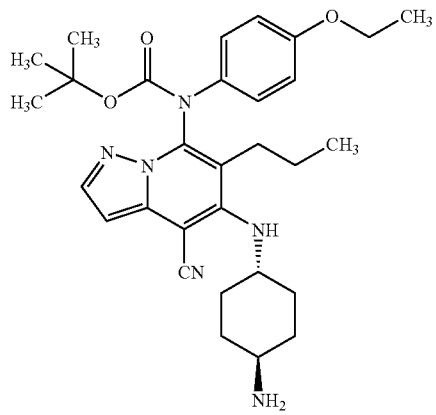

ESI/MS: 533.6 (M$^+$+H, C$_{30}$H$_{40}$N$_6$O$_3$).

Example 53 tert-Butyl (3S)-3-{7-[N-tert-butoxycarbonyl-N-(4-ethoxphenyl)amino]-4-cyano-6-(methylethyl)pyrazolo[1,5-a]pyridin-5-ylamino}piperidinecarboxylate (57)

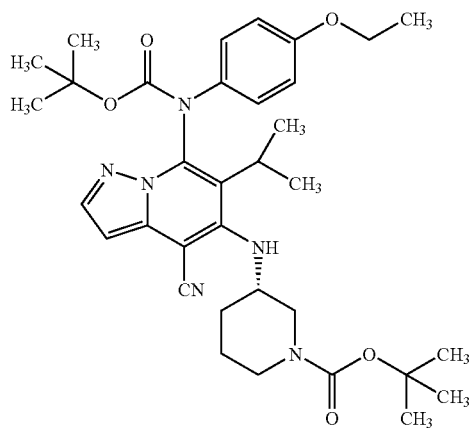

ESI/MS: 619.7 (M$^+$+H, C$_{34}$H$_{46}$N$_6$O$_5$).

Example 54

N-{5-[(trans-4-Aminocyclohexyl)amino]-4-cyano-6-(methylethyl)(pyrazolo[1,5-a]pyridin-7-yl)}(tert-butoxy)-N-(4-ethoxyphenyl)carboxamide (58)

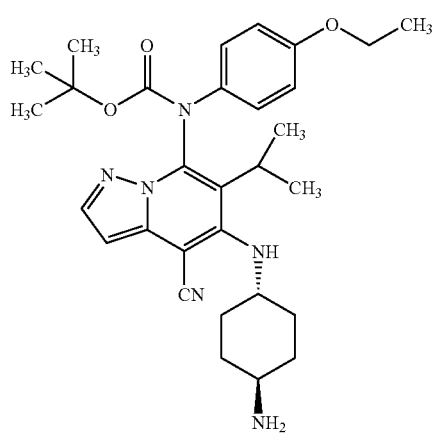

ESI/MS: 533.5 (M$^+$+H, C$_{30}$H$_{40}$N$_6$O$_3$).

Example 55 tert-Butyl (3S)-3-{7-[N-tert-butoxycarbonyl-N-(4-ethoxphenyl)amino]-4-cyano-6-cyclopropylpyrazolo[1,5-a]pyridin-5-ylamino}piperidinecarboxylate (59)

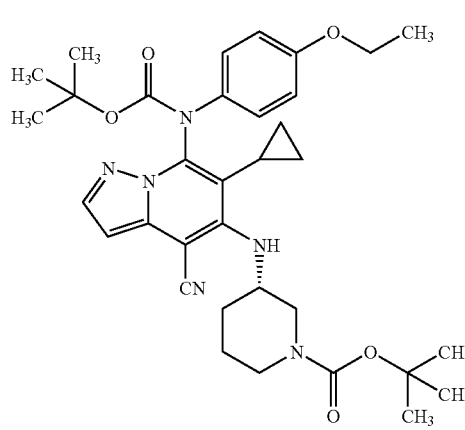

ESI/MS: 617.6 (M$^+$+H, C$_{34}$H$_{44}$N$_6$O$_5$).

Example 56

N-{5-[(trans-4-Aminocyclohexyl)amino]-4-cyano-6-cyclopropyl(pyrazolo[1,5-a]pyridin-7-yl)}(tert-butoxy)-N-(4-ethoxyphenyl)carboxamide (60)

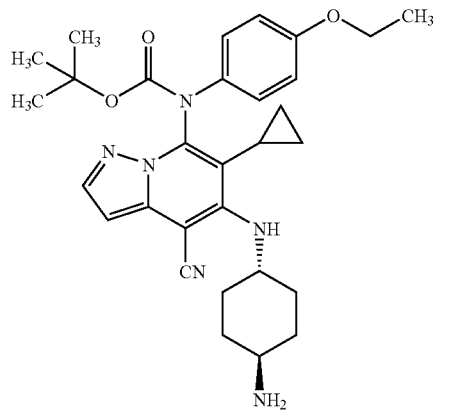

ESI/MS: 531.6 (M$^+$+H, C$_{30}$H$_{38}$N$_6$O$_3$).

Example 57

(tert-Butoxy)-N-(2-chlorophenyl)-N-[4-cyano-5-((3S)-3-piperidylamino)(pyrazolo[1,5a]pyridin-7-yl)]carboxamide (61)

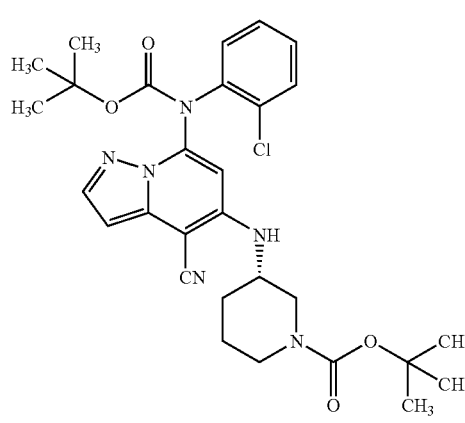

ESI/MS: 567.4 (M$^+$+H, C$_{29}$H$_{35}$ClN$_6$O$_4$).

Example 58

N-{5-[(trans-4-Aminocyclohexyl)amino]-4-cyano(pyrazolo[1,5-a]pyridin-7-yl)}(tert-butoxy)-N-(2-chlorophenyl)carboxamide (62)

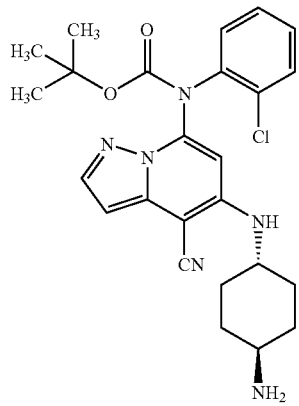

ESI/MS: 481.4 (M$^+$+H, C$_{25}$H$_{29}$ClN$_6$O$_2$).

Example 59

(tert-Butoxy)-N-[5-({trans-4-[(tert-butoxy)carbonylamino]cyclohexyl}amino)-4-cyano(pyrazolo[1,5-a]pyridin-7-yl)]-N-(2-methylbenzothiazol-6-yl)carboxamide (63)

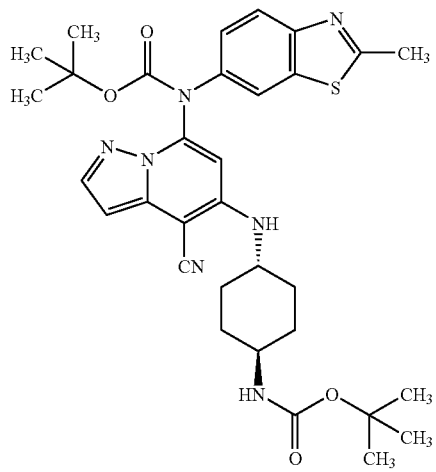

ESI/MS: 618.5 (M$^+$+H, C$_{32}$H$_{39}$N$_7$O$_4$S).

Example 60

N-{5-[(trans-4-Aminocyclohexyl)amino]-4-cyano(pyrazolo[1,5-a]pyridin-7-yl)}(tert-butoxy)-N-(2-methoxyphenyl)carboxamide (64)

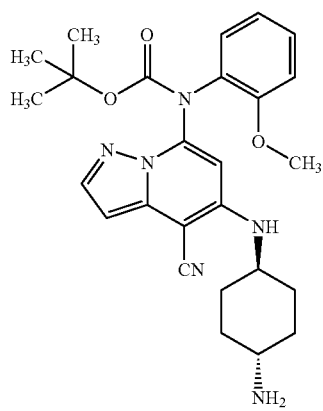

ESI/MS: 477.2 (M$^+$+H, C$_{26}$H$_{32}$N$_6$O$_3$).

Example 61

N-{5-[(trans-4-Aminocyclohexyl)amino]-4-cyano(pyrazolo[1,5-a]pyridin-7-yl)}(tert-butoxy)-N-(2-methylthio)(phenyl)carboxamide (65)

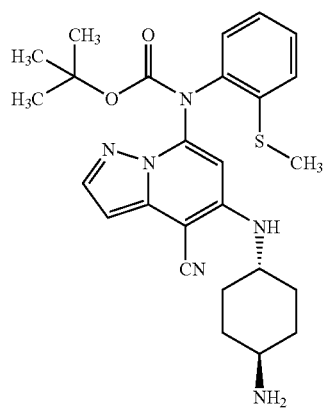

ESI/MS: 493.3 (M$^+$+H, C$_{26}$H$_{32}$N$_6$O$_2$S).

Example 62

(tert-Butoxy)-N-[4-cyano-5-((3S)-3-piperidylamino)(pyrazolo[1,5-a]pyridin-7-yl)]-N-(4biphenylyl)carboxamide (66)

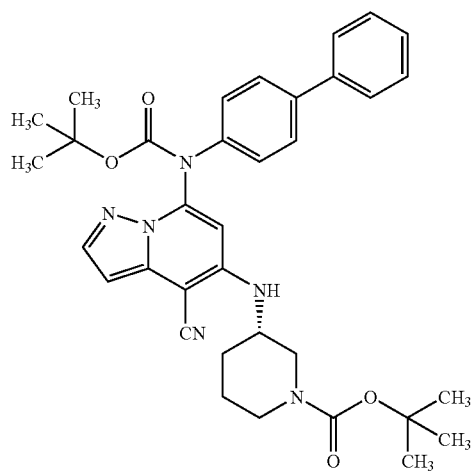

ESI/MS: 609.6 (M$^+$+H, C$_{35}$H$_{40}$N$_6$O$_4$).

Example 63

N-{5-[(trans-2-Aminocyclohexyl)amino]-4-cyano-6-methyl(pyrazolo[1,5-a]pyridin-7-yl)}(tert-butoxy)-N-(4-ethoxyphenyl)carboxamide (67)

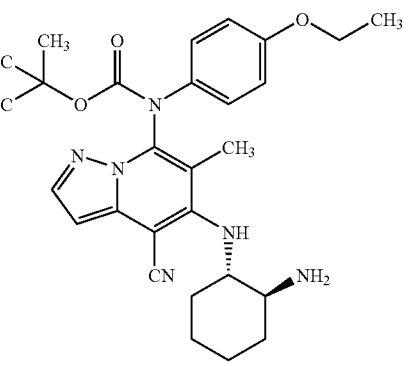

ESI/MS: 505.6 (M$^+$+H, C$_{28}$H$_{36}$N$_6$O$_3$).

Example 64

(tert-Butoxy)-N-[4-cyano-6-methyl-5-(4-piperidylamino)(pyrazolo[1,5-a]pyridin-7-yl)]-N-(4-ethoxyphenyl)carboxamide (68)

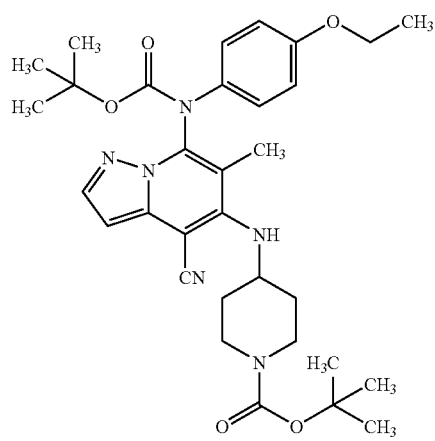

ESI/MS: 591.6 (M$^+$+H, C$_{32}$H$_{42}$N$_6$O$_5$).

Example 65

N-{5-[(3-Aminocyclohexyl)amino]-4-cyano-6-methyl(pyrazolo[1,5-a]pyridin-7-yl)}(tert-butoxy)-N-(4-ethoxyphenyl)carboxamide (69)

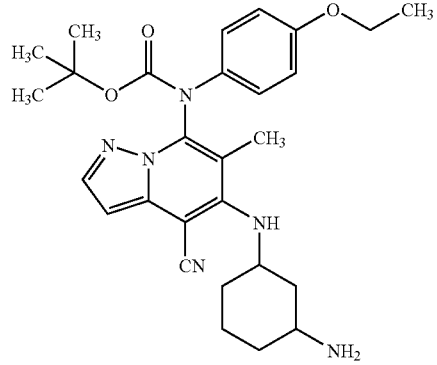

ESI/MS: 505.6 (M$^+$+H, C$_{28}$H$_{36}$N$_6$O$_3$).

Example 66

N-{5-[(2-Aminoethyl)amino]-4-cyano-6-methyl(pyrazolo[1,5-a]pyridin-7-yl)}(tert-butoxy)-N-(4-ethoxyphenyl)carboxamide (70)

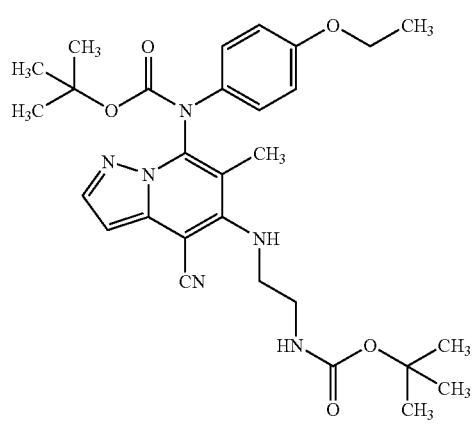

ESI/MS: 551.6 (M$^+$+H, C$_{29}$H$_{38}$N$_6$O$_5$).

Example 67

N-{5-[(3-Aminopropyl)amino]-4-cyano-6-methyl(pyrazolo[1,5-a]pyridin-7-yl)}(tert-butoxy)-N-(4-ethoxyphenyl)carboxamide (71)

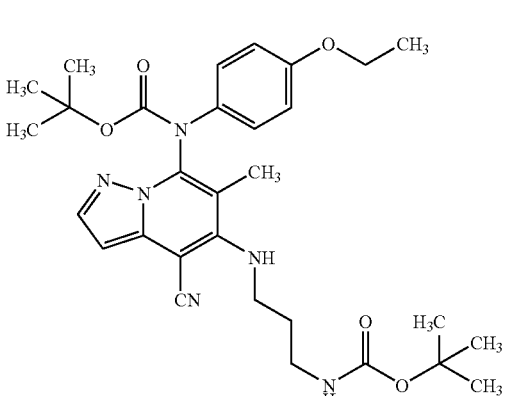

ESI/MS: 565.5 (M$^+$+H, C$_{30}$H$_{40}$N$_6$O$_5$).

Example 68

N-{5-[(4-Aminobutyl)amino]-4-cyano-6-methyl(pyrazolo[1,5-a]pyridin-7-yl)}(tert-butoxy)-N-(4-ethoxyphenyl)carboxamide (72)

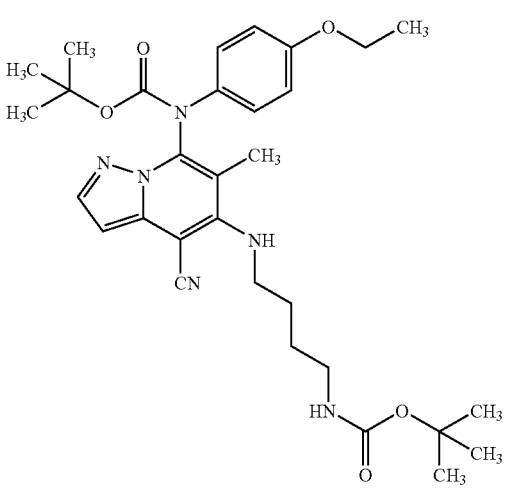

ESI/MS: 579.6 (M$^+$+H, C$_{31}$H$_{42}$N$_6$O$_5$).

Example 69

(tert-Butoxy)-N-{4-cyano-6-methyl-5-[(pyrrolidin-3-ylmethyl)amino](pyrazolo[1,5-a]pyridin-7-yl)}-N-(4-ethoxyphenyl)carboxamide (73)

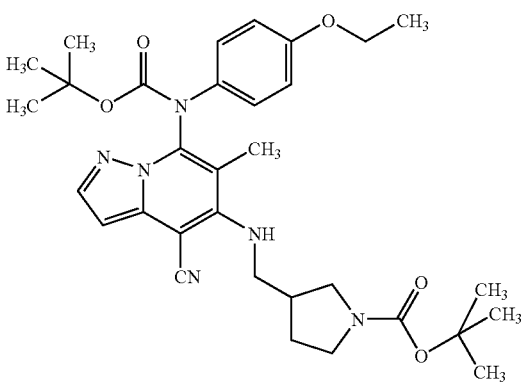

ESI/MS: 591.6 (M$^+$+H, C$_{32}$H$_{42}$N$_6$O$_5$).

Example 70

(tert-Butoxy)-N-(4-cyano-6-methyl-5-{[2-(2-piperidyl)ethyl]amino}(pyrazolo[1,5-a]pyridin-7-yl))-N-(4-ethoxyphenyl)carboxamide (74)

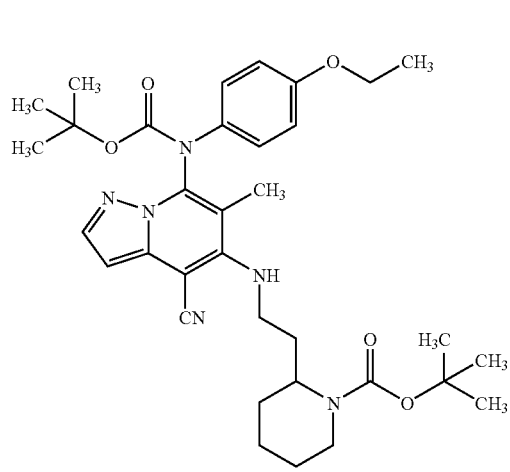

ESI/MS: 619.6 (M$^+$+H, C$_{34}$H$_{46}$N$_6$O$_5$).

Example 71

(tert-Butoxy)-N-{4-cyano-6-methyl-5-[(pyrrolidin-2-ylmethyl)amino](pyrazolo[1,5-a]pyridin-7-yl)}-N-(4-ethoxyphenyl)carboxamide (75)

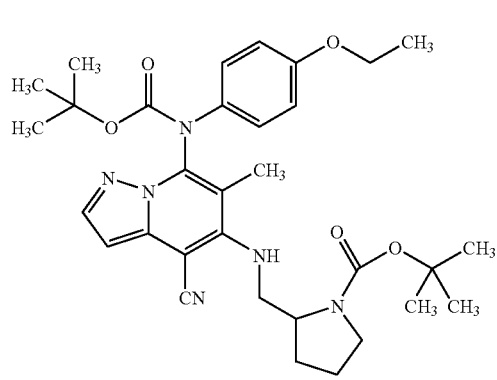

ESI/MS: 591.5 (M$^+$+H, C$_{32}$H$_{42}$N$_6$O$_5$).

Example 72

(tert-Butoxy)-N-{4-cyano-6-methyl-5-[(2-piperidylmethyl)amino](pyrazolo[1,5-a]pyridin-7-yl)}-N-(4-ethoxyphenyl)carboxamide (76)

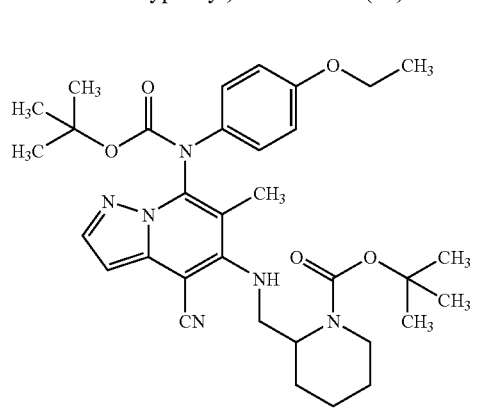

ESI/MS: 605.5 (M$^+$+H, C$_{33}$H$_{44}$N$_6$O$_5$).

Example 73

(tert-Butoxy)-N-{4-cyano-5-{[3-(cyclohexylamino)propyl]amino}-6-methyl(pyrazolo[1,5-a]pyridin-7-yl)}-N-(4-ethoxyphenyl)carboxamide (77)

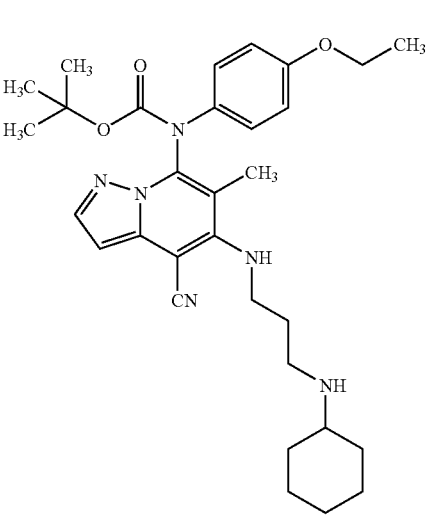

ESI/MS: 547.6 (M$^+$+H, C$_{32}$H$_{42}$N$_6$O$_3$).

Example 74

(tert-Butoxy)-N-{4-cyano-6-methyl-5-[(3-piperidylmethyl)amino]pyrazolo[1,5-a]pyridin-7-yl}-N-(4-ethoxyphenyl)carboxamide (78)

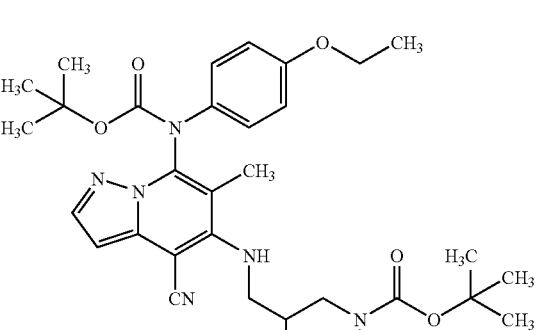

ESI/MS: 605.7 (M$^+$+H, C$_{33}$H$_{44}$N$_6$O$_5$).

Example 75

(tert-Butoxy)-N-{4-cyano-6-methyl-5-[2-(pyrrolidin-2-ylethyl)amino](pyrazolo[1,5-a]pyridin-7-yl)}-N-(4-ethoxyphenyl)carboxamide (79)

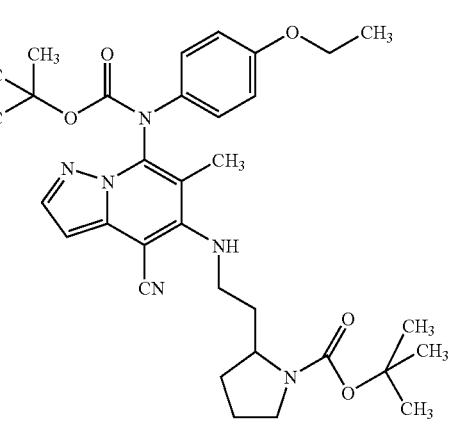

ESI/MS: 605.6 (M$^+$+H, C$_{33}$H$_{44}$N$_6$O$_5$).

Example 76

N-{5-[(6-Aminohexyl)amino]-4-cyano-6-methyl(pyrazolo[1,5-a]pyridin-7-yl)}(tert-butoxy)-N-(4-ethoxyphenyl)carboxamide (80)

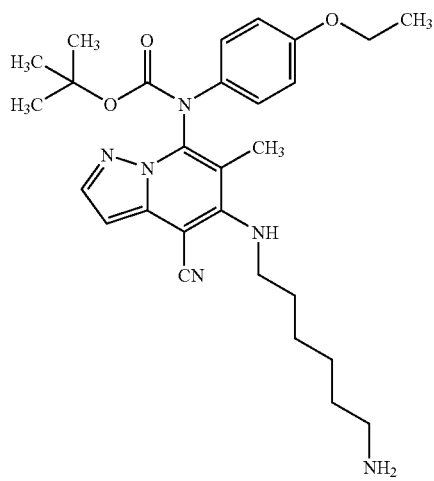

ESI/MS: 507.6 (M$^+$+H, C$_{28}$H$_{38}$N$_6$O$_3$).

Example 77

(tert-Butoxy)-N-{4-cyano-6-methyl-5-{[2-(1-methylpyrrolidin-2-yl)ethyl]amino}(pyrazolo[1,5-a]pyridin-7-yl)}-N-(4-ethoxyphenyl)carboxamide (81)

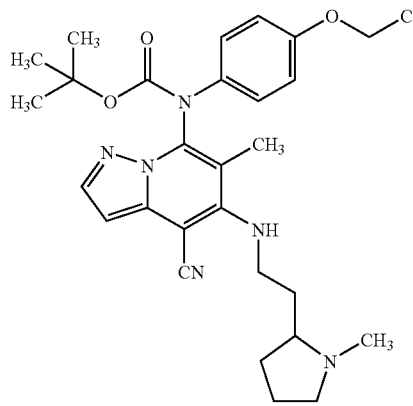

ESI/MS: 519.5 (M$^+$+H, C$_{29}$H$_{38}$N$_6$O$_3$).

Example 78 tert-Butyl (3S)-3-({7-[N-benzothiazol-6-yl(tert-butoxy)carbonylamino]-4-cyano-6-methyl(pyrazolo[1,5-a]pyridin-5-yl)}amino)piperidinecarboxylate (82)

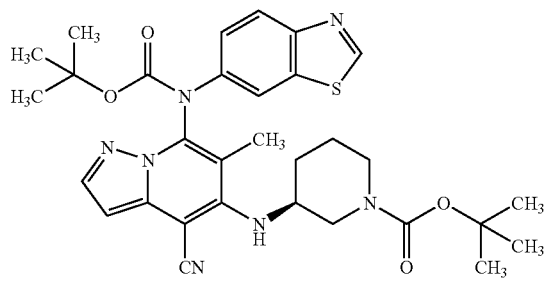

ESI/MS: 604.5 (M$^+$+H, C$_{31}$H$_{37}$N$_7$O$_4$S).

Example 79 tert-Butyl (3S)-3-({7-[(tert-butoxy)-N-(2-ethylbenzothiazol-6-yl)carbonylamino]-4-cyano-6-methyl(pyrazolo[1,5-a]pyridin-5-yl)}amino)piperidinecarboxylate (83)

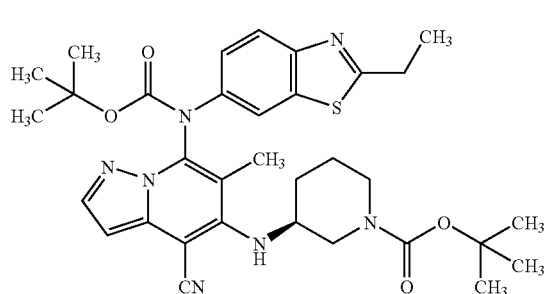

ESI/MS: 632.6 (M$^+$+H, C$_{33}$H$_{41}$N$_7$O$_4$S).

Example 80 tert-Butyl 4-({7-[(tert-butoxy)-N-(4-ethoxyphenyl)carbonylamino]-4-cyano-6-methylpyrazolo[1,5-a]pyridin-5-yl}amino)-1,2,3,4-tetrahydroisoquinoline-2-carboxylate (84)

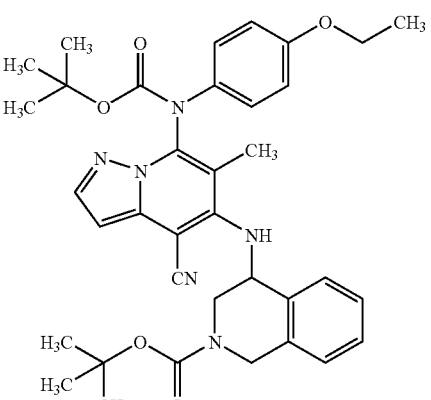

ESI/MS: 639.5 (M$^+$+H, C$_{36}$H$_{42}$N$_6$O$_5$).

Example 81

Synthesis of 5-[(3S)-3-piperidylamino]-7-(4-ethoxyphenylamino)-6-methylpyrazolo[1,5-a]pyridine-4-carbonitrile (85)

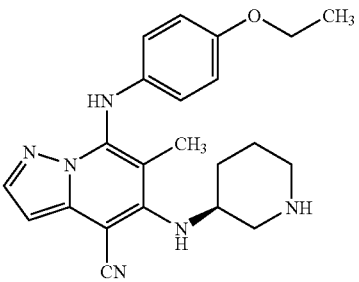

The crude product of tert-butyl (3S)-3-{7-[N-tert-butoxycarbonyl-N-(4-ethoxyphenyl)amino]-4-cyano-6-methylpyrazolo[1,5-a]pyridin-5-ylamino}piperidinecarboxylate (45) (6.1 mg) was dissolved in dichloromethane (350 μL). To this solution, trifluoroacetic acid (150 μL) was added and the mixture was stirred at room temperature for 1 h. The solvent and trifluoroacetic acid were removed under reduced pressure and the residue was purified with preparative HPLC to obtain the title compound (85) as trifluoroacetate salt (1.81 mg, Yield 24%).

The obtained trifluoroacetate salt of the title compound (85) was dissolved in methanol and the solution was charged on a strongly acidic cation exchange resin SCX cartridge. The resin was washed with methanol and then the desired material was eluted with 0.1 mol/L ammonia/methanol solution. The solvent was removed under reduced pressure to obtain the title compound (85) as a free base.

$^1$H-NMR (400 MHz, CDCl$_3$) δ (ppm): 7.79 (d, J=2.1 Hz, 1H), 7.67 (s, 1H), 6.94 (d, J=8.9 Hz, 2H), 6.85 (d, J=8.9 Hz, 2H), 6.38 (d, J=2.1 Hz, 1H), 5.37 (brs, 1H), 4.41 (brs, 1H), 4.02 (q, J=7.0 Hz, 2H), 3.09 (dd, J=11.6, 2.6 Hz, 1H), 2.93-2.87 (m, 2H), 2.77 (td, J=15.0, 5.4 Hz, 1H), 2.00-1.50 (m, 4H), 1.81 (s, 3H), 1.42 (t, J=7.0 Hz, 3H). ESI/MS: 391.2 (M$^+$+H, C$_{22}$H$_{26}$N$_6$O). HPLC retention time: 9.34 min Compounds described below in Examples 82 to 129 were synthesized by the method described in Example 81 using the corresponding starting materials and reagents.

Example 82

5-[(3S)-3-Piperidylamino]-7-(4-ethoxyphenylamino)-6-(2-propenyl)pyrazolo[1,5-a]pyridine-4-carbonitrile trifluoroacetate salt (86)

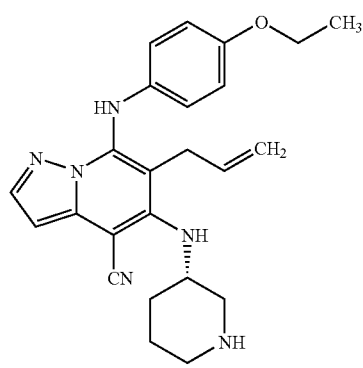

$^1$H-NMR (400 MHz, DMSO-d$_6$) δ (ppm): 8.76 (brs, 1H), 8.63 (brs, 1H), 8.59 (brs, 1H), 7.88 (d, J=2.1 Hz, 1H), 6.90-6.79 (m, 4H), 6.30 (d, J=2.1 Hz, 1H), 5.70 (d, J=9.3 Hz, 1H), 5.68-5.50 (m, 1H), 4.97-4.84 (m, 2H), 4.40-4.28 (m, 1H), 3.96 (q, J=7.1 Hz, 2H), 3.40-3.15 (m, 4H), 2.99-2.86 (m, 1H), 2.83-2.70 (m, 1H), 2.20-2.10 (m, 1H), 1.93-1.82 (m, 1H), 1.76-1.63 (m, 1H), 1.62-1.48 (m, 1H), 1.29 (t, J=7.1 Hz, 3H). ESI/MS: 417.2 (M$^+$+H, C$_{24}$H$_{28}$N$_6$O). HPLC retention time: 10.17 min Example 83

5-[(3S)-3-Piperidylamino]-7-[4-(2-methoxyethoxy) phenylamino]-6-methylpyrazolo[1,5-a]pyridine-4-carbonitrile trifluoroacetate salt (87)

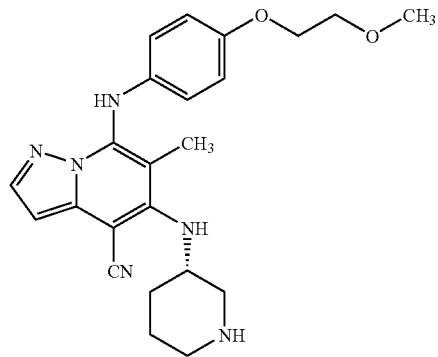

$^1$H-NMR (400 MHz, DMSO-d$_6$) δ (ppm): 8.82 (s, 1H), 8.79 (brs, 1H), 8.61 (brs, 1H), 7.90 (d, J=2.2 Hz, 1H), 6.90-6.85 (m, 4H), 6.30 (d, J=2.2 Hz, 1H), 5.86 (d, J=9.3 Hz, 1H), 4.31 (brs, 1H), 4.03 (t, J=4.6 Hz, 2H), 3.63 (t, J=4.6 Hz, 2H), 3.40 (d, J=11.0 Hz, 1H), 3.29 (s, 3H), 3.23 (d, J=12.0 Hz, 1H), 3.07-2.99 (m, 1H), 2.78 (d, J=11.0 Hz, 1H), 2.17 (d, J=12.0 Hz, 1H), 1.88 (brs, 1H), 1.75 (s, 3H), 1.75-1.60 (m, 2H). ESI/MS: 421.3 (M$^+$+H, C$_{23}$H$_{28}$N$_6$O$_2$). HPLC retention time: 8.17 min Example 84

5-[(3S)-3-Pyrrolidylamino]-7-[4-(2-methoxyethoxy) phenylamino]-6-methylpyrazolo[1,5-a]pyridine-4-carbonitrile trifluoroacetate salt (88)

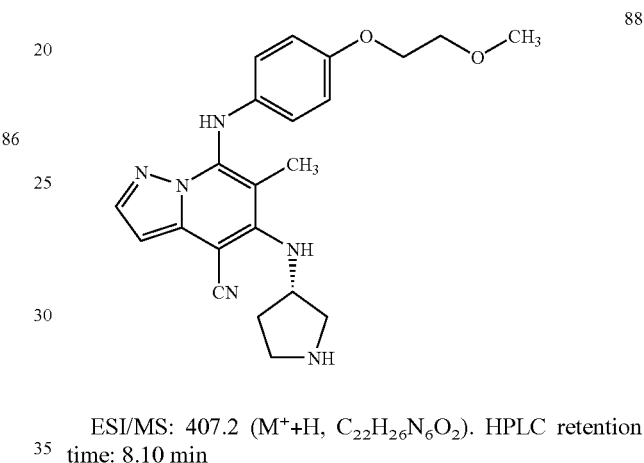

ESI/MS: 407.2 (M$^+$+H, C$_{22}$H$_{26}$N$_6$O$_2$). HPLC retention time: 8.10 min Example 85

5-(trans-4-Aminocyclohexylamino)-7-[4-(2-methoxyethoxy)phenylamino]-6-methylpyrazolo[1,5-a] pyridine-4-carbonitrile trifluoroacetate salt (89)

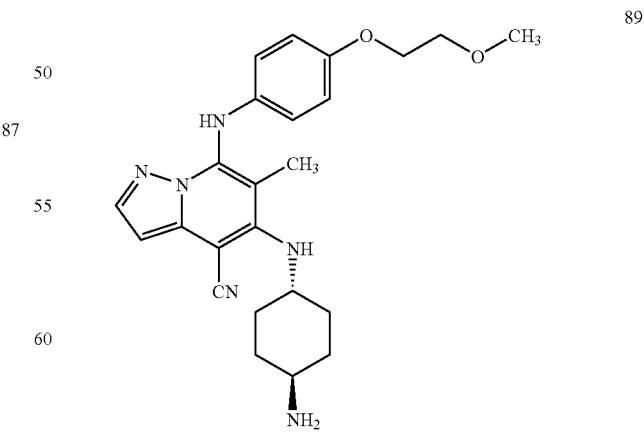

ESI/MS: 435.3 (M$^+$+H, C$_{24}$H$_{30}$N$_6$O$_2$). HPLC retention time: 8.41 min

Example 86

5-[(3S)-3-Piperidylamino]-7-(4-ethoxyphenylamino)-6-(2-hydroxyethyl)pyrazolo[1,5-a]pyridine-4-carbonitrile (90)

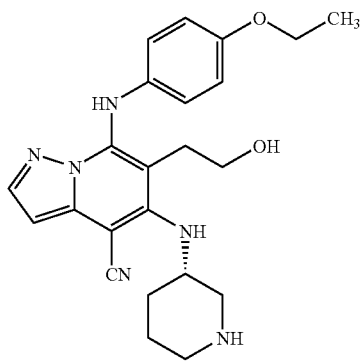

$^1$H-NMR (400 MHz, DMSO-d$_6$) δ (ppm): 8.32 (s, 1H), 7.78 (d, J=2.0 Hz, 1H), 6.82-6.73 (m, 4H), 6.61 (d, J=8.5 Hz, 1H), 6.19 (d, J=2.0 Hz, 1H), 5.23 (brs, 1H), 4.17-4.08 (m, 1H), 3.94 (q, J=7.0 Hz, 2H), 3.40-3.30 (m, 2H), 3.08-3.01 (m, 1H), 2.78-2.71 (m, 1H), 2.67-2.51 (m, 4H), 2.03-1.94 (m, 1H), 1.67-1.35 (m, 3H), 1.28 (t, J=7.0 Hz, 3H). ESI/MS: 421.3 (M$^+$+H, C$_{23}$H$_{28}$N$_6$O$_2$). HPLC retention time: 8.29 min

Example 87

5-[(3S)-3-Piperidylamino]-7-(2-methylbenzothiazol-6-ylamino)-6-methylpyrazolo[1,5-a]pyridine-4-carbonitrile (91)

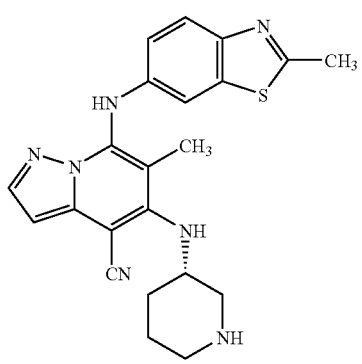

$^1$H-NMR (400 MHz, DMSO-d$_6$) δ (ppm): 9.10 (s, 1H), 7.87 (d, J=2.1 Hz, 1H), 7.76 (d, J=8.8 Hz, 1H), 7.35 (d, J=2.4 Hz, 1H), 7.10 (dd, J=8.8, 2.4 Hz, 1H), 6.29 (d, J=2.1 Hz, 1H), 5.94 (d, J=9.0 Hz, 1H), 4.27-4.25 (m, 1H), 3.18 (d, J=9.0 Hz, 1H), 2.94 (d, J=12.0 Hz, 1H), 2.85 (dd, J=12.0, 9.0 Hz, 1H), 2.72 (s, 3H), 2.69-2.64 (m, 1H), 2.03 (brs, 1H) 1.85 (s, 3H), 1.74-1.54 (m, 3H). ESI/MS: 418.2 (M$^+$+H, C$_{22}$H$_{23}$N$_7$S). HPLC retention time: 7.80 min

Example 88

5-[(3S)-3-Piperidylamino]-7-(4-ethoxyphenylamino)pyrazolo[1,5-a]pyridine-4-carbonitrile trifluoroacetate salt (92)

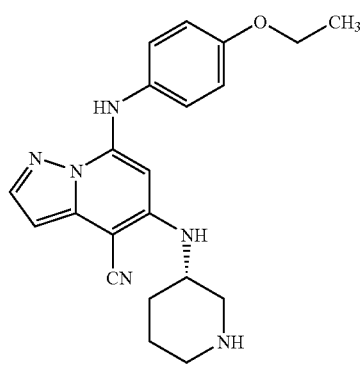

ESI/MS: 377.2 (M$^+$+H, C$_{21}$H$_{24}$N$_6$O). HPLC retention time: 8.49 min

Example 89

5-[(3S)-3-Piperidylamino]-7-(2-chlorophenylamino)pyrazolo[1,5-a]pyridine-4-carbonitrile trifluoroacetate salt (93)

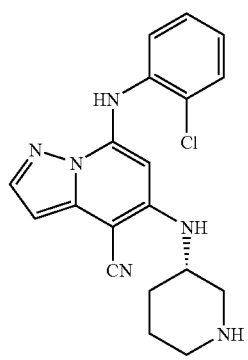

ESI/MS: 367.1 (M$^+$+H, C$_{19}$H$_{19}$ClN$_6$). HPLC retention time: 10.91 min

Example 90

5-(trans-4-Aminocyclohexylamino)-7-(2-chlorophenylamino)pyrazolo[1,5-a]pyridine-4-carbonitrile trifluoroacetate salt (94)

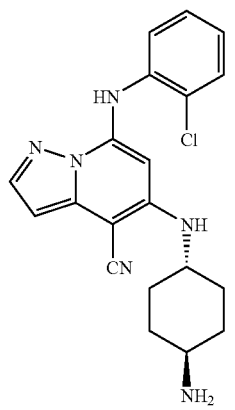

ESI/MS: 381.2 (M$^+$+H, C$_{20}$H$_{21}$ClN$_6$). HPLC retention time: 8.81 min

Example 91

5-(3-Piperidylamino)-7-(4-ethoxyphenylamino)-6-phenylpyrazolo[1,5-a]pyridine-4-carbonitrile trifluoroacetate salt (95)

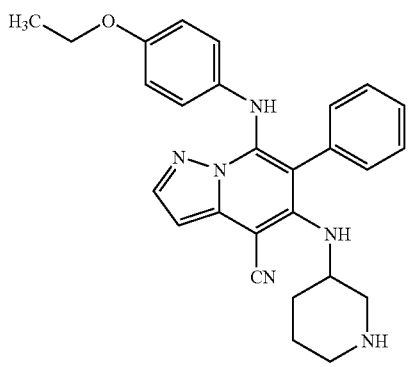

ESI/MS: 453.3 (M$^+$+H, C$_{27}$H$_{28}$N$_6$O). HPLC retention time: 9.80 min

Example 92

5-(trans-4-Aminocyclohexylamino)-7-(2-methylbenzothiazol-6-ylamino)pyrazolo[1,5-a]pyridine-4-carbonitrile trifluoroacetate salt (96)

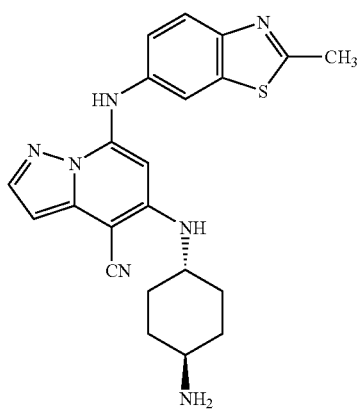

ESI/MS: 418.2 (M$^+$+H, C$_{22}$H$_{23}$N$_7$S). HPLC retention time: 8.06 min

Example 93

5-(trans-4-Aminocyclohexylamino)-7-(4-biphenylylamino)pyrazolo[1,5-a]pyridine-4-carbonitrile trifluoroacetate salt (97)

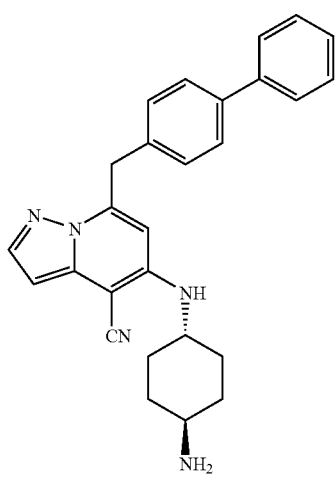

ESI/MS: 423.1 (M$^+$+H, C$_{26}$H$_{26}$N$_6$). HPLC retention time: 10.05 min

Example 94

5-(trans-4-Aminocyclohexylamino)-7-(2-methoxyphenylamino)pyrazolo[1,5-a]pyridine-4-carbonitrile trifluoroacetate salt (98)

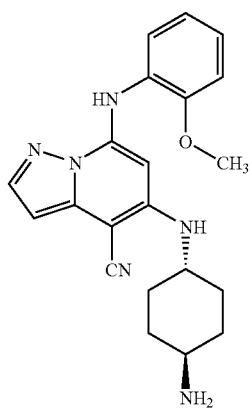

ESI/MS: 377.1 (M$^+$+H, C$_{21}$H$_{24}$N$_6$O). HPLC retention time: 8.87 min

Example 95

5-(trans-4-Aminocyclohexylamino)-7-(2-methylthiophenylamino)pyrazolo[1,5-a]pyridine-4-carbonitrile trifluoroacetate salt (99)

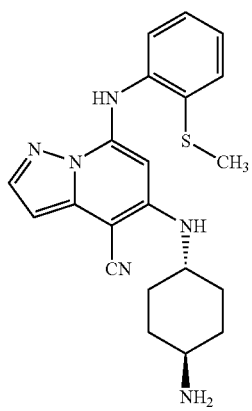

ESI/MS: 390.1 (M$^+$+H, C$_{21}$H$_{24}$N$_6$S). HPLC retention time: 9.12 min

Example 96

5-[(3S)-3-Piperidylamino]-7-(4-biphenylylamino)pyrazolo[1,5-a]pyridine-4-carbonitrile trifluoroacetate salt (100)

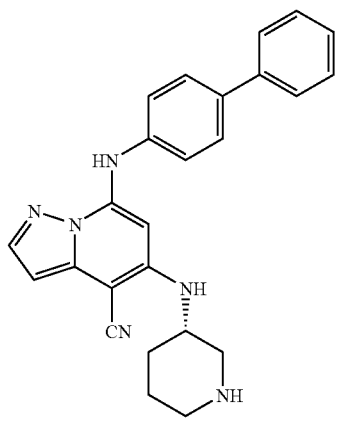

ESI/MS: 409.1 (M$^+$+H, C$_{25}$H$_{24}$N$_6$). HPLC retention time: 9.52 min

Example 97

5-[(trans-2-Aminocyclohexyl)amino]-7-(4-ethoxyphenylamino)-6-methylpyrazolo[1,5-a]pyridine-4-carbonitrile trifluoroacetate salt (101)

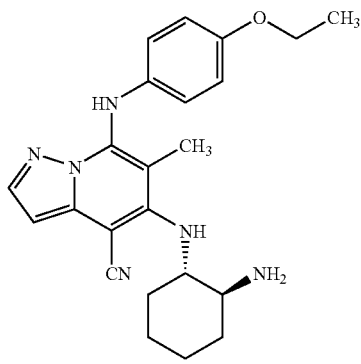

ESI/MS: 405.2 (M$^+$+H, C$_{23}$H$_{28}$N$_6$O). HPLC retention time: 9.37 min

Example 98

5-[(trans-4-Aminocyclohexyl)amino]-7-(4-ethoxyphenylamino)-6-methylpyrazolo[1,5-a]pyridine-4-carbonitrile trifluoroacetate salt (102)

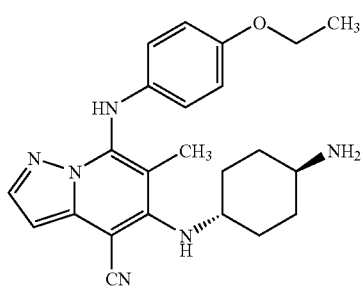

ESI/MS: 405.1 (M$^+$+H, C$_{23}$H$_{28}$N$_6$O). HPLC retention time: 9.94 min

Example 99

7-(4-Ethoxyphenylamino)-6-methyl-5-(4-pyperidylamino)pyrazolo[1,5-a]pyridine-4-carbonitrile trifluoroacetate salt (103)

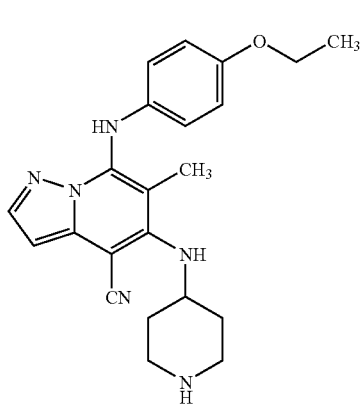

ESI/MS: 391.1 (M$^+$+H, C$_{22}$H$_{26}$N$_6$O). HPLC retention time: 9.49 min

Example 100

5-[(3-Aminocyclohexyl)amino]-7-[(4-ethoxyphenyl)amino]-6-methylpyrazolo[1,5-a]pyridine-4-carbonitrile trifluoroacetate salt (104)

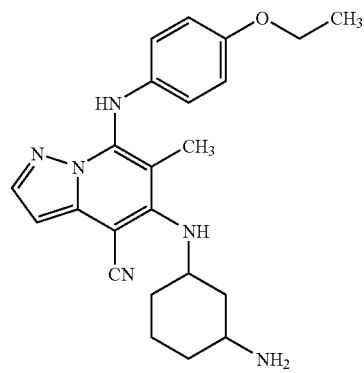

ESI/MS: 405.1 (M$^+$+H, C$_{23}$H$_{28}$N$_6$O). HPLC retention time: 10.04 min

Example 101

5-[(3S)-3-Piperidylamino]-7-(4-ethoxyphenylamino)-6-ethylpyrazolo[1,5-a]pyridine-4-carbonitrile (105)

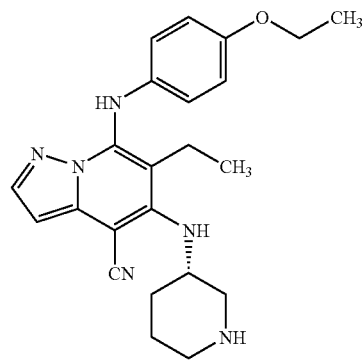

$^1$H-NMR (400 MHz, CDCl$_3$) δ (ppm): 7.78 (d, J=2.2 Hz, 1H), 7.51 (s, 1H), 7.03 (d, J=8.3 Hz, 2H), 6.84 (d, J=8.3 Hz, 2H), 6.36 (d, J=2.2 Hz, 1H), 5.42 (brs, 1H), 4.50-4.47 (m, 1H), 4.01 (q, J=7.0 Hz, 2H), 3.19-3.12 (m, 1H), 2.96-2.87 (m, 2H), 2.87-2.78 (m, 1H), 2.37 (q, J=7.6Hz, 2H), 2.00-1.50 (m, 4H), 1.41 (t, J=7.0Hz, 3H), 0.90 (t, J=7.6 Hz, 3H). ESI/MS: 405.2 (M$^+$+H, C$_{23}$H$_{28}$N$_6$O). HPLC retention time: 9.20 min

Example 102

5-[(2-Aminoethyl)amino]-7-[(4-ethoxyphenyl)amino]-6-methylpyrazolo[1,5-a]pyridine-4-carbonitrile trifluoroacetate salt (106)

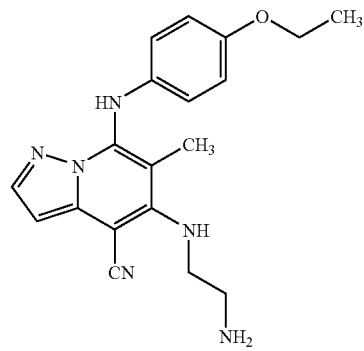

ESI/MS: 351.1 (M$^+$+H, C$_{19}$H$_{22}$N$_6$O). HPLC retention time: 8.41 min

Example 103

5-[(3-Aminopropyl)amino]-7-[(4-ethoxyphenyl)amino]-6-methylpyrazolo[1,5-a]pyridine-4-carbonitrile trifluoroacetate salt (107)

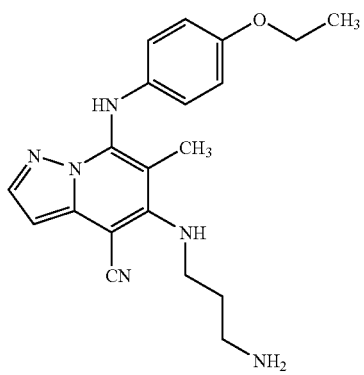

ESI/MS: 365.1 (M$^+$+H, C$_{20}$H$_{24}$N$_6$O). HPLC retention time: 8.60 min

Example 104

5-[(4-Aminobutyl)amino]-7-[(4-ethoxyphenyl)amino]-6-methylpyrazolo[1,5-a]pyridine-4-carbonitrile trifluoroacetate salt (108)

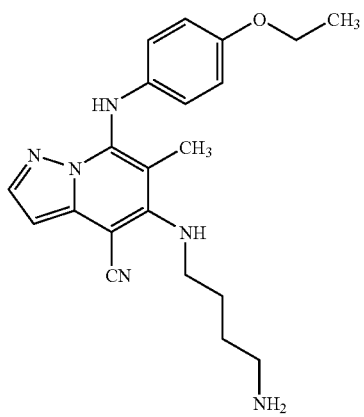

ESI/MS: 379.1 (M$^+$+H, C$_{21}$H$_{26}$N$_6$O). HPLC retention time: 8.88 min

Example 105

5-(trans-4-Aminocyclohexylamino)-7-(4-ethoxyphenylamino)-6-ethylpyrazolo[1,5-a]pyridine-4-carbonitrile (109)

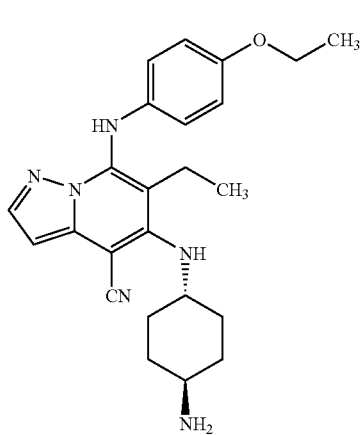

$^1$H-NMR (400 MHz, CDCl$_3$) δ (ppm): 7.78 (d, J=2.2 Hz, 1H), 7.53 (s, 1H), 7.01 (d, J=8.8 Hz, 2H), 6.84 (d, J=8.8 Hz, 2H), 6.37 (d, J=2.2 Hz, 1H), 4.32-4.27 (m, 1H), 4.02 (q, J=7.1 Hz, 2H), 2.34-2.23 (m, 4H), 2.23-1.97 (m, 10H), 1.42 (t, J=7.1 Hz, 3H), 0.85 (t, J=7.6 Hz, 3H). ESI/MS: 419.3 (M$^+$+H, C$_{24}$H$_{30}$N$_6$O). HPLC retention time: 9.38 min

Example 106

7-[(4-Ethoxyphenyl)amino]-6-methyl-5-(trans-{4-[(2-methylpropyl)amino]cyclohexyl}amino)pyrazolo[1,5-a]pyridine-4-carbonitrile trifluoroacetate salt (110)

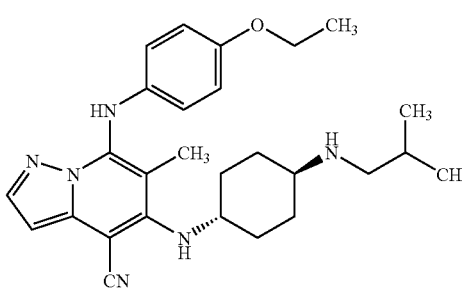

ESI/MS: 461.2 (M$^+$+H, C$_{27}$H$_{36}$N$_6$O). HPLC retention time: 10.25 min

Example 107

5-[((3S)-(3-Piperidyl))amino]-6-methyl-7-(phenylamino)pyrazolo[1,5-a]pyridine-4-carbonitrile trifluoroacetate salt (111)

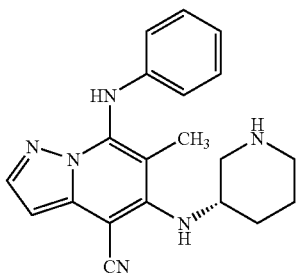

ESI/MS: 347.1 (M$^+$+H, C$_{20}$H$_{22}$N$_6$). HPLC retention time: 8.48 min

Example 108

7-[(4-Ethoxyphenyl)amino]-6-methyl-5-[(pyrrolidin-3-ylmethyl)amino]pyarzolo[1,5-a]pyridine-4-carbonitrile trifluoroacetate salt (112)

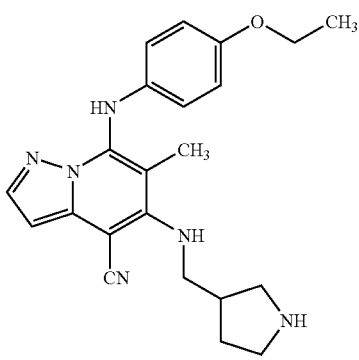

ESI/MS: 391.1 (M$^+$+H, C$_{22}$H$_{26}$N$_6$O). HPLC retention time: 9.54 min

Example 109

7-[(4-Ethoxyphenyl)amino]-6-methyl-5-[(2-(2-piperidyl)ethyl)amino]pyrazolo[1,5-a]pyridine-4-carbonitrile trifluoroacetate salt (113)

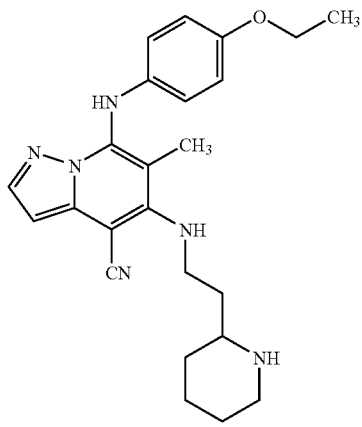

ESI/MS: 419.2 (M⁺+H, $C_{24}H_{30}N_6O$). HPLC retention time: 10.16 min

Example 110

7-[(4-Ethoxyphenyl)amino]-6-methyl-5-[(pyrrolidin-2-ylmethyl)amino]pyrazolo[1,5-a]pyridine-4-carbonitrile trifluoroacetate salt (114)

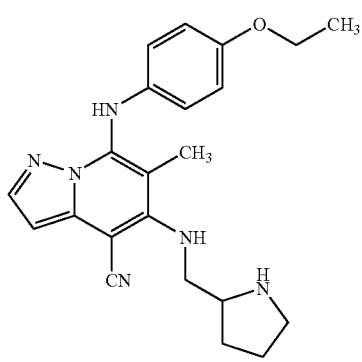

ESI/MS: 391.1 (M⁺+H, $C_{22}H_{26}N_6O$). HPLC retention time: 9.49 min

Example 111

7-[(4-Ethoxyphenyl)amino]-6-methyl-5-[trans-{4-(benzylamino)cyclohexyl]amino}pyrazolo[1,5-a]pyridine-4-carbonitrile trifluoroacetate salt (115)

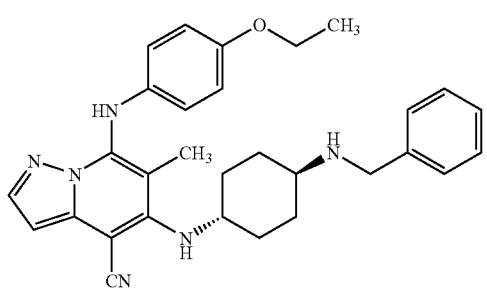

ESI/MS: 495.2 (M⁺+H, $C_{30}H_{34}N_6O$). HPLC retention time: 10.44 min

Example 112

7-[(4-Ethoxyphenyl)amino]-6-methyl-5-({trans-4-[(3-phenylpropyl)amino]cyclohexyl}amino)pyrazolo[1,5-a]pyridine-4-carbonitrile trifluoroacetate salt (116)

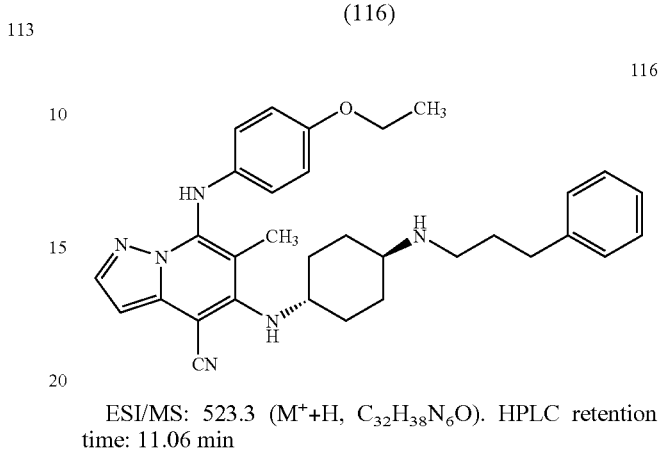

ESI/MS: 523.3 (M⁺+H, $C_{32}H_{38}N_6O$). HPLC retention time: 11.06 min

Example 113

5-[((3S)-3-Piperidyl)amino]-7-(benzothiazol-6-ylamino)-6-methylpyrazolo[1,5-a]pyridine-4-carbonitrile trifluoroacetate salt (117)

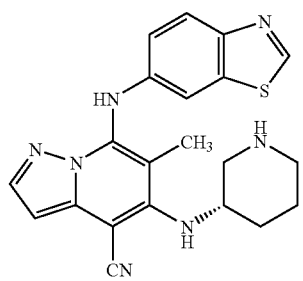

ESI/MS: 404.1 (M⁺+H, $C_{21}H_{21}N_7S$). HPLC retention time: 7.02 min

Example 114

5-[((3S)-3-Piperidyl)amino]-7-[(2-ethylbenzothiazol-6-yl)amino]-6-methylpyrazolo[1,5-a]pyridine-4-carbonitrile trifluoroacetate salt (118)

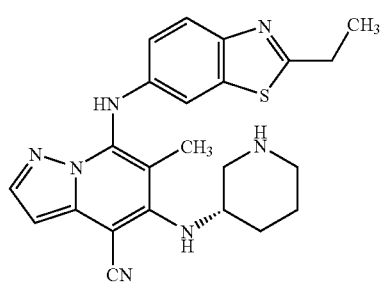

ESI/MS: 432.1 (M⁺+H, $C_{23}H_{25}N_7S$). HPLC retention time: 8.87 min

Example 115

7-[(4-Ethoxyphenyl)amino]-6-methyl-5-[(2-piperidylmethyl)amino]pylrazolo[1,5-a]pyridine-4-carbonitrile trifluoroacetate salt (119)

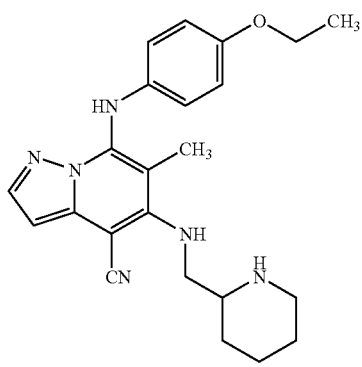

ESI/MS: 405.1 (M⁺+H, $C_{23}H_{28}N_6O$). HPLC retention time: 9.90 min

Example 116

5-{[3-(Cyclohexylamino)propyl]amino}-7-[(4-ethoxyphenyl)amino]-6-methylpyrazolo[1,5-a]pyridine-4-carbonitrile trifluoroacetate salt (120)

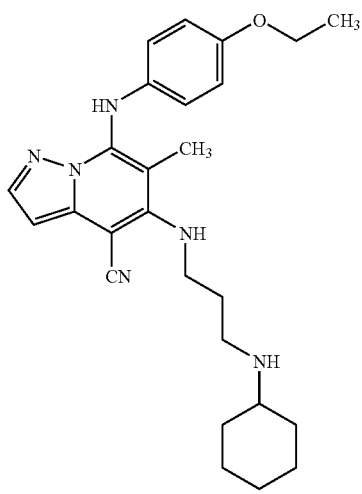

ESI/MS: 447.2 (M⁺+H, $C_{26}H_{34}N_6O$). HPLC retention time: 11.25 min

Example 117

5-[(3S)-3-Piperidylamino]-7-(4-ethoxyphenylamino)-6-propylpyrazolo[1,5-a]pyridine-4-carbonitrile (121)

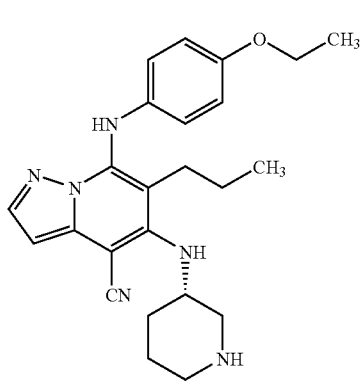

¹H-NMR (400 MHz, CDCl₃) δ (ppm): 7.77 (d, J=2.2 Hz, 1H), 7.51 (s, 1H), 7.02 (d, J=8.8 Hz, 2H), 6.84 (d, J=8.8 Hz, 2H), 6.36 (d, J=2.2 Hz, 1H), 5.58 (brs, 1H), 4.50-4.47 (m, 1H), 4.01 (q, J=7.0 Hz, 2H), 3.08-3.04 (m, 1H), 2.91-2.84 (m, 2H), 2.78-2.72 (m, 1H), 2.28 (dd, J=9.0, 6.8 Hz, 2H), 2.01-1.94 (m, 1H), 1.89-1.79 (m, 1H), 1.70-1.60 (m, 1H), 1.57-1.52 (m, 1H), 1.42 (t, J=7.0 Hz, 3H), 1.40-1.30 (m, 2H), 0.69 (t, J=7.3 Hz, 3H). ESI/MS: 419.3 (M⁺+H, $C_{24}H_{30}N_6O$). HPLC retention time: 10.65 min

Example 118

5-(trans-4-Aminocyclohexylamino)-7-(4-ethoxyphenylamino)-6-propylpyrazolo[1,5-a]pyridine-4-carbonitrile (122)

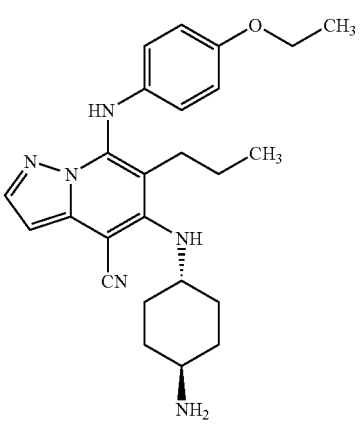

¹H-NMR (400 MHz, CDCl₃) δ (ppm): 7.78 (d, J=1.7 Hz, 1H), 7.55 (s, 1H), 7.01 (d, J=8.8 Hz, 2H), 6.84 (d, J=8.8 Hz, 2H), 6.38 (d, J=1.7 Hz, 1H), 4.30-4.01 (m, 2H), 4.02 (q, J=7.0 Hz, 2H), 2.72 (brs, 1H), 2.30-2.17(m, 4H), 2.01-1.95(m, 2H), 1.64 (brs, 3H), 1.41 (t, J=7.0 Hz, 3H), 1.40-1.30 (m, 4H), 0.68 (t, J=7.3 Hz, 3H). ESI/MS: 433.3 (M⁺+H, $C_{25}H_{32}N_6O$). HPLC retention time: 10.95 min

Example 119

5-[(3S)-3-Piperidylamino]-7-(4-ethoxyphenylamino)-6-(methylethyl)pyrazolo[1,5-a]pyridine-4-carbonitrile (123)

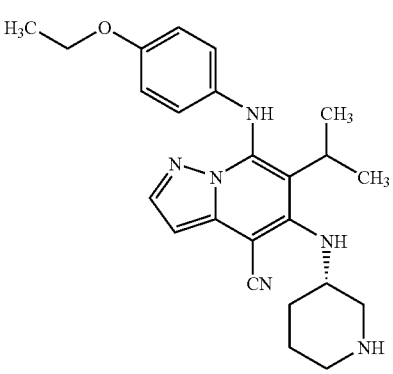

¹H-NMR (400 MHz, CDCl₃) δ (ppm): 7.75 (d, J=2.2 Hz, 1H), 7.30 (s, 1H), 7.01 (d, J=8.8 Hz, 2H), 6.84 (d, J=8.8 Hz, 2H), 6.33 (d, J=2.2 Hz, 1H), 5.58 (brs, 1H), 4.60-4.50 (m, 1H), 4.01 (q, J=7.0 Hz, 2H), 3.40-3.30 (m, 1H), 3.08-3.02 (m, 1H), 2.98-2.88 (m, 2H), 2.79-2.71 (m, 1H), 2.07-2.03 (m, 1H), 1.85-1.65 (m, 1H), 1.60-1.52 (m, 1H), 1.42 (t, J=7.0 Hz, 3H), 1.25 (d, J=7.3 Hz, 3H), 1.18 (d, J=7.3 Hz, 3H). ESI/MS: 419.3 (M⁺+H, $C_{24}H_{30}N_6O$). HPLC retention time: 10.37 min

Example 120

5-(trans-4-Aminocyclohexylamino)-7-(4-ethoxyphenylamino)-6-(methylethyl)pyrazolo[1,5-a]pyridine-4-carbonitrile (124)

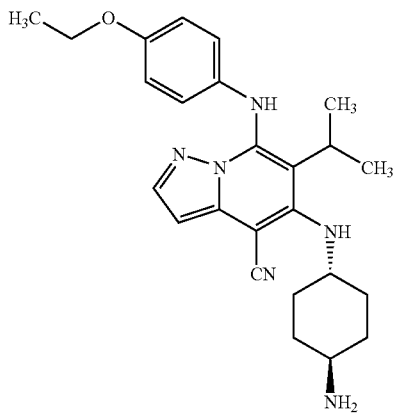

ESI/MS: 433.3 (M⁺+H, $C_{25}H_{32}N_6O$). HPLC retention time: 10.72 min

Example 121

7-[(4-Ethoxyphenyl)amino]-6-methyl-5-(trans-{4-[(2-phenylethyl)amino]cyclohexyl}amino]pyrazolo[1,5-a]pyridine-4-carbonitrile trifluoroacetate salt (125)

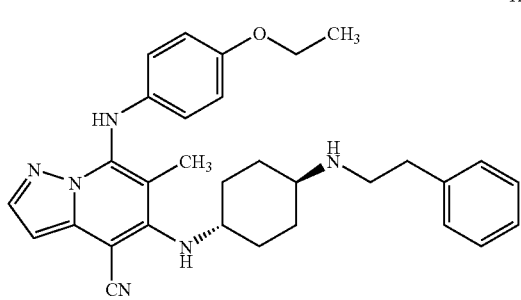

ESI/MS: 509.2 (M⁺+H, $C_{31}H_{36}N_6O$). HPLC retention time: 12.43 min

Example 122

5-({4-[(Cyclohexylmethyl)amino]cyclohexyl}amino)-7-[(4-ethoxyphenyl)amino]-6-methylpyrazolo[1,5-a]pyridine-4-carbonitrile trifluoroacetate salt (126)

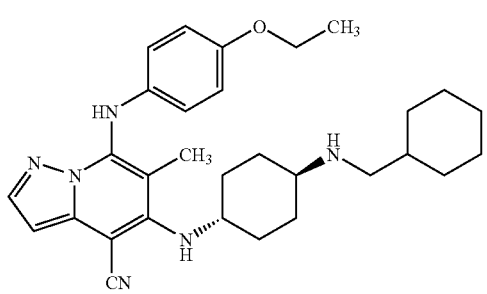

ESI/MS: 501.2 (M⁺+H, $C_{30}H_{40}N_6O$). HPLC retention time: 12.65 min

Example 123

7-[(4-Ethoxyphenyl)amino]-6-methyl-5-[4-(1,2,3,4-tetrahydroisoquinolyl)amino]pyrazolo[1,5-a]pyridine-4-carbonitrile trifluoroacetate salt (127)

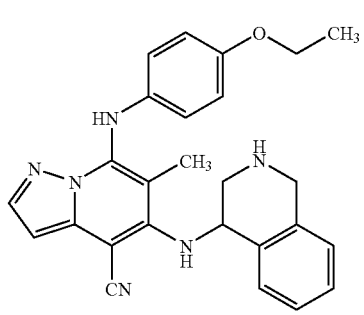

ESI/MS: 439.1 (M⁺+H, $C_{26}H_{26}N_6O$). HPLC retention time: 10.81 min

Example 124

7-[(4-Ethoxyphenyl)amino]-6-methyl-5-[(3-piperidylmethyl)amino]pyrazolo[1,5-a]pyridine-4-carbonitrile trifluoroacetate salt (128)

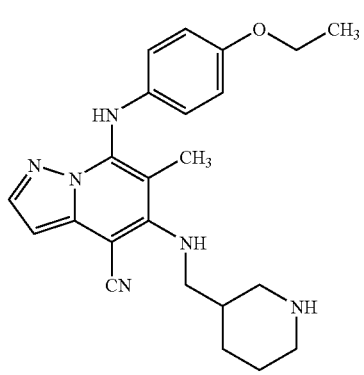

ESI/MS: 405.6 (M⁺+H, $C_{23}H_{28}N_6O$). HPLC retention time: 10.30 min

Example 125

7-[1(4-Ethoxyphenyl)amino]-6-methyl-5-[2-(pyrrolidin-2-ylethyl)amino]pyrazolo[1,5-a]pyridine-4-carbonitrile trifluoroacetate salt (129)

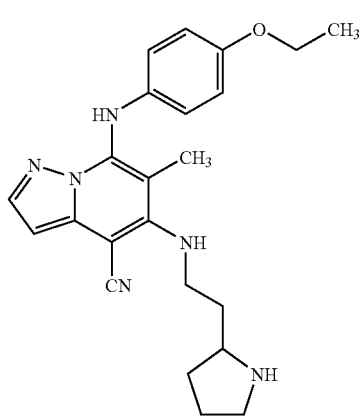

ESI/MS: 405.6 (M⁺+H, $C_{23}H_{28}N_6O$). HPLC retention time: 7.73 min

Example 126

5-[(3S)-3-Piperidylamino]-7-(4-ethoxyphenylamino)-6-cyclopropylpyrazolo[1,5-a]pyridine-4-carbonitrile (130)

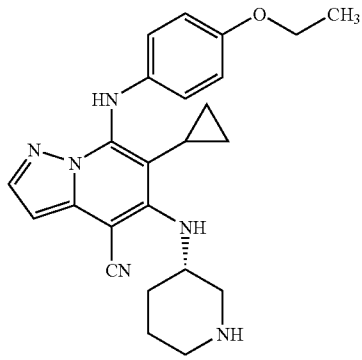

ESI/MS: 417.2 (M$^+$+H, C$_{24}$H$_{28}$N$_6$O). HPLC retention time: 10.27 min

Example 127

5-(trans-4-Amionocyclohexylamino)-7-(4-ethoxyphenylamino)-6-cyclopropylpyrazolo[1,5-a]pyridine-4-carbonitrile (131)

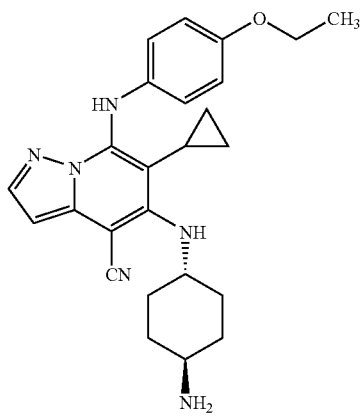

ESI/MS: 431.3 (M$^+$+H, C$_{25}$H$_{30}$N$_6$O). HPLC retention time: 10.78 min

Example 128

5-[(6-Amionohexyl)amino]-7-[(4-ethoxyphenyl)amino]-6-methylpyrazolo[1,5-a]pyridine-4-carbonitrile trifluoroacetate salt (132)

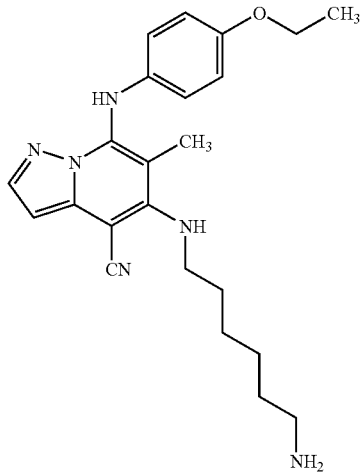

ESI/MS: 407.2 (M$^+$+H, C$_{23}$H$_{30}$N$_6$O). HPLC retention time: 10.49 min

Example 129

7-[(4-Ethoxyphenyl)amino]-6-methyl-5-{[2-(1-methylpyrrolidin-2-yl)ethyl]amino}pyrazolo[1,5-a]pyridine-4-carbonitrile trifluoroacetate salt (133)

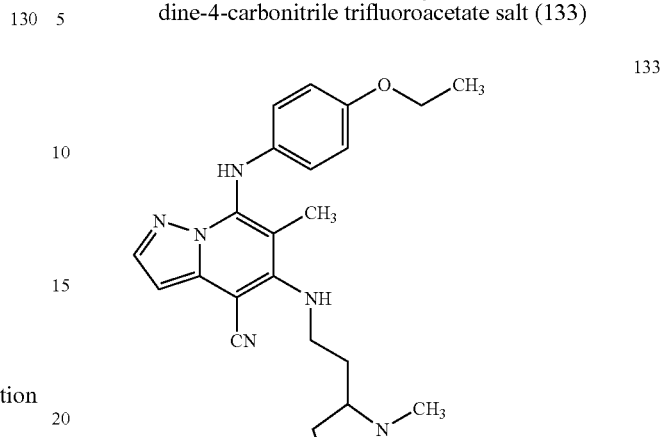

ESI/MS: 419.2 (M$^+$+H, C$_{24}$H$_{30}$N$_6$O). HPLC retention time: 11.67 min

Example 130

The structures of the compounds synthesized in the above examples were confirmed by mass analysis with a Time Of Flight-Mass Spectrometer (TOF-MS) equipped with an electrospray ionization source.

The results of mass analyses are given in Table B as the value of "M$^+$+H" (obs. Mass: the measured value observed as the molecular mass of compound (M) with one proton (H$^+$) added) recorded on an instrument under conditions shown below and the calculated value of "M$^+$+H" (pred. Mass) together with the formula (Formula) calculated from the observed value of "M$^+$+H".

Mass spectrometer: SHIMADZU LCMS-IT-TOF
LC: Prominence
Column: ZORBZX XDB-C18 (cartridge) 1.8 μm, 2.1 mm×30 mm
UV: PDA detection (254 nm)
Flow rate: 0.5 mL/min
Column temperature: 40° C.
Detection voltage: 1.60 kV Gradient Condition
Solvent: A: H$_2$O/acetonitrile=95/5, 0.05% TFA
B: H$_2$O/acetonitrile=5/95, 0.05% TFA
Flow rate: 0.5 mL/min Gradient:
0 to 0.2 min, Solvent B: 5%, Solvent A: 95%
0.2 to 2.5 min, Solvent B: from 5% to 100%, Solvent A: from 95% to 0%
2.5 to 3.8 min, Solvent B: 100%, Solvent A: 0%
3.8 to 4.0 min, Solvent B: from 100% to 5%, Solvent A: from 0% to 95%
4.0 to 4.5 min, Solvent B: 5%, Solvent A: 95%

TABLE B

| Compound No. of Examples | obs. Mass (M$^+$ + H) | pred. Mass (M$^+$ + H) | Formula (M) |
|---|---|---|---|
| 13 | 208.0278 | 208.0278 | C$_9$H$_6$ClN$_3$O |
| 21 | 309.1351 | 309.1352 | C$_{17}$H$_{16}$N$_4$O$_2$ |
| 26 | 409.1892 | 409.1876 | C$_{22}$H$_{24}$N$_4$O$_4$ |
| 27 | 435.2012 | 435.2032 | C$_{24}$H$_{26}$N$_4$O$_4$ |

TABLE B-continued

| Compound No. of Examples | obs. Mass (M+ + H) | pred. Mass (M+ + H) | Formula (M) |
|---|---|---|---|
| 45 | 591.3299 | 591.3295 | $C_{32}H_{42}N_6O_5$ |
| 85 | 391.2288 | 391.2246 | $C_{22}H_{26}N_6O$ |
| 86 | 417.2428 | 417.2403 | $C_{24}H_{28}N_6O$ |
| 87 | 421.2357 | 421.2352 | $C_{23}H_{28}N_6O_2$ |
| 88 | 407.2214 | 407.2195 | $C_{22}H_{26}N_6O_2$ |
| 89 | 435.2531 | 435.2508 | $C_{24}H_{30}N_6O_2$ |
| 90 | 421.2367 | 421.2352 | $C_{23}H_{28}N_6O_2$ |
| 91 | 418.1827 | 418.1814 | $C_{22}H_{23}N_7S$ |
| 92 | 377.2078 | 377.2090 | $C_{21}H_{24}N_6O$ |
| 93 | 367.1457 | 367.1438 | $C_{19}H_{19}ClN_6$ |
| 94 | 381.1612 | 381.1594 | $C_{20}H_{21}ClN_6$ |
| 95 | 453.2427 | 453.2403 | $C_{27}H_{28}N_6O$ |
| 96 | 418.1834 | 418.1814 | $C_{22}H_{23}N_7S$ |
| 97 | 423.2320 | 423.2297 | $C_{26}H_{26}N_6$ |
| 98 | 377.2109 | 377.2090 | $C_{21}H_{24}N_6O$ |
| 99 | 393.1862 | 393.1861 | $C_{21}H_{24}N_6S$ |
| 100 | 409.2125 | 409.2141 | $C_{25}H_{24}N_6$ |
| 101 | 405.2431 | 405.2403 | $C_{23}H_{28}N_6O$ |
| 102 | 405.2450 | 405.2403 | $C_{23}H_{28}N_6O$ |
| 103 | 391.2260 | 391.2246 | $C_{22}H_{26}N_6O$ |
| 104 | 405.2447 | 405.2403 | $C_{23}H_{28}N_6O$ |
| 105 | 405.2432 | 405.2403 | $C_{23}H_{28}N_6O$ |
| 106 | 351.1901 | 351.1933 | $C_{19}H_{22}N_6O$ |
| 107 | 365.2110 | 365.2090 | $C_{20}H_{24}N_6O$ |
| 108 | 379.2245 | 379.2246 | $C_{21}H_{26}N_6O$ |
| 109 | 419.2537 | 419.2559 | $C_{24}H_{30}N_6O$ |
| 110 | 461.3022 | 461.3029 | $C_{27}H_{36}N_6O$ |
| 111 | 347.1956 | 347.1984 | $C_{20}H_{22}N_6$ |
| 112 | 391.2223 | 391.2246 | $C_{22}H_{26}N_6O$ |
| 113 | 419.2561 | 419.2559 | $C_{24}H_{30}N_6O$ |
| 114 | 391.2245 | 391.2246 | $C_{22}H_{26}N_6O$ |
| 115 | 495.2898 | 495.2872 | $C_{30}H_{34}N_6O$ |
| 116 | 523.3180 | 523.3185 | $C_{32}H_{38}N_6O$ |
| 117 | 404.1644 | 404.1657 | $C_{21}H_{21}N_7S$ |
| 118 | 432.1972 | 432.1970 | $C_{23}H_{25}N_7S$ |
| 119 | 405.2418 | 405.2403 | $C_{23}H_{28}N_6O$ |
| 120 | 447.2912 | 447.2872 | $C_{26}H_{34}N_6O$ |
| 121 | 419.2559 | 419.2559 | $C_{24}H_{30}N_6O$ |
| 122 | 433.2709 | 433.2716 | $C_{25}H_{32}N_6O$ |
| 123 | 419.2569 | 419.2559 | $C_{24}H_{30}N_6O$ |
| 124 | 433.2737 | 433.2716 | $C_{25}H_{32}N_6O$ |
| 125 | 509.3063 | 509.3029 | $C_{31}H_{36}N_6O$ |
| 126 | 501.3338 | 501.3342 | $C_{30}H_{40}N_6O$ |
| 128 | 405.2407 | 405.2403 | $C_{23}H_{28}N_6O$ |
| 129 | 405.2408 | 405.2403 | $C_{23}H_{28}N_6O$ |
| 130 | 417.2416 | 417.2403 | $C_{24}H_{28}N_6O$ |
| 131 | 431.2572 | 431.2559 | $C_{25}H_{30}N_6O$ |
| 132 | 407.2558 | 407.2559 | $C_{23}H_{30}N_6O$ |
| 133 | 419.2568 | 419.2559 | $C_{24}H_{30}N_6O$ |

Example 131

General Measurement Method for Determining the Inhibitory Activity Against MAPKAP-K2 enzyme (Preparation of Solutions of Compounds)

Each compound was dissolved in DMSO to prepare a solution with a concentration of 20 mmol/L and this solution was stored at −20° C. This stock solution was diluted with DMSO successively to prepare solutions with 200-fold concentrations of a necessary range. These solutions were further diluted with water at a ratio of 1:20 to prepare solutions with 10-fold concentrations of a necessary range. Each of these solutions (5 μL) was used for each reaction in 50 μL-scale. Through the dilution series of all compounds, the final DMSO concentration was kept at 0.5%. Conventional tests for the compounds were carried out at a final concentration range from 100 μmol/L to 0.03 μmol/L. but in some cases, tests were carried out at lower concentrations, depending on activity.

(Measurements of MAPKAP-K2 Enzyme Activities)

To a 5% DMSO aqueous solution (5 μL) of a test compound, a solution (25 μL) containing a peptide substrate [peptide substrate 60 μmol/L, ATP 20 μmol/L, Tris buffer 60 mmol/L (pH 7.5), EGTA 0.2 mmol/L, β-mercaptoethanol 0.2%, magnesium acetate 20 mmol/L, [γ-33P]ATP 0.1 μCi (specific radioactivity ca. 110 TBq/mmol)] was added. The reaction was initiated by adding a solution (20 μL) containing MAPKAP-K2 enzyme [recombinant human MAPKAP-K2 10 mU, Tris buffer 50 mol/L (pH 7.5), EGTA 0.1 mmol/L, β-mercaptoethanol 0.1%, BSA 0.1%]. After the reaction was carried out at room temperature for 30 min, 200 mmol/L phosphoric acid (50 μL) was added to quench the reaction, and 90 μL of the reaction mixture was adsorbed on a multiscreen PH plate (Millipore). The plate was washed with 100 mmol/L phosphoric acid. After the plate was dried, 30 μL of MicroScint-O (Perkin-Elmer) was added, and the count per minute was measured on a scintillation counter to determine the inhibitory activity. The peptide substrate was Lys-Lys-Leu-Asn-Arg-Thr-Leu-Ser-Val-Ala.

(Note)
% Reference=(X−B)/(Tot−B)×100
% Inhibition=100−% Reference
X represents count per minute of the well with a test compound applied.
B represents count per minute of the well without the enzyme.
Tot represents count per minute of the well with only DMSO solvent and no test compound applied.

(Calculation of MAPKAP-K2 Inhibitory Activity)
$IC_{50}$ value represents a concentration of compound at which 50% inhibition is observed.

The efficiencies of the compounds against MAPKAP-K2 are listed in the following Table C.

(For activity strength in the table, ++++ represents $IC_{50}$ value<0.2 μmol/L; +++ represents 0.2 μmol/L $\leq IC_{50}$ value <1 μmol/L; ++ represents 1 μmol/L <$IC_{50}$ value <10 μmol/L; and +represents 10 μmol/L $\leq IC_{50}$ value <100 μmol/L.)

TABLE C

| Compound No. of Examples | Activity Strength |
|---|---|
| 85 | ++++ |
| 86 | ++++ |
| 87 | ++++ |
| 88 | +++ |
| 89 | ++++ |
| 90 | ++++ |
| 91 | ++++ |
| 92 | +++ |
| 93 | +++ |
| 94 | +++ |
| 95 | +++ |
| 96 | +++ |
| 97 | ++++ |
| 98 | +++ |
| 99 | ++ |
| 100 | +++ |
| 101 | + |
| 102 | ++++ |
| 103 | +++ |
| 104 | ++ |
| 105 | ++++ |
| 106 | +++ |
| 107 | +++ |
| 108 | +++ |
| 109 | ++++ |
| 110 | ++++ |
| 111 | ++++ |
| 112 | ++ |
| 113 | + |
| 114 | ++ |

TABLE C-continued

| Compound No. of Examples | Activity Strength |
|---|---|
| 115 | +++ |
| 116 | +++ |
| 117 | ++++ |
| 118 | ++++ |
| 119 | ++ |
| 120 | ++ |
| 121 | ++++ |
| 122 | ++++ |
| 123 | ++++ |
| 124 | ++++ |
| 125 | +++ |
| 126 | +++ |
| 127 | ++ |
| 128 | ++ |
| 129 | ++ |
| 130 | +++ |
| 131 | ++++ |
| 132 | + |
| 133 | + |

INDUSTRIAL APPLICABILITY

The compound of the present invention is valuable for a MAPKAP-K2 inhibitor or its intermidiate.

Further, by using the compound of the present invention, there is provided a novel MAPKAP-K2 inhibitor or a novel medicine for treating or preventing neurodegenerative/neurological disorders (including dementia), inflammatory diseases, sepsis, autoimmune diseases, destructive osteopathy, diabetes mellitus, cancer, ischemic reperfusion injury, angiodysplasia, cachexia, obesity, angiogenesis, asthma and/or chronic obstructive pulmonary disease (COPD).

What is claimed is:

1. A pyrazolo[1,5-a]pyridine derivative represented by formula (I) or pharmaceutically acceptable salt thereof:

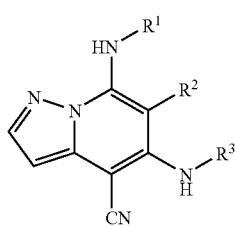

(I)

[In formula (I), $R^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of $R^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-SR^{1b}$, $-NR^{1c}R^{1d}$, $-C(=O)R^{1e}$, $-S(=O)_2NR^{1f}R^{1g}$, $-C(=O)OR^{1h}$, $-C(=O)NR^{1i}R^{1j}$, $-NR^{1k}C(=O)R^{1l}$ and $-NR^{1m}S(=O)_2R^{1n}$;

$R^{1x}$ (x represents a, b, c, d, e, f, g, h, i, j, k, l, m or n) may be identical or different, and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$, these substituents may bond to each other via an oxygen atom, a nitrogen atom, a sulfur atom or a single bond to form a ring;

$R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, $-OR^{2a}$, $-SR^{2b}$, $-NR^{2c}R^{2d}$, $-C(=O)R^{2e}$, $-S(=O)_2NR^{2f}R^{2g}$, $-C(=O)OR^{2h}$, $-C(=O)NR^{2i}R^{2j}$, $-NR^{2k}C(=O)R^{21}$ and $-NR^{2m}S(=O)_2R^{2n}$;

$R^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring;

$R^3$ represents an optionally substituted C1-C8 alkyl group, an optionally substituted C3-C8 cycloalkyl group or an optionally substituted aliphatic heterocyclic group;

the substituent(s) of $R^3$ are one or more substituent(s) selected from the group consisting of a halogen atom, a cyano group, a nitro group, $-OR^{3a}$, $-SR^{3b}$, $-NR^{3c}R^{3d}$, an optionally substituted C1-C8 alkyl group, an optionally substituted C3-C8 cycloalkyl group and an optionally substituted aliphatic heterocyclic group;

$R^{3z}$ (z represents a, b, c or d) may be identical or different and represents a hydrogen atom, an optionally substituted C1-C8 alkyl group (when two C1-C8 alkyl groups as $R^{3z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group; and the substituent(s) of substituent of $R^1$, $R^2$ and $R^3$ are, unless specifically defined, one or more substituent(s) selected from the group consisting of a halogen atom; a hydroxyl group; a cyano group; a nitro group; an amino group; an oxo group; a carboxyl group; a trifluromethyl group; a pentafluoroethyl group; a trifluoromethoxy group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group optionally substituted with methyl group(s), halogen atom(s), hydroxyl group(s) or cyano group(s); an aliphatic heterocyclic group optionally substituted with methyl group(s), halogen atom(s), hydroxyl group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s)].

2. The pyrazolo[1,5-a]pyridine derivative or pharmaceutically acceptable salt thereof according to claim 1, wherein:

$R^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of $R^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, $-OR^{1a}$, $-SR^{1b}$, $-NR^{1c}R^{1d}$, $-C(=O)R^{1e}$, $-S(=O)_2NR^{1f}R^{1g}$, $-C(=O)OR^{1h}$, $-C(=O)NR^{1i}R^{1j}$, $-NR^{1k}C(=O)R^{1l}$ and $-NR^{1m}S(=O)_2R^{1n}$;

$R^{1x}$ (x represents a, b, c, d, e, f, g, h, i, j, k, l, m or n) may be identical or different and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$, these substituents may bond to each other via an oxygen atom, a nitrogen atom, a sulfur atom or a single bond to form a ring;

$R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, $-OR^{2a}$, $-SR^{2b}$, $-NR^{2c}R^{2d}$, $-C(=O)R^{2e}$, $-S(=O)_2NR^{2f}R^{2g}$, $-C(=O)OR^{2h}$, $-C(=O)NR^{2i}R^{2j}$, $-NR^{2k}C(=O)R^{2l}$ and $-NR^{2m}S(=O)_2R^{2n}$;

$R^{2y}$ (y represents a, b, c, d, e, f, g, h, i, j, k, l, m or n) may be identical or different and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring;

$R^3$ represents an optionally substituted C1-C8 alkyl group, an optionally substituted C3-C8 cycloalkyl group or an optionally substituted aliphatic heterocyclic group;

the substituent(s) of $R^3$ are one or more substituent(s) selected from the group consisting of a halogen atom, a cyano group, a nitro group, $-OR^{3a}$, $-SR^{3b}$, $-NR^{3c}R^{3d}$, an optionally substituted C1-C8 alkyl group, an optionally substituted C3-C8 cycloalkyl group and an optionally substituted aliphatic heterocyclic group;

$R^{3z}$ (z represents a, b, c or d) may be identical or different and represents a hydrogen atom, an optionally substituted C1-C8 alkyl group (when two C1-C8 alkyl groups as $R^{3z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group; and the substituent(s) of substituent of $R^1$, $R^2$ and $R^3$ are, unless specifically defined, one or more substituent(s) selected from the group consisting of a halogen atom; a hydroxyl group; a cyano group; a nitro group; an amino group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group optionally substituted with methyl group(s), halogen atom(s), hydroxyl group(s) or cyano group(s); an aliphatic heterocyclic group optionally substituted with methyl group(s), halogen atom(s), hydroxyl group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s).

3. The pyrazolo[1,5-a]pyridine derivative or pharmaceutically acceptable salt thereof according to claim 1, except for:

compounds wherein $R^1$ is an unsubstituted or fluorinated C1-C6 alkyl group or an unsubstituted C3-C7 cycloalkyl group; $R^2$ is an unsubstituted C1-C6 alkyl group or a C1-C6 alkyl group substituted with a halogen atom, a hydroxyl group or —$NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6alkyl group or an unsubstituted C3-C7 cycloalkyl group); and $R^3$ is an unsubstituted C1-C6 alkyl group:

compounds wherein $R^1$ is an unsubstituted C1-C6 alkyl group or an unsubstituted or halogenated phenyl group; $R^2$ is an unsubstituted C1-C6 alkyl group or a C1-C6 alkyl group substituted with a halogen atom, a —OH or —$NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6 alkyl group or an unsubstituted C3-C7 cycloalkyl group); and $R^3$ is an unsubstituted or fluorinated C1-C6 alkyl group or an unsubstituted C3-C7 cycloalkyl group: and compounds wherein $R^1$ is a C1-C8 alkyl group substituted with —$NR^{1c}R^{1d}$, —$NR^{1k}$—CO—$R^{1l}$ or —$NR^{1m}S(=O)_2R^{1n}$ or a C3-C8 cycloalkyl group substituted with —$NR^{1c}R^{1d}$, —$NR^{1k}$—CO —$R^{1l}$ or —$NR^{1m}S(=O)_2R^{1n}$; and $R^3$ is an unsubstituted alkyl group or an alkyl group substituted with $OR^{3a}$.

4. The pyrazolo[1,5-a]pyridine derivative or pharmaceutically acceptable salt thereof according to claim 1, wherein:

$R^1$ is a C1-C8 alkyl group substituted with substituent(s) other than a fluorine atom, —$NR^{1c}R^{1d}$, —$NR^{1k}$—CO—$R^{1l}$ or —$NR^{1m}S(=O)_2R^{1n}$, an optionally substituted C2-C8 alkenyl group, an optionally substituted C2-C8 alkynyl group, a C6 aryl group substituted with substituent(s) other than halogen atoms, an optionally substituted C7-C14 aryl group, an optionally substituted heteroaryl group, an optionally substituted C7-C16 aralkyl group, an optionally substituted heteroarylalkyl group, a C3-C8 cycloalkyl group substituted with substituent(s) other than, —$NR^{1c}R^{1d}$, —$NR^{1k}$—CO—$R^{1l}$ or —$NR^{1m}S(=O)_2R^{1n}$, or an optionally substituted aliphatic heterocyclic group; and $R^3$ is a C1-C8 alkyl group substituted with substituent(s) other than a fluorine atom or —$OR^{3a}$, a substituted C3-C8 cycloalkyl group or an optionally substituted aliphatic heterocyclic group.

5. The pyrazolo[1,5-a]pyridine derivative or pharmaceutically acceptable salt thereof according to claim 1, wherein $R^1$ is an optionally substituted C1-C8 alkyl group, an optionally substituted C6-C14 aryl group, an optionally substituted heteroaryl group, an optionally substituted C7-C16 aralkyl group, an optionally substituted heteroarylalkyl group or an optionally substituted C3-C8 cycloalkyl group.

6. The pyrazolo[1,5-a]pyridine derivative or pharmaceutically acceptable salt thereof according to claim 1, wherein $R^1$ is an optionally substituted C1-C8 alkyl group, an optionally substituted C6-C14 aryl group or an optionally substituted heteroaryl group.

7. The pyrazolo[1,5-a]pyridine derivative or pharmaceutically acceptable salt thereof according to claim 1, wherein $R^1$ is an optionally substituted C6-C14 aryl group or an optionally substituted heteroaryl group.

8. The pyrazolo[1,5-a]pyridine derivative or pharmaceutically acceptable salt thereof according to claim 1, wherein $R^1$ is an optionally substituted phenyl group.

9. The pyrazolo[1,5-a]pyridine derivative or pharmaceutically acceptable salt thereof according to claim 1, wherein $R^1$ is an optionally substituted heteroaryl group.

10. The pyrazolo[1,5-a]pyridine derivative or pharmaceutically acceptable salt thereof according to claim 9, wherein $R^1$ is a heteroaryl group wherein a phenyl group and an optionally substituted monocyclic heteroaryl ring are fused and the phenyl group bonds to the NH group at the 7 position of the pyrazolo[1,5-a]pyridine derivative of formula (I).

11. The pyrazolo[1,5-a]pyridine derivative or pharmaceutically acceptable salt thereof according to claim 1, wherein $R^1$ is an optionally substituted C7-C16 aralkyl group or an optionally substituted heteroarylalkyl group.

12. The pyrazolo[1,5-a]pyridine derivative or pharmaceutically acceptable salt thereof according to claim 1, wherein the substituent(s) of $R^1$ are one or more substituent(s) selected from the group consisting of a fluorine atom, a chlorine atom, a cyano group, a nitro group, an optionally substituted C1-C6 alkyl group, an optionally substituted C3-C8 cycloalkyl group, an optionally substituted C1-C6 alkoxy group, an optionally substituted C1-C6 alkylthio group, an optionally substituted phenyl group, an optionally substituted heteroaryl group, an optionally substituted C1-C6 acyl group, an optionally substituted C1-C6 acylamino group, an optionally substituted aminosulfonyl group (when two alkyl groups bond to the aminosulfonyl group, they may be identical or different and they may bond to each other via an oxygen atom, a nitrogen atom, a sulfur atom or a single bond to form a ring), an optionally substituted C2-C7 alkoxycarbonyl group, an optionally substituted sulfonylamino group and an optionally substituted carbamoyl group (when two alkyl groups bond to the carbamoyl group, they may be identical or different and they may bond to each other via an oxygen atom, a nitrogen atom, a sulfur atom or a single bond to form a ring).

13. The pyrazolo[1,5-a]pyridine derivative or pharmaceutically acceptable salt thereof according to claim 1, wherein the substituent(s) of $R^1$ are one or more substituent(s) selected from the group consisting of a fluorine atom, a chlorine atom, a cyano group, a nitro group, an optionally substituted C1-C6 alkylthio group, an optionally substituted C1-C6 acyl group, an optionally substituted C1-C6 acylamino group, an optionally substituted aminosulfonyl group (when two alkyl groups bond to the aminosulfonyl group, they may be identical or different and they may bond to each other via an oxygen atom, a nitrogen atom, a sulfur atom or a single bond to form a ring), an optionally substituted C2-C7 alkoxycarbonyl group, an optionally substituted sulfonylamino group and an optionally substituted carbamoyl group (when two alkyl groups bond to the carbamoyl group, they may be identical or different and they may bond to each other via an oxygen atom, a nitrogen atom, a sulfur atom or a single bond to form a ring).

14. The pyrazolo[1,5-a]pyridine derivative or pharmaceutically acceptable salt thereof according to claim 1, wherein the substituent(s) of $R^1$ are one or more substituent(s) selected from the group consisting of a fluorine atom, a chlorine atom, a cyano group, a nitro group, an optionally substituted phenyl group and an optionally substituted heteroaryl group.

15. The pyrazolo[1,5-a]pyridine derivative or pharmaceutically acceptable salt thereof according to claim 1, wherein the substituent(s) of $R^1$ are a substituent selected from the group consisting of an optionally substituted phenyl group and an optionally substituted heteroaryl group; and the substituent(s) of $R^1$ may contain one or more substituent(s) selected from the group consisting of a fluorine atom, a chlorine atom, a cyano group and a nitro group.

16. The pyrazolo[1,5-a]pyridine derivative or pharmaceutically acceptable salt thereof according to claim 1, wherein the substituent(s) of $R^1$ are one or more substituent(s) selected from the group consisting of a fluorine atom; a chlorine atom; a cyano group; a C1-C6 alkyl group(s) optionally substituted with one or more substituent(s) selected from the group consisting of a halogen atom, a hydroxyl group and a cyano group; a C3-C8 cycloalkyl group(s) optionally substituted with one or more substituent(s) selected from the group consisting of a halogen atom, a hydroxyl group and a cyano group; a C1-C6 alkyl group(s) substituted with a C1-C6 alkoxy group optionally substituted with one or more substituent(s) selected from the group consisting of a halogen atom, a hydroxyl group and a cyano group; and a C1-C6 alkyl group(s) substituted with a C3-C6 cycloalkyl-oxy group optionally substituted with one or more substituent(s) selected from the group consisting of a methyl group, a halogen atom, a hydroxyl group, a cyano group and an oxo group.

17. The pyrazolo[1,5-a]pyridine derivative or pharmaceutically acceptable salt thereof according to claim 1, wherein:
the substituent(s) of $R^1$ are one or more substituent(s) selected from the group consisting of:
a C1-C6 alkyl group(s) optionally substituted with one or more substituent(s) selected from the group consisting of a halogen atom, a hydroxyl group and a cyano group;
a C3-C8 cycloalkyl group(s) optionally substituted with one or more substituent(s) selected from the group consisting of a halogen atom, a hydroxyl group and a cyano group;
a C1-C6 alkyl group(s) substituted with a C1-C6 alkoxy group optionally substituted with one or more substituent(s) selected from the group consisting of a halogen atom, a hydroxyl group and a cyano group; a C1-C6 alkyl group substituted with a C3-C6 cycloalkyl-oxy group optionally substituted with one or more substituent(s) selected from the group consisting of a methyl group, a halogen atom, a hydroxyl group, a cyano group and an oxo group; and
the substituent(s) of $R^1$ may contain one or more substituent(s) selected from the group consisting of a fluorine atom, a chlorine atom and a cyano group.

18. The pyrazolo[1,5-a]pyridine derivative or pharmaceutically acceptable salt thereof according to claim 1, wherein:
the substituent(s) of $R^1$ are one or more substituent(s) selected from the group consisting of:
a C1-C6 alkyl group(s) optionally substituted with one or more substituent(s) selected from the group consisting of a carboxyl group, an oxo group and a C1-C6 alkoxy group optionally substituted with one or more substituent(s) selected from the group consisting of a halogen atom, a hydroxyl group and a cyano group;
a C1-C6 alkyl group(s) optionally substituted with a heteroaryl group optionally substituted with one or more substituent(s) selected from the group consisting of a methyl group, a halogen atom, a hydroxyl group and a cyano group; and a C1-C6 alkyl group(s) optionally substituted with an aliphatic heterocyclic group optionally substituted with one or more substituent(s) selected from the group consisting of a methyl group, a halogen atom, a hydroxyl group and a cyano group; and
the substituent(s) of $R^1$ may contain one or more substituent(s) selected from the group consisting of a fluorine atom, a chlorine atom, a cyano group and a methyl group.

19. The pyrazolo[1,5-a]pyridine derivative or pharmaceutically acceptable salt thereof according to claim 1, wherein the substituent(s) of $R^1$ are C1-C6 alkyl group(s) optionally substituted with one or more substituent(s) selected from the group consisting of a halogen atom, a hydroxyl group and a cyano group.

20. The pyrazolo[1,5-a]pyridine derivative or pharmaceutically acceptable salt thereof according to claim 1, wherein the substituent(s) of $R^1$ are one or more substituent(s) selected from the group consisting of:
a fluorine atom;
a chlorine atom;
a cyano group;
a C1-C6 alkoxy group(s) optionally substituted with one or more substituent(s) selected from the group consisting of a halogen atom, a hydroxyl group and a cyano group;
a C1-C6 alkoxy group(s) substituted with an aliphatic heterocyclic group optionally substituted with one or more substituent(s) selected from the group consisting of a methyl group, a halogen atom, a hydroxyl group and a cyano group;
a C1-C6 alkoxy group(s) substituted with a C1-C6 alkoxy group(s) optionally substituted with one or more substituent(s) selected from the group consisting of a halogen atom, a hydroxyl group, and a cyano group; and a C1-C6 alkoxy group(s) substituted with a C3-C6 cycloalkyl-oxy group optionally substituted with one or more substituent(s) selected from the group consisting of a methyl group, a halogen atom, a hydroxyl group, a cyano group and an oxo group.

21. The pyrazolo[1,5-a]pyridine derivative or pharmaceutically acceptable salt thereof according to claim 1, wherein the substituent(s) of $R^1$ are one or more substituent(s) selected from the group consisting of:
a C1-C6 alkoxy group(s) optionally substituted with one or more substituent(s) selected from the group consisting of a halogen atom, a hydroxyl group and a cyano group;
a C1-C6 alkoxy group(s) substituted with an aliphatic heterocyclic group optionally substituted with one or more substituent(s) selected from the group consisting of a methyl group, a halogen atom, a hydroxyl group and a cyano group;
a C1-C6 alkoxy group(s) substituted with a C1-C6 alkoxy group optionally substituted with one or more substituent(s) selected from the group consisting of a halogen atom, a hydroxyl group and a cyano group; and a C1-C6 alkoxy group(s) substituted with a C3-C6 cycloalkyl-oxy group optionally substituted with one or more substituent(s) selected from the group consisting of a methyl group, a halogen atom, a hydroxyl group, a cyano group and an oxo group; and
the substituent(s) of $R^1$ may contain one or more substituent(s) selected from the group consisting of a fluorine atom, a chlorine atom and a cyano group.

22. The pyrazolo[1,5-a]pyridine derivative or pharmaceutically acceptable salt thereof according to claim 1, wherein the substituent(s) of $R^1$ are one or more substituent(s) selected from the group consisting of:
a C1-C6 alkoxy group(s) optionally substituted with one or more substituent(s) selected from the group consisting of a carboxyl group, an oxo group and a C1-C6 alkoxy group(s) optionally substituted with one or more substituent(s) selected from the group consisting of a halogen atom, a hydroxyl group and a cyano group; and a C1-C6 alkoxy group(s) optionally substituted with a heteroaryl group optionally substituted with one or more substituent(s) selected from the group consisting of a methyl group, a halogen atom, a hydroxyl group and a cyano group; and the substituent(s) of $R^1$ may contain one or more substituent (s) selected from the group consisting of a fluorine atom, a chlorine atom, a cyano group and a methyl group.

23. The pyrazolo[1,5-a]pyridine derivative or pharmaceutically acceptable salt thereof according to claim 1, wherein the substituent(s) of $R^1$ are C1-C6 alkoxy group(s) optionally substituted with one or more substituent(s) selected from the group consisting of a halogen atom, a hydroxyl group and a cyano group.

24. The pyrazolo[1,5-a]pyridine derivative or pharmaceutically acceptable salt thereof according to claim 1, wherein $R^2$ is a hydrogen atom, an optionally substituted C1-C8 alkyl group, an optionally substituted C2-C8 alkenyl group, an optionally substituted C6-C14 aryl group, an optionally substituted heteroaryl group, an optionally substituted C7-C16 aralkyl group, an optionally substituted heteroarylalkyl group, or an optionally substituted C3-C8 cycloalkyl group.

25. The pyrazolo[1,5-a]pyridine derivative or pharmaceutically acceptable salt thereof according to claim 1, wherein $R^2$ is a hydrogen atom, an optionally substituted C1-C6 alkyl group, an optionally substituted C2-C6 alkenyl group, an optionally substituted C6-C14 aryl group, an optionally substituted heteroaryl group, an optionally substituted C7-C12 phenylalkyl group or an optionally substituted C3-C6 cycloalkyl group.

26. The pyrazolo[1,5-a]pyridine derivative or pharmaceutically acceptable salt thereof according to claim 1, wherein $R^2$ is a hydrogen atom, an optionally substituted C1-C6 alkyl group, an optionally substituted C2-C6 alkenyl group, or an optionally substituted C3-C6 cycloalkyl group.

27. The pyrazolo[1,5-a]pyridine derivative or pharmaceutically acceptable salt thereof according to claim 1, wherein $R^2$ is an optionally substituted C1-C6 alkyl group or an optionally substituted C2-C6 alkenyl group.

28. The pyrazolo[1,5-a]pyridine derivative or pharmaceutically acceptable salt thereof according to claim 1, wherein $R^2$ is an optionally substituted C1-C4 alkyl group.

29. The pyrazolo[1,5-a]pyridine derivative or pharmaceutically acceptable salt thereof according to claim 1, wherein $R^2$ is a hydrogen atom.

30. The pyrazolo[1,5-a]pyridine derivative or pharmaceutically acceptable salt thereof according to claim 1, wherein $R^2$ is an optionally substituted phenyl group or an optionally substituted heteroaryl group.

31. The pyrazolo[1,5-a]pyridine derivative or pharmaceutically acceptable salt thereof according to claim 1, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 alkyl group, an optionally substituted C1-C6 alkoxy group, an optionally substituted C1-C6 acyl group, an optionally substituted aminosulfonyl group (when two alkyl groups bond to the aminosulfonyl group, they may be identical or different and may bond to each other via an oxygen atom, a nitrogen atom, a sulfur atom or a single bond to form a ring), an optionally substituted sulfonylamino group and an optionally substituted carbamoyl group (when two alkyl groups bond to the carbamoyl group, they may be identical or different and may bond to each other via an oxygen atom, a nitrogen atom, a sulfur atom or a single bond to form a ring).

32. The pyrazolo[1,5-a]pyridine derivative or pharmaceutically acceptable salt thereof according to claim 1, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 acyl group and an optionally substituted carbamoyl group (when two alkyl groups bond to the carbamoyl group, they may be identical or different and may bond to each other via an oxygen atom, a nitrogen atom, a sulfur atom or a single bond to form a ring).

33. The pyrazolo[1,5-a]pyridine derivative or pharmaceutically acceptable salt thereof according to claims 1, wherein the substituent(s) of $R^2$ are one or more substituent(s) selected from the group consisting of a halogen atom, a cyano group, a nitro group, a hydroxyl group, an optionally substituted amino group (when two alkyl groups bond to the amino group, they may be identical or different and may bond to each other via an oxygen atom, a nitrogen atom, a sulfur atom or a single bond to form a ring), an optionally substituted C1-C6 alkyl group and an optionally substituted C1-C6 alkoxy group.

34. The pyrazolo[1,5-a]pyridine derivative or pharmaceutically acceptable salt thereof according to claim 1, wherein $R^3$ is an optionally substituted C1-C8 alkyl group, an optionally substituted C3-C8 cycloalkyl group or an optionally substituted aliphatic heterocyclic group.

35. The pyrazolo[1,5-a]pyridine derivative or pharmaceutically acceptable salt thereof according to claim 1, wherein $R^3$ is an optionally substituted C3-C8 cycloalkyl group or an optionally substituted aliphatic heterocyclic group having 1 to 4 nitrogen atom(s) as heteroatoms.

36. The pyrazolo[1,5-a]pyridine derivative or pharmaceutically acceptable salt thereof according to claim 1, wherein $R^3$ is an optionally substituted C5-C6 cycloalkyl group, an optionally substituted piperidyl group, an optionally substituted pyrrolidinyl group or an optionally substituted hexahydroazepinyl group.

37. The pyrazolo[1,5-a]pyridine derivative or pharmaceutically acceptable salt thereof according to claim 1, wherein $R^3$ is an optionally substituted cyclohexyl group, an optionally substituted piperidyl group or an optionally substituted pyrrolidinyl group.

38. The pyrazolo[1,5-a]pyridine derivative or pharmaceutically acceptable salt thereof according to claim 1, wherein $R^3$ is an optionally substituted piperidyl group.

39. The pyrazolo[1,5-a]pyridine derivative or pharmaceutically acceptable salt thereof according to claim 1, wherein $R^3$ is an optionally substituted C1-C4 alkyl group.

40. The pyrazolo[1,5-a]pyridine derivative or pharmaceutically acceptable salt thereof according to claim 1, wherein the substituent(s) of $R^3$ are one or more substituent(s) selected from the group consisting of a fluorine atom, a hydroxyl group, a cyano group, an optionally substituted C1-C6 alkyl group and an optionally substituted amino group (when two alkyl groups bond to the amino group, they may be identical or different and may bond to each other via an oxygen atom, a nitrogen atom, a sulfur atom or a single bond to form a ring).

41. The pyrazolo[1,5-a]pyridine derivative or pharmaceutically acceptable salt thereof according to claim 1, wherein the substituent(s) of $R^3$ are one or more substituent(s) selected from the group consisting of a fluorine atom; a hydroxyl group; a cyano group; an optionally substituted amino group (when two alkyl groups bond to the amino group, they may be identical or different and may bond to each other via an oxygen atom, a nitrogen atom, a sulfur atom or a single bond to form a ring); a C5-C6 cycloalkyl group optionally substituted with an optionally substituted amino group (when two alkyl groups bond to the amino group, they may be identical or different and may bond to each other via an oxygen atom, a nitrogen atom, a sulfur atom or a single bond to form a ring); a piperazino group optionally substituted with C1-C6 alkyl group(s) optionally substituted with fluorine atom(s) or hydroxyl group(s), a piperidyl group optionally substituted with C1-C6 alkyl group(s) optionally substituted with fluorine atom(s) or hydroxyl group(s) or a pyrrolidinyl group optionally substituted with C1-C6 alkyl group(s) optionally substituted with fluorine atom(s) or hydroxyl group(s).

42. A pyrazolo[1,5-a]pyridine derivative represented by formula (7) or salt thereof:

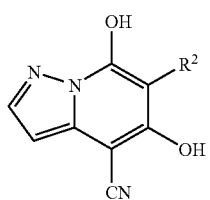

(6)

wherein $R^2$ represents a hydrogen atom, an optionally substituted C1-C8 alkyl group, an optionally substituted C2-C8 alkenyl group, an optionally substituted C2-C8 alkynyl group, an optionally substituted (6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

to substituent(s) of $R^2$ are one or more substituent(s) selected from the group consisting of a halogen atom, a cyano group, a nitro group, an optionally substituted C1-C8 alkyl group, $—OR^{2a}$, $—SR^{2b}$, $—NR^{2c}R^{2d}$, $—C(=O)R^{2e}$, $—S(=O)_2NR^{2f}R^{2g}$, $—C(=O)OR^{2h}$, $—C(=O)NR^{2i}R^{2j}$, $—NR^{2k}C(=O)R^{2l}$ and $—NR^{2m}S(=O)_2^n$;

$R^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or at optionally substituted heteroarylalkyl group;

when $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring.

43. A pyrazolo[1,5-a]pyridine derivative represented by formula (7) or salt thereof:

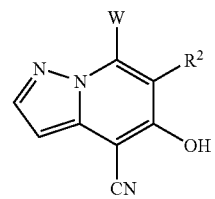

(7)

wherein $R^2$ represents a hydrogen atom, an optionally substituted C1-C8 alkyl group an optionally substituted C2-C8 alkenyl group, an optionally substituted (C2-C8 alkynyl group, an optionally substituted C6-14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, $—OR^{2a}$, $—SR^{2b}$, $—NR^{2c}R^{2d}$, $—C(=O)R^{2e}$, $—S(=O)_2NR^{2f}R^{2g}$, $—C(=O)OR^{2h}$, $—C(=O)NR^{2i}R^{2j}$, $—NR^{2k}C(=O)R^{2l}$ and $—NR^{2m}S(=O)_2R^{2n}$;

$R^{2y}$ (y represents a, b, c, d, e, f, g, h, i, j, k, m or n) may be identical or different, and represents hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single load to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when $R^2$ is an optionally substituted C6-C14 aryl group or an optionally substituted heteroaryl group and two or more substituents of $R^2$ bond to $R^2$ these substituents may bond to each other via an oxygen atom, a nitrogen atom, a sulfur atoms or a single bond to form a ring, and W represents a halogen atom.

44. A pyrazolo[1,5-a]pyridine derivative represented by formula (8) or salt thereof:

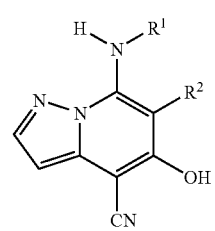

(8)

wherein $R^1$ represents an optionally substituted C1-C8 alkyl group, an optionally substituted C2-C5 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group:

the substituent(s) of $R^1$ are one or more substituent(s) selected from the group consisting of a halogen atom, a cyano atom, a nitro atom, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, —$OR^{1a}$, —$SR^{1b}$, —$NR^{1c}R^{1d}$, —$C(=O)R^{1e}$, —$S(=O)_2NR^{1f}R^{1g}$, —$C(=O)OR^{1h}$, —$C(=O)NR^{1i}R^{1j}$, —$NR^{1k}C(=O)R^{1l}$ and —$NR^{1m}S(=O)_2R^{1n}$;

$R^{1x}$ represents a, b, c, d, e, f, g, h, i, j, k, l, m or n) may be identical or different, and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$ these substituents may bond to each other via an oxygen atom, a nitrogen atom, a sulfur atom or a single bond to form a ring; and $R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 sibyl group, —$OR^{2a}$, —$SR^{2b}$, —$NR^{2c}R^{2d}$, —$C(=O)R^{2e}$, —$S(=O)_2NR^{2f}R^{2g}$, —$C(=O)OR^{2h}$, —$C(=O)NR^{2i}R^{2j}$, —$NR^{2k}C(=O)R^{2l}$ and —$NR^{2m}S(=O)_2R^{2n}$;

$R^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ ad to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substitute heteroarylalkyl group;

when $R^2$ is an optionally substituted C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring.

45. A pyrazolo[1,5-a]pyridine derivative represented by formula (9) or salt thereof:

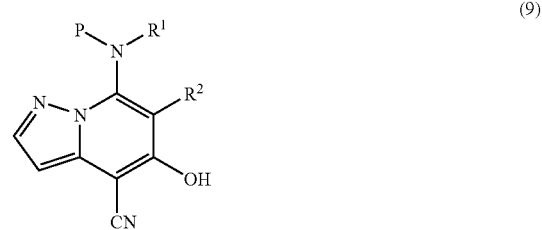

(9)

wherein $R^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of $R^1$ are one or more substituent(s) selected from the group consisting of a halogen atom, a cyano group, a nitro group, an optionally substituted C1-C8 alkyl group, an optionally substituted C3-C8 cycloalkyl group an optionally substituted aliphatic heterocyclic group, an optionally substituted C6-C14 aryl group, an optionally substituted heteroaryl group, —$OR^{1a}$, —$SR^{1b}$, —$NR^{1c}R^{1d}$, —$C(=O)R^{1e}$, —$S(=O)_2NR^{1f}R^{1g}$, —$C(=O)OR^{1h}$, —$C(=O)NR^{1i}R^{1j}$, —$NR^{1k}C(=O)R^{1l}$ and —$NR^{1m}S(=O)_2R^{1n}$;

$R^{1x}$ represents a, b, c, d, e, f, g, h, i, j, k, l, m or n) may be identical or different, and represents a hydrogen atom, an optionally substituted C1-C8 alkyl group (when two C1-C8 alkyl groups as $R^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$, these substituents may bond to each other via an oxygen atom, a nitrogen atom, a sulfur atom or a single bond to form a ring; $R^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, —$OR^{2a}$, —$SR^{2b}$, —$NR^{2c}R^{2d}$, —$C(=O)R^{2e}$, —$S(=O)_2NR^{2f}R^{2g}$, —$C(=O)OR^{2h}$, —$C(=O)NR^{2i}R^{2j}$, —$NR^{2k}C(=O)R^{2l}$ and —$NR^{2m}S(=O)_2R^{2n}$;

R²ʸ (y represents a, b, c, d, e, f, g, h, i, j, k, l, m or n) any be identical or different, and represents a hydrogen atom, an optionally substituted C1-C8 alkyl group (when two C1-C8 alkyl groups as R²ʸ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when R² is an optionally substituted C6-C14 aryl group or an optionally substituted heteroaryl group and two or more substituents of R² bond to R², these substituents may bond to each other via an oxygen atom, a nitrogen atom, a sulfur atom or a single bond to form a ring;

P represents a protective group or an amino group.

46. A pyrazolo[1,5-a]pyridine derivative represented by formula (10) or salt thereof:

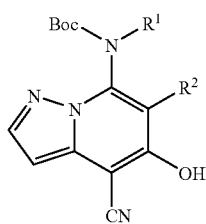

(10)

wherein
R¹ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of R¹ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, —OR¹ᵃ, —SR¹ᵇ, —NR¹ᶜR¹ᵈ, —C(=O)R¹ᵉ, —S(=O)₂NR¹ᶠR¹ᵍ, —C(=O)OR¹ʰ, —C(=O)NR¹ⁱR¹ʲ, —NR¹ᵏC(=O)R¹ˡ and —NR¹ᵐS(=O)₂R¹ⁿ; R¹ˣ (x represents a, b, c, d, e, f, g, h, i, j, k, l, m or n) may be identical or different, and represents a hydrogen atom, an optionally substituted C1-C8 alkyl group (when two C1-C8 alkyl groups as R¹ˣ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group or an optionally substituted aliphatic heterocyclylalkyl group;

when R¹ is an optionally substituted C6-C14 aryl group or an optionally substituted heteroaryl group and two or more substituents of R¹ bond to R¹, these substituents may bond to each other via an oxygen atom, nitrogen atom, a sulfur atom or a single bond to form a ring;

R² represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of R² are one or more substituent(s) selected from the group consisting of a halogen atom, a cyano group, a nitro group, an optionally substituted C1-C8 alkyl group, —OR²ᵃ, —SR²ᵇ, —NR²ᶜR²ᵈ, —C(=O)R²ᵉ, —S(=O)₂NR²ᶠR²ᵍ, —C(=O)OR²ʰ, —C(=O)NR²ⁱR²ʲ, —NR²ᵏC(=O)R²ˡ and —NR²ᵐS(=O)₂R²ⁿ; R²ʸ (y represents a, b, c, d, e, f, g, h, i, j, k, l, m or n) may be identical or different, and represents a hydrogen atom, an optionally substituted C1-C8 alkyl group (when two C1-C8 alkyl groups as R²ʸ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when R² is an optionally substituted C6-C14 aryl group or an optionally substituted heteroaryl group and two or more substituents of R² bond to R², these substituents may bond to each other via an oxygen atom, a nitrogen atom, a sulfur atom or a single bond to form a ring; and Boc represents tert-butoxycarbonyl.

47. A pyrazolo[1,5-a]pyridine derivative represented by formula (11) or salt thereof:

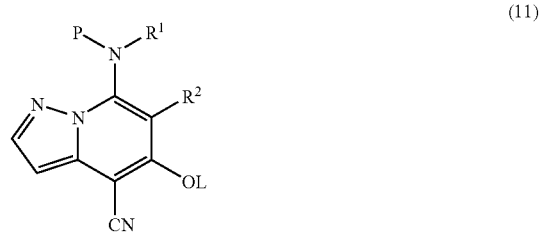

(11)

wherein
R¹ represents an optionally substituted C1-C8 alkyl group, an optionally substituted C2-C8 alkenyl group, an optionally substituted C2-C8 alkynyl group, an optionally substituted C6C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of R¹ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, —OR$^{1a}$, —SR$^{1b}$, —NR$^{1c}$R$^{1d}$, —C(=O)R$^{1e}$, —S(=O)$_2$NR$^{1f}$R$^{1g}$, —C(=O)OR$^{1h}$, —C(=O)NR$^{1i}$R$^{1j}$, —NR$^{1k}$C(=O)R$^{1l}$ and —NR$^{1m}$S(=O)$_2$R$^{1n}$;

R$^{1x}$ (x represents a, b, c, d, e, f, g, h, i, j, k, l, m or n) may be identical or different, and represents a hydrogen atom, an optionally substituted C1-C8 alkyl group (when two C1-C8 alkyl groups as R$^{1x}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heteroarylalkyl group, an optionally substituted C7-C16 aralkyl group, an optionally substituted heteroarylalkyl group or an optionally substituted aliphatic heterocyclylalkyl group;

when R$^1$ is an optionally substituted C6-C14 aryl group or an optionally substituted heteroaryl group and two or more substituents of R$^1$ bond to R$^1$ these substituents may bond to each other via an oxygen atom, a nitrogen atom, a sulfur atom or a single bond to form a ring;

R$^2$ represents a hydrogen atom, an optionally substituted C1-C8 alkyl group, an optionally substituted C2-C8 alkenyl group, an optionally substituted C2-C8 alkynyl group, an optionally substituted C2-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of R$^2$ are one or more substituent(s) selected from the group consisting of a halogen atom, a cyano group, a nitro group, an optionally substituted C1-C8 alkyl group, —OR$^{2a}$, —SR$^{2b}$, —NR$^{2c}$R$^{2d}$, —C(=O)R$^{2e}$, —S(=O)$_2$NR$^{2f}$R$^{2g}$, —C(=O)OR$^{2h}$, —C(=O)NR$^{2i}$R$^{2j}$, —NR$^{2k}$C(=O)R$^{2l}$ and —NR$^{2m}$S(=O)$_2$R$^{2n}$;

R$^{2y}$ (y represents a, b, c, d, e, f, g, h, i, j, k, l, m or n) may be identical or different, and represents a hydrogen atom, an optionally substituted C1C8 alkyl group (when two C1-C8 alkyl groups as R$^2$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when R$^2$ is an optionally substituted C6-C14 aryl group or an optionally substituted heteroaryl group and two or more substituents of R$^2$ bond in R$^2$ these substituents may bond to each other via an oxygen atom, a nitrogen atom, a sulfur atom or a single bond to form a ring;

P represents a protective group of an amino group, and

L represents perfluoroalkylsulfonyl.

48. A pyrazolo[1,5-a]pyridine derivative represented by formula (12) or salt thereof:

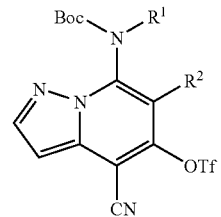

(12)

wherein
R$^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of R$^1$ are one or more substituent(s) selected from the group consisting of a halogen atom, a cyano group, a nitro group, an optionally substituted C1-C8 alkyl group, an optionally substituted C3-C8 cycloalkyl group, an optionally substituted aliphatic heterocyclic group, an optionally substituted C6-C14 aryl group, an optionally substituted heteroaryl group, —OR$^{1a}$, —SR$^{1b}$, —NR$^{1c}$R$^{1d}$, —C(=O)R$^{1e}$, —S(=O)$_2$NR$^{1f}$R$^{1g}$, —C(=O)OR$^{1h}$, —C(=O)NR$^{1i}$R$^{1j}$, —NR$^{1k}$C(=O)R$^{1l}$ and —NR$^{1m}$S(=O)$_2$R$^{1n}$;

R$^{1x}$ (x represents a, b, c, d, e, f, g, h, i, j, k, l, m or n) may be identical or different, and represents a hydrogen atom, an optionally substituted C1-C8 alkyl group (when two C1-C8 alkyl groups as R$^{1x}$ bond to one nitrogen atom, they may bond to each other via oxygen atom, a nitrogen atom, a sulfur bond or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group, an optionally substituted heteroarylalkyl group or an optionally substituted aliphatic heterocyclylalkyl group;

when R$^1$ is an optionally substituted C6-C14 aryl group or an optionally substituted heteroaryl group and two or more substituents of R$^1$ bond to R$^1$ these substituents may bond to each other via an oxygen atom, a nitrogen atom, a sulfur atom or a single bond to from a ring;

R$^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of R$^2$ are one or more substituent(s) selected from the group consisting of a halogen atom, a cyano group, a nitro group, an optionally substituted C1-C8 alkyl group, —OR$^{2a}$, —SR$^{2b}$, —NR$^{2c}$R$^{2d}$, —C(=O)R$^{2e}$, —S(=O)$_2$NR$^{2f}$R$^{2g}$, —C(=O)OR$^{2h}$, —C(=O)NR$^{2i}$R$^{2j}$, —NR$^{2k}$C(=O)R$^{2l}$ and —NR$^{2m}$S(=O)$_2$R$^{2n}$;

$R^{2y}$ (y presents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to from a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when $R^2$ is an optionally substitute a C6-C14 aryl group or an optionally substituted heteroaryl group and two or more substituents of $R^2$ bond to $R^2$, these substituents may bond to each other via an oxygen atom, a nitrogen atom, a sulfur atom or a single bond to form a ring;

Boc represents tert-butoxycarbonyl, and

Tf represents trifluoromethanesulfonyl.

49. A pyrazolo[1,5-a]pyridine derivative represented by formula (13) or salt thereof:

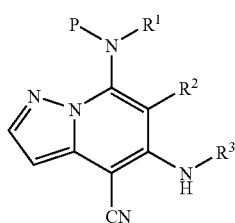

(13)

wherein $R^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of $R^1$ are one or more substituent(s) selected from the group consisting of a halogen atom, a cyano group, a nitro group, an optionally substituted C1-C8 alkyl group, an optionally substituted C3-C8 aryl group, an optionally substituted aliphatic heterocyclic group, an optionally substituted C6-C14 aryl group, an optionally substituted heteroaryl group, —$OR^{1a}$, —$SR^{1b}$, —$NR^{1c}R^{1d}$, —$C(=O)R^{1e}$, —$S(=O)_2NR^{1f}R^{1g}$, —$C(=O)OR^{1h}$, —$C(=O)NR^{1i}R^{1j}$, —$NR^{1k}C(=O)R^{1l}$ and —$NR^{1m}S(=O)_2R^{1n}$;

$R^{1x}$ (x represents a, b, c, d, e, f, g, h, i, j, k, l, m or n) may be identical or different, and represents a hydrogen atom, an optionally substituted C1-C8 alkyl group (when two C1-C8 alkyl group as $R^{1x}$ bond to one nitrogen atom they may bond to each other via, an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-16 aralkyl group, an optionally substituted heteroarylalkyl group or an optionally substituted aliphatic heterocyclylalkyl group;

when $R^1$ is an optionally substituted C6-C14 aryl group or an optionally substituted heteroaryl group and two or more substituents of $R^1$ bond to $R^1$ these substituents may bond to each other via an oxygen atom, a nitrogen atom, a sulfur atom or a single bond to form a ring;

$R^2$ represents a hydrogen atom, an optionally substituted C1-C8 alkyl group, an optionally substituted C2-C8 alkenyl group, an optionally substituted C1-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of $R^2$ are one or more substituent(s) selected from the group consisting of a halogen atom, a cyano group, a nitro group, an optionally substituted C1-C8 alkyl group, —$OR^{2a}$, —$SR^{2b}$, —$NR^{2c}R^{2d}$, —$C(=O)R^{2e}$, —$S(=O)_2NR^{2f}R^{2g}$, —$C(=O)OR^{2h}$, —$C(=O)NR^{2i}R^{2j}$, —$NR^{2k}C(=O)R^{2l}$ and —$NR^{2m}S(=O)_2R^{2n}$;

$R^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as $R^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, optionally substituted C7-C16 aralkyl group or an optionally substituted heteroarylalkyl group;

when $R^2$ is an optionally substituted C6-C14 aryl group or an optionally substituted heteroaryl group and two or more substituents of $R^2$ bond to $R^2$ these substituents may bond to each other via an oxygen atom, a nitrogen atom, a sulfur atom or a single bond to form a ring;

$R^3$ represents an optionally substituted C1-C8 aryl group, an optionally substituted C3-C8 cycloalkyl group or an optionally substituted aliphatic heterocyclic group;

the substituent(s) of $R^3$ are one or more substituent(s) selected from the group consisting of a halogen atom, a cyano group, a nitro group, —$OR^{3a}$, —$SR^{3b}$, —$NR^{3c}R^{23d}$, an optionally substituted C1-C8 alkyl group, an optionally substituted C3-C8 cycloalkyl group and an optionally substituted aliphatic heterocyclic group;

$R^{3z}$ (z represents a, b, c or d) may be identical or different and represents a hydrogen atom, an optionally substituted C1-C8 alkyl group (when two C1-C8 alkyl groups as $R^{2z}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group; and the substituent(s) of substituent of $R^1$, $R^2$ and $R^3$ are, unless specifically defined, one or more substituent(s) selected from the group consisting of a halogen atom; a hydroxyl group; a cyano group; a nitro group; an amino group; an oxo group; a carboxyl group; a trifluromethyl group; a pentafluoroethyl group; a trifluoromethoxy group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group optionally substituted with methyl group(s), halogen atom(s), hydroxyl group(s) or cyano group(s); an aliphatic heterocyclic group optionally substituted with methyl group(s), halogen group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s), and P represents a protective group of an amino group.

50. A pyrazolo[1,5-a]pyridine derivative represented by formula (14) or salt thereof:

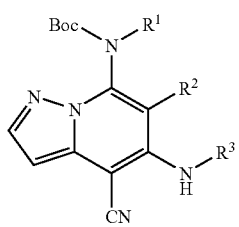

(14)

wherein

R$^1$ represents an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted C7-C16 aralkyl group, an optionally substituted heteroarylalkyl group, an optionally substituted C3-C8 cycloalkyl group or an optionally substituted aliphatic heterocyclic group;

the substituent(s) of R$^1$ are one or more substituent(s) selected from the group consisting of a halogen atom, a cyano group, a nitro group, an optionally substituted C1-C8 alkyl group, an optionally substituted C3-C8 aryl group, an optionally substituted aliphatic heterocyclic group, an optionally substituted C6-C14 aryl group, an optionally substituted heteroaryl group, —OR$^{1a}$, —SR$^{1b}$, —NR$^{1c}$R$^{1d}$, —C(=O)R$^{1e}$, —S(=O)$_2$NR$^{1f}$R$^{1g}$, —C(=O)OR$^{1h}$, —C(=O)NR$^{1i}$R$^{1j}$, —NR$^{1k}$C(=O)R$^{1l}$ and —NR$^{1m}$S(=O)$_2$R$^{1n}$;

R$^{1x}$ (x represents a, b, c, d, e, f, g, h, i, j, k, l, m or n) may be identical or different, and represents a hydrogen atom, an optionally substituted C1-C8 alkyl group (when two C1-C8 alkyl group as R$^{1x}$ bond to one nitrogen atom, they may bond to each other via, an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-16 aralkyl group, an optionally substituted heteroarylalkyl group or an optionally substituted aliphatic heterocyclylalkyl group;

when R$^1$ is an optionally substituted C6-C14 aryl group or an optionally substituted heteroaryl group and two or more substituents of R$^1$ bond to R$^1$ these substituents may bond to each other via an oxygen atom, a nitrogen atom, a sulfur atom or a single bond to form a ring;

R$^2$ represents a hydrogen atom, an optionally substituted C1-C8 alkyl group, an optionally substituted C2-C8 alkenyl group, an optionally substituted C2-C8 alkynyl group, an optionally substituted C6-C14 aryl group, an optionally substituted heteroaryl group, an optionally substituted aliphatic heterocyclic group, an optionally substituted C7-C16 aralkyl group, an optionally substituted C3-C8 cycloalkyl group or an optionally substituted heteroarylalkyl group;

the substituent(s) of R$^2$ are one or more substituent(s) selected from the group consisting of a halogen atom, a cyano group, a nitro group, an optionally substituted C1-C8 alkyl group, —OR$^{2a}$, —SR$^{2b}$, —NR$^{2c}$R$^{2d}$, —C(=O)R$^{2e}$, —S(=O)$_2$NR$^{2f}$R$^{2g}$, —C(=O)OR$^{2h}$, —C(=O)NR$^{2i}$R$^{2j}$, —NR$^{2k}$C(=O)R$^{2l}$ and —NR$^{2m}$S(=O)$_2$R$^{2n}$;

R$^{2y}$ (y represents a, b, c, d, e, f, g, h, i, j, k, l, m or n) may be identical or different, and represents a hydrogen atom, an optionally substituted C1-C8 alkyl group (when two C1-C8 alkyl groups as R$^{2y}$ bond to one nitrogen atom, they may bond to each other via an oxygen atom, a nitrogen atom, a sulfur atom or a single bond to form a ring), an optionally substituted C6-C14 aryl group, an optionally substituted heteroaryl group, an optionally substituted C3-C8 cycloalkyl group, an optionally substituted aliphatic heterocyclic group, an optionally substituted C7-C16 aralkyl group or an optionally substituted heteroarylalkyl group;

when R$^2$ is an optionally substituted C6-C14 aryl group or an optionally substituted heteroaryl group and two or more substituents of R$^2$ bond to R$^2$ these substituents may bond to each other via an oxygen atom, a nitrogen atom, a sulfur atom or a single bond to form a ring;

R$^3$ represents an optionally substituted C1-C8 aryl group, an optionally substituted C3-C8 cycloalkyl group or an optionally substituted aliphatic heterocyclic group; the substituent(s) of R$^3$ are one or more substituent(s) selected from the group consisting of a halogen atom, a cyano group, a nitro group, —OR$^{3a}$, —SR$^{3b}$, —NR$^{3c}$R$^{3d}$, an optionally substituted C1-C8 alkyl group, an optionally substituted C3-C8 cycloalkyl group and an optionally substituted aliphatic heterocyclic group;

R$^{3z}$ (z represents a, b, c or d) may be identical or different and represents a hydrogen atom, an optionally substituted C1-C8 alkyl group (when two C1-C8 allyl group as R$^{3z}$ bond to one nitrogen atom, they may bond to each other via an oxygen atom, a nitrogen atom, a sulfur atom or a single bond to form a ring), an optionally substituted C6-C14 and group, an optionally substituted heteroaryl group, an optionally substituted C3-C8 cycloalkyl group, an optionally substituted aliphatic heterocyclic group, an optionally substituted C7-16 aralkyl group or an optionally substituted heteroarylalkyl group; and the substituent(s) of substituent of R$^1$, R$^2$ and R$^3$ are, unless specifically defined, one or more substituent(s) selected from the group consisting of a halogen atom; a hydroxyl group; a cyano group; a nitro group; an amino group; an oxo group; a carboxyl group; a trifluromethyl group; a pentafluoroethyl group; a trifluoromethoxy group; a C1-C8 alkyl group optionally substituted with halogen atom(s), hydroxyl group(s), cyano group(s) or oxo group(s); a C3-C8 cycloalkyl group optionally substituted with methyl group(s), halogen atom(s), hydroxyl group(s), cyano group(s) or oxo group(s); a C1-C8 alkoxy group optionally substituted with halogen atom(s), hydroxyl group(s) or cyano group(s); a C3-C8 cycloalkyl-oxy group optionally substituted with methyl group(s), halogen atom(s), hydroxyl group(s) or cyano group(s); an aliphatic heterocyclic group optionally substituted with methyl group(s), halogen atom(s), hydroxyl group(s) or cyano group(s); a C6-C14 aryl group optionally substituted with methyl group(s), halogen atom(s), hydroxyl group(s) or cyano group(s); and a heteroaryl group optionally substituted with methyl group(s), halogen atom(s), hydroxyl group(s) or cyano group(s), Boc represents tert-butoxycarbonyl.

51. The pyrazolo[1,5-a]pyridine derivative represented by any of formulae (8) to (14) or salt thereof according to any of claims 44 to 50 except a compound wherein $R^1$ is a C1-C8 alkyl group optionally substituted with $-NR^{1c}R^{1d}$, $-NR^{1k}-CO-R^{1l}$ or $-NR^{1m}S(=O)_2R^{1n}$; or a C3-C8 cycloalkyl group optionally substituted with $-NR^{1c}R^{1d}$, $-NR^{1k}-CO-R^{1l}$ or $-NR^{1m}S(=O)_2R^{1n}$.

52. The pyrazolo[1,5-a]pyridine derivative or pharmaceutically acceptable salt thereof according to claim 2, except for:

compounds wherein $R^1$ is an unsubstituted or fluorinated C1-C6 alkyl group or an unsubstituted C3-C7 cycloalkyl group; $R^2$ is an unsubstituted C1-C6 alkyl group or a C1-C6 alkyl group substituted with a halogen atom, a hydroxyl group or $-NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6 alkyl group or an unsubstituted C3-C7 cycloalkyl group); and $R^3$ unsubstituted C1-C6 alkyl group:

compounds wherein $R^1$ is an unsubstituted C1-C6 alkyl group or an unsubstituted or halogenated phenyl group; $R^2$ is an unsubstituted C1-C6 alkyl or a C1-C6 alkyl group substituted with a halogen atom, a —OH or $-NR^{2c}R^{2d}$ or an unsubstituted C3-C7 cycloalkyl group ($R^{2c}$ and $R^{2d}$, which may be identical or different, are independently a hydrogen atom, an unsubstituted or fluorinated C1-C6 alkyl group or an unsubstituted C3-C7 cycloalkyl group); and $R^3$ is an unsubstituted or fluorinated C1-C6 alkyl group or an unsubstituted C3-C7 cycloalkyl group; and compounds wherein $R^1$ is a C1-C8 alkyl group substituted with $-NR^{1c}R^{1d}$, $-NR^{1k}-CO-R^{1l}$ or $-NR^{1m}S(=O)_2R^{1n}$ or a C3-C8 cycloalkyl group substituted with $-NR^{1c}R^{1d}$, $-NR^{1k}-CO-R^{1k}$ or $-NR^{1m}S(=)_2R^{1n}$; and $R^3$ is an unsubstituted alkyl group or an alkyl group substituted with $OR^{3a}$.

53. A pharmaceutical composition comprising the pyrazolo[1,5-a]pyridine derivative or pharmaceutically acceptable salt thereof according to any of claims 1 to 41 and 52 and a pharmaceutically acceptable carrier.

* * * * *